(12) United States Patent
Dunkel et al.

(10) Patent No.: US 7,842,710 B2
(45) Date of Patent: Nov. 30, 2010

(54) CARBOXAMIDES

(75) Inventors: Ralf Dunkel, Lyons (FR); Hans-Ludwig Elbe, Wuppertal (DE); Benoit Hartmann, Langenfeld (DE); Jörg Nico Greul, Leichlingen (DE); Stefan Herrmann, Langenfeld (DE); Ulrike Wachendorff-Neumann, Neuwied (DE); Peter Dahmen, Neuss (DE); Karl-Heinz Kuck, Langenfeld (DE)

(73) Assignee: Bayer Cropscience AG, Monheim (DE)

( * ) Notice: Subject to any disclaimer, the term of this patent is extended or adjusted under 35 U.S.C. 154(b) by 845 days.

(21) Appl. No.: 10/588,491

(22) PCT Filed: Jan. 22, 2005

(86) PCT No.: PCT/EP2005/000633

§ 371 (c)(1),
(2), (4) Date: Jun. 7, 2007

(87) PCT Pub. No.: WO2005/074686

PCT Pub. Date: Aug. 18, 2005

(65) Prior Publication Data

US 2008/0058389 A1 Mar. 6, 2008

(30) Foreign Application Priority Data

Feb. 6, 2004 (DE) .................. 10 2004 005 787

(51) Int. Cl.
*A61K 31/4155* (2006.01)
*C07D 231/12* (2006.01)
(52) U.S. Cl. .................. 514/403; 548/364.4
(58) Field of Classification Search .......... 514/403; 548/364.4
See application file for complete search history.

(56) References Cited

U.S. PATENT DOCUMENTS

| 2007/0004793 A1 | 1/2007 | Dunkel et al. |
| 2007/0191454 A1 | 8/2007 | Dunkel et al. |
| 2007/0203148 A1 | 8/2007 | Dunkel et al. |
| 2007/0293455 A1 | 12/2007 | Dunkel et al. |
| 2008/0064874 A1 | 3/2008 | Dunkel et al. |
| 2008/0139389 A1 | 6/2008 | Kneen et al. |
| 2008/0293566 A1 | 11/2008 | Suty-Heinze et al. |
| 2009/0209769 A1 | 8/2009 | Straub |

FOREIGN PATENT DOCUMENTS

| JP | 2004-189738 | 7/2004 |
| WO | WO 03/010149 A1 | 2/2003 |

OTHER PUBLICATIONS

Belokon, Y.N., et al., "Synthesis of α-Amino Acids via Asymmetric Phase Transfer-Catalyzed Alkylation of Achiral Nickel(II) Complexes of Glycine-Derived Schiff Bases," *J. Am. Chem. Soc.* 125:12860-12871, American Chemical Society (first available on the web Sep. 30, 2003).

Cho, C.S., et al., "Ruthenium-catalyzed oxidative coupling and cyclization between 2-aminobenzyl alcohol and secondary alcohols leading to quinolines," *Tetrahedron* 59:7997-8002, Elsevier (Sep. 2003).

Dixon, W.J., et al., "Kinetics and mechanism of the addition of water and ring-opening of 2-methyl- and 2-aryl-4*H*-3,1-benzoxazines to 2-aminobenzyl esters in the acidic pH range; change in rate-limiting step with buffer concentration and evidence for a tetrahedral carbonyl addition intermediate," *J. Chem. Soc., Perkin Trans.* 2, No. 8:1503-1509, Royal Society of Chemistry (1997).

Mulzer, J. et al., "Chiral Acetals as Stereoinductors: Diastereoface Selective Alkylation of Dihydrobenzoxazine-Derived Amide Enolates," *J. Org. Chem.* 65:6540-6546, American Chemical Society (2000).

(Continued)

*Primary Examiner*—Taofiq A Solola
(74) *Attorney, Agent, or Firm*—Sterne, Kessler, Goldstein & Fox P.L.L.C.

(57) ABSTRACT

The invention relates to novel carboxamides of formula (I), in which M represents a phenyl ring, pyridine ring or pyrimidine, pyridazine or pyrazine ring, respectively monosubstituted by $R^8$, or represents a thiazole ring substituted by $R^{8-A}$; $R^8$ represents hydrogen, fluorine, chlorine, methyl, isopropyl, methylthio or trifluoromethyl; $R^8$ can also represent methoxy; $R^{8-A}$ represents hydrogen, methyl, methylthio or trifluoromethyl; $L^1$ represents $C_1$-$C_{10}$ alkene (alkanediyl); Q represents O, S, SO, $SO_2$ or $NR^9$; $L^2$ represents a direct bond, $SiR^{10}R^{11}$ or CO; R represents hydrogen, $C_1$-$C_8$ alkyl, $C_1$-$C_8$ alkoxy, $C_1$-$C_4$ alkoxy-$C_1$-$C_4$-alkyl, $C_1$-$C_4$ alkylthio-$C_1$-$C_4$-alkyl, $C_2$-$C_8$ alkenyl, $C_2$-$C_8$ alkynyl, $C_1$-$C_6$ haloalkyl, $C_2$-$C_6$-haloalkenyl, $C_2$-$C_6$ haloalkynyl or $C_3$-$C_6$ cycloalkyl; A represents the group of formula (AI); the remaining substituents are defined in claim 1. The inventive substances have a powerful microbicidal action and can be used to control undesirable micro-organisms such as fungi and bacteria in the phytoprotection and material protection fields.

(I)

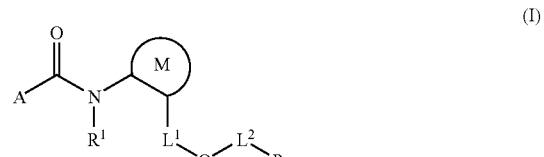

(AI)

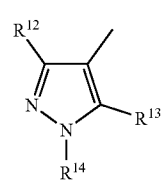

7 Claims, No Drawings

OTHER PUBLICATIONS

Raiford, L.C. and Clark, E.P., "Behavior of Mixed O-Acyl-N-Acyl Derivatives in Which the Reacting Groups Are Not on Adjacent Carbon Atoms," *J. Am. Chem. Soc. 48*:483-489, American Chemical Society (1926).

Roussel, P., et al., "Inhibition of the Tissue Factor/Factor VIIa Complex—Lead Optimisation Using Combinatorial Chemistry," *Tetrahedron 55*:6219-6230, Pergamon Press (1999).

Tsoungas, P.G. and Searcey, M., "A convenient access to benzo-substituted phthalazines as potential precursors to DNA intercalators," *Tetrahedron Lett. 42*:6589-6592, Pergamon Press (2001).

Beilstein Registry No. 3325417, "Benzoic acid-(2-methoxymethyl-anilide)," Beilstein Institut zur Foerderung der Chemischen Wissenschaften, 2 pages (1988-2003).

Beilstein Registry No. 9326393, "Furan-2-carboxylic acid (2-hydromethyl-phenyl)-amide," Beilstein Institut zur Foerderung der Chemischen Wissenschaften, 2 pages (1988-2003).

Beilstein Registry No. 1216128, "2-Benzoylamido-6-chlor-benzylalkohol," Beilstein Institut zur Foerderung der Chemischen Wissenschaften, 2 pages (1988-2003).

Dialog File 351, Accession No. 13194256, WPI English language abstract of WO 03/010149 (listed on accompanying PTO/SB/08A as Document FP1).

Patent Abstracts of Japan, English language abstract of JP 2004-189738 (listed on accompanying PTO/SB/08A as Document FP2).

Co-pending U.S. Appl. No. 12/373,218, Straub, A., filed Jul. 12, 2007.

CARBOXAMIDES

The present invention pertains to new carboxamides, several processes for their synthesis and their use for combating undesired microorganisms.

It is already known that numerous carboxamides possess fungicidal properties (see, for example, WO 03/010149, WO 02/059086, EP-A 0 824 099, EP-A 0 737 682, EP-A 0 591 699, EP-A 0 589 301, EP-A 0 545 099, DE-A 24 09 011, DE-A 20 06 472, JP-A 2001-302605, JP-A 10-251240, JP-A 8-176112, JP-A 8-92223 and JP-A 53-72823). Thus numerous alkyl carboxamides have already become known that are not substituted in the alkyl portion, such as, for example, N-allyl-N-[2-(1,3-dimethylbutyl)phenyl]-1-methyl-3-(trifluoromethyl)-1H-pyrazole-4-carboxamide from WO 02/059086, N-[2-(1,3-dimethylbutyl)phenyl]-2,4-dimethyl-1,3-thiazole-5-carboxamide from EP-A 0 824 699 and 5-fluoro-1,3-dimethyl-N-[2-(1,3,3-trimethylbutyl)phenyl]-1H-pyrazole-4-carboxamide from WO 03/010149. The effectiveness of these materials is good, but they leave something to be desired in many cases, for example at low application rates.

New carboxamides of the formula (I)

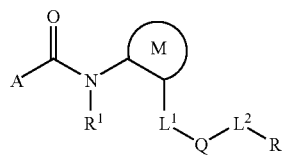

(I)

were found, in which $R^1$ stands for hydrogen, $C_1$-$C_8$ alkyl, $C_1$-$C_6$ alkylsulfinyl, $C_1$-$C_6$ alkylsulfonyl, $C_1$-$C_4$-alkoxy-$C_1$-$C_4$-alkyl, $C_3$-$C_8$ cycloalkyl; $C_1$-$C_6$ haloalkyl, $C_1$-$C_4$ haloalkylthio, $C_1$-$C_4$ haloalkylsulfinyl, $C_1$-$C_4$ haloalkylsulfonyl, halo-$C_1$-$C_4$-alkoxy-$C_1$-$C_4$-alkyl, $C_3$-$C_8$ halocycloalkyl with 1 to 9 fluorine, chlorine and/or bromine atoms in each case; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl with 1 to 13 fluorine, chlorine and/or bromine atoms in each case; ($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl with 1 to 9 fluorine, chlorine and/or bromine atoms in each case; or —C(=O)C(=O)$R^2$, —CONR$^3$R$^4$ or —CH$_2$NR$^5$R$^6$, $R^2$ stands for hydrogen, $C_1$-$C_8$ alkyl, $C_1$-$C_8$ alkoxy, $C_1$-$C_4$-alkoxy-$C_1$-$C_4$-alkyl, $C_3$-$C_8$ cycloalkyl; $C_1$-$C_6$ haloalkyl, $C_1$-$C_6$ haloalkoxy, halo-$C_1$-$C_4$-alkoxy$_1$-$C_4$-alkyl, $C_3$-$C_8$ halocycloalkyl with 1 to 9 fluorine, chlorine and/or bromine atoms in each case, $R^3$ and $R^4$ stand independently of one another in each case for hydrogen, $C_1$-$C_8$ alkyl, $C_1$-$C_4$-alkoxy$_1$-$C_4$-alkyl, $C_3$-$C_8$ cycloalkyl; $C_1$-$C_8$ haloalkyl, halo-$C_1$-$C_4$-alkoxy-$C_1$-$C_4$-alkyl, $C_3$-$C_8$ halocycloalkyl with 1 to 9 fluorine, chlorine and/or bromine atoms in each case, $R^3$ and $R^4$, moreover, form a substituted, saturated heterocycle with 5 to 8 ring atoms together with the nitrogen atom to which they are bound, with single or multiple, the same, or various substitution by halogen or $C_1$-$C_4$ alkyl, whereby the heterocycle can contain 1 or 2 additional, non-adjacent hetero atoms constituted by oxygen, sulfur or NR$^7$, $R^5$ and $R^6$ stand independently of one another for hydrogen, $C_1$-$C_8$-alkyl, $C_3$-$C_8$ cycloalkyl; $C_1$-$C_8$ haloalkyl, $C_3$-$C_8$ halocycloalkyl with 1 to 9 fluorine, chlorine and/or bromine atoms in each case, $R^5$ and $R^6$, moreover, form a substituted, saturated heterocycle with 5 to 8 ring atoms together with the nitrogen atom to which they are bound, with single or multiple, the same or various substitution by halogen or $C_1$-$C_4$ alkyl, whereby the heterocycle can contain 1 or 2 additional, non-adjacent hetero atoms constituted by oxygen, sulfur or NR$^7$, $R^7$ stands for hydrogen or $C_1$-$C_6$ alkyl, M stands in each case for a phenyl, pyridine or pyrimidine, pyridazine or pyrazine ring with a single substitution by $R^8$ or for a thiazole ring substituted by $R^{8-A}$, $R^8$ stands for hydrogen, fluorine, chlorine, methyl, isopropyl, methylthio or trifluoromethyl, $R^8$ also stands for methoxy, $R^{8-A}$ stands for hydrogen, methyl, methylthio or trifluoromethyl, $L^1$ stands for $C_1$-$C_{10}$ alkylene (alkanediyl), Q stands for O, S, SO, SO$_2$ or NR$^9$, $L^2$ stands for a direct link, SiR$^{10}$OR$^{11}$ or CO, R stands for hydrogen, $C_1$-$C_8$ alkyl, $C_1$-$C_8$ alkoxy, $C_1$-$C_4$-alkoxy$_1$-$C_4$-alkyl, $C_1$-$C_4$-alkylthio-$C_1$-$C_4$-alkyl, $C_2$-$C_8$ alkenyl, $C_2$-$C_8$ alkynyl, $C_1$-$C_6$ haloalkyl, $C_2$-$C_6$ haloalkenyl, $C_2$-$C_6$ haloalkynyl or $C_3$-$C_6$ cycloalkyl, $R^9$ stands for hydrogen, $C_1$-$C_8$ alkyl, $C_1$-$C_4$-alkoxy-$C_1$-$C_4$-alkyl, $C_1$-$C_4$-alkylthio-$C_1$-$C_4$-alkyl, $C_2$-$C_8$ alkenyl, $C_2$-$C_8$ alkynyl, $C_1$-$C_6$ haloalkyl, $C_2$-$C_6$ haloalkenyl, $C_2$-$C_6$ haloalkynyl or $C_3$-$C_6$ cycloalkyl, $R^{10}$ and $R^{11}$ stand independently of one another for hydrogen, $C_1$-$C_8$ alkyl, $C_1$-$C_8$ alkoxy, $C_1$-$C_4$-alkoxy-$C_1$-$C_4$-alkyl, $C_1$-$C_4$-alkylthio-$C_1$-$C_4$-alkyl or $C_1$-$C_6$ haloalkyl, A stands for the group of the formula (A1)

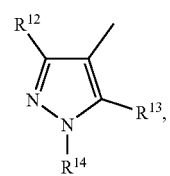

(A1)

in which $R^{12}$ stands for hydrogen, cyano, halogen, nitro, $C_1$-$C_4$ alkyl, $C_1$-$C_4$ alkoxy, $C_1$-$C_4$ alkylthio, $C_3$-$C_6$ cycloalkyl, $C_1$-$C_4$ haloalkyl, $C_1$-$C_4$ haloalkoxy or $C_1$-$C_4$ haloalkylthio, in each case with 1 to 5 halogen atoms, aminocarbonyl or aminocarbonyl-$C_1$-$C_4$-alkyl, $R^{13}$ stands for hydrogen, halogen, cyano, $C_1$-$C_4$ alkyl, $C_1$-$C_4$ alkoxy or $C_1$-$C_4$ alkylthio, $R^{14}$ stands for hydrogen, $C_1$-$C_4$ alkyl, hydroxy-$C_1$-$C_4$'s alkyl, $C_2$-$C_6$ alkenyl, $C_3$-$C_6$ cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkyl, $C_1$-$C_4$-haloalkoxy-$C_1$-$C_4$-alkyl in each case with 1 to 5 halogen atoms, or phenyl, or A stands for the group of the formula (A2)

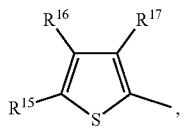
(A2)

in which
R$^{15}$ and R$^{16}$ stand independently of one another for hydrogen, halogen, C$_1$-C$_4$ alkyl or C$_1$-C$_4$ haloalkyl with 1 to 5 halogen atoms,
R$^{17}$ stands for halogen, cyano or C$_1$-C$_4$ alkyl, or C$_1$-C$_4$ haloalkyl or C$_1$-C$_4$ haloalkoxy with 1 to 5 halogen atoms in each case, or A stands for the group of the formula (A3)

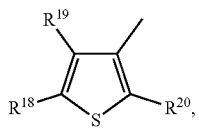
(A3)

in which
R$^{18}$ and R$^{19}$ stand independently of one another for hydrogen, halogen, C$_1$-C$_4$ alkyl or C$_1$-C$_4$ haloalkyl with 1 to 5 halogen atoms,
R$^{20}$ stands for hydrogen, halogen, C$_1$-C$_4$ alkyl or C$_1$-C$_4$ haloalkyl with 1 to 5 halogen atoms, or A stands for the group of the formula (A4)

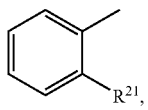
(A4)

in which
R$^{21}$ stands or hydrogen, halogen, hydroxy, cyano, C$_1$-C$_6$ alkyl, C$_1$-C$_4$ haloalkyl, C$_1$-C$_4$ haloalkoxy or C$_1$-C$_4$ haloalkylthio in each case with 1 to 5 halogen atoms, or A stands for the group of the formula (A5)

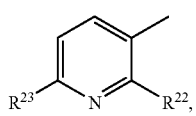
(A5)

in which
R$^{22}$ stands for halogen, hydroxy, cyano, C$_1$-C$_4$ alkyl, C$_1$-C$_4$ alkoxy, C$_1$-C$_4$ alkylthio, C$_1$-C$_4$ haloalkyl, C$_1$-C$_4$ haloalkylthio or C$_1$-C$_4$ haloalkoxy in each case with 1 to 5 halogen atoms, R$^{23}$ stands for hydrogen, halogen, cyano, C$_1$-C$_4$ alkyl, C$_1$-C$_4$ alkoxy, C$_1$-C$_4$ alkylthio, C$_1$-C$_4$ haloalkyl, C$_1$-C$_4$-haloalkoxy in each case with 1 to 5 halogen atoms, C$_1$-C$_4$ alkylsulfinyl or C$_1$-C$_4$ alkylsulfonyl, or A stands for the group of the formula (A6)

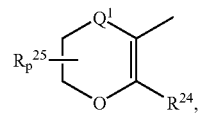
(A6)

in which
R$^{24}$ stands for C$_1$-C$_4$ alkyl or C$_1$-C$_4$ haloalkyl with 1 to 5 halogen atoms,
R$^{25}$ stands for C$_1$-C$_4$ alkyl,
Q$^1$ stands for S (sulfur), SO, SO$_2$ or CH$_2$,
p stands for 0, 1 or 2, whereby R$^{25}$ stands for identical or various groups if p is 2, or A stands for the group of the formula (A7)

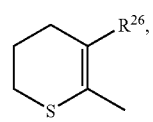
(A7)

in which
R$^{26}$ stands for C$_1$-C$_4$ alkyl or C$_1$-C$_4$ haloalkyl with 1 to 5 halogen atoms, or A stands for the group of the formula (A8)

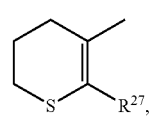
(A8)

in which
R$^{27}$ stands for C$_1$-C$_4$ alkyl or C$_1$-C$_4$ haloalkyl with 1 to 5 halogen atoms, or A stands for the group of the formula (A9)

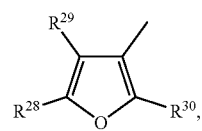
(A9)

in which
R$^{28}$ and R$^{29}$ stand independently of one another for hydrogen, halogen, amino, C$_1$-C$_4$ alkyl or C$_1$-C$_4$ haloalkyl with 1 to 5 halogen atoms,
R$^{30}$ stands for hydrogen, halogen, C$_1$-C$_4$ alkyl or C$_1$-C$_4$ haloalkyl with 1 to 5 halogen atoms, or
A stands for the group of the formula (A10)

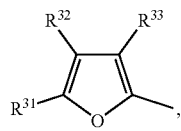
(A10)

in which
R$^{31}$ and R$^{32}$ stand independently of one another for hydrogen, halogen, amino, nitro, $C_1$-$C_4$ alkyl or $C_1$-$C_4$ haloalkyl with 1 to 5 halogen atoms,
R$^{33}$ stands for hydrogen, halogen, $C_1$-$C_4$ alkyl or $C_1$-$C_4$ haloalkyl with 1 to 5 halogen atoms, or
A stands for the group of the formula (A11)

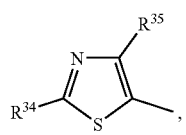
(A11)

in which
R$^{34}$ stands for hydrogen, halogen, amino, $C_1$-$C_4$ alkylamino, di-($C_1$-$C_4$ alkyl)amino, cyano, $C_1$-$C_4$ alkyl or $C_1$-$C_4$ haloalkyl with 1 to 5 halogen atoms,
R$^{35}$ stands for halogen, $C_1$-$C_4$ alkyl or $C_1$-$C_4$ haloalkyl with 1 to 5 halogen atoms, or
A stands for the group of the formula (A12)

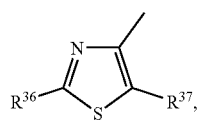
(A12)

in which
R$^{36}$ stands for hydrogen, halogen, amino, $C_1$-$C_4$ alkylamino, di-($C_1$-$C_4$ alkyl)amino, cyano, $C_1$-$C_4$ alkyl or $C_1$-$C_4$ haloalkyl with 1 to 5 halogen atoms,
R$^{37}$ stands for halogen, $C_1$-$C_4$ alkyl or $C_1$-$C_4$ haloalkyl with 1 to 5 halogen atoms, or
A stands for the group of the formula (A13)

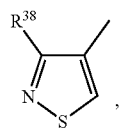
(A13)

in which
R$^{38}$ stands for halogen, $C_1$-$C_4$ alkyl or $C_1$-$C_4$ haloalkyl with 1 to 5 halogen atoms, or
A stands for the group of the formula (A14)

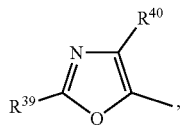
(A14)

in which
R$^{39}$ stands for hydrogen or $C_1$-$C_4$ alkyl,
R$^{40}$ stands for halogen or $C_1$-$C_4$ alkyl, or
A stands for the group of the formula (A15)

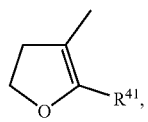
(A15)

in which
R$^{41}$ stands for $C_1$-$C_4$ alkyl or $C_1$-$C_4$ haloalkyl with 1 to 5 halogen atoms, or
A stands for the group of the formula (A16)

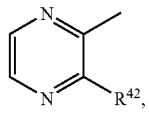
(A16)

in which
R$^{42}$ stands for hydrogen, halogen, $C_1$-$C_4$ alkyl or $C_1$-$C_4$ haloalkyl with 1 to 5 halogen atoms, or
A stands for the group of the formula (A17)

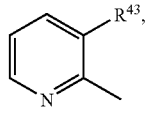
(A17)

in which
R$^{43}$ stands for halogen, hydroxy, $C_1$-$C_4$ alkyl, $C_1$-$C_4$ alkoxy, $C_1$-$C_4$ alkylthio, $C_1$-$C_4$ haloalkyl, $C_1$-$C_4$ haloalkylthio or $C_1$-$C_4$ haloalkoxy with 1 to 5 halogen atoms in each case, or
A stands for the group of the formula (A18)

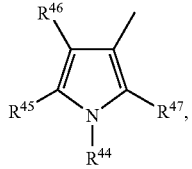
(A18)

in which
R$^{44}$ stands for hydrogen, cyano, C$_1$-C$_4$ alkyl, C$_1$-C$_4$ haloalkyl with 1 to 5 halogen atoms, C$_1$-C$_4$-alkoxy-C$_1$-C$_4$ alkyl, hydroxy-C$_1$-C$_4$ alkyl, C$_1$-C$_4$ alkylsulfonyl, di(C$_1$-C$_4$ alkyl)aminosulfonyl, C$_1$-C$_6$ alkylcarbonyl or in each case possibly substituted phenylsulfonyl or benzoyl,
R$^{45}$ stands for hydrogen, halogen, C$_1$-C$_4$ alkyl or C$_1$-C$_4$ haloalkyl with 1 to 5 halogen atoms,
R$^{46}$ stands for hydrogen, halogen, cyano, C$_1$-C$_4$ alkyl or C$_1$-C$_4$ haloalkyl with 1 to 5 halogen atoms,
R$^{47}$ stands for hydrogen, halogen, C$_1$-C$_4$ alkyl or C$_1$-C$_4$ haloalkyl with 1 to 5 halogen atoms, or
A stands for the group of the formula (A19)

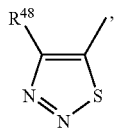
(A19)

in which
R$^{48}$ stands for C$_1$-C$_4$ alkyl, whereby R is not alkoxy if L$^2$ is a direct link.
Furthermore, it was found that carboxamides of the formula (I) are obtained by reacting
(a) carboxylic acid derivatives the formula (II)

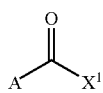
(II)

in which
A has the meanings specified above and
X$^1$ stands for halogen or hydroxy,
with aniline derivatives of the formula (III)

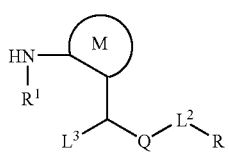
(III)

in which
R$^1$, M, Q, L$^2$ and R have the meanings specified above,
L$^3$ stands for hydrogen or C$_1$-C$_9$ alkyl,
possibly in the presence of a catalyst, possibly in the presence a condensation agent, possibly in the presence of an acid binder and possibly in the presence of a diluent, or
(b) carboxamides of the formula (IV)

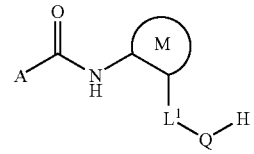
(IV)

in which M, L$^1$, Q and A have the meanings specified above are reacted with a compound of the formula (V)

(V)

in which
L$^2$ and R have the meanings specified above,
Y stands for halogen, triflate (trifluoromethylsulfonyl), mesylate (methylsulfonyl) or tosylate (4-methylphenylsulfonyl),
in the presence of a base and in the presence of a dilution medium, or
(c) carboxamides of the formula (I-a)

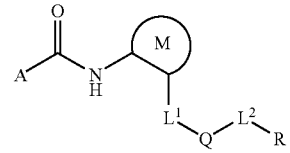
(I-a)

in which M, L$^1$, Q, L$^2$, R and A have the meanings specified above,
are reacted with halides of the formula (VI)

$$R^{1-A}-X^2 \quad (VI)$$

in which
X$^2$ stands for chlorine, bromine or iodine,
R$^{1-A}$ stands for C$_1$-C$_8$ alkyl, C$_1$-C$_6$ alkylsulfinyl, C$_1$-C$_6$ alkylsulfonyl, C$_1$-C$_4$-alkoxy-C$_1$-C$_4$-alkyl, C$_3$-C$_8$ cycloalkyl; C$_1$-C$_6$ haloalkyl, C$_1$-C$_4$ haloalkylthio, C$_1$-C$_4$ haloalkylsulfinyl, C$_1$-C$_4$ haloalkylsulfonyl, halo-C$_1$-C$_4$-alkoxy-C$_1$-C$_4$-alkyl, C$_3$-C$_8$ halocycloalkyl with 1 to 9 fluorine, chlorine and/or bromine atoms in each case; formyl, formyl-C$_1$-C$_3$-alkyl, (C$_1$-C$_3$-alkyl)carbonyl-C$_1$-C$_3$-alkyl, (C$_1$-C$_3$-alkoxy)carbonyl-C$_1$-C$_3$-alkyl; halo-(C$_1$-C$_3$-alkyl)carbonyl-C$_1$-C$_3$-alkyl, halo-(C$_1$-C$_3$-alkoxy)carbonyl-C$_1$-C$_3$-alkyl with 1 to 13 fluorine, chlorine- and/or bromine atoms in each case;
(C$_1$-C$_8$-alkyl)carbonyl, (C$_1$-C$_8$-alkoxy)carbonyl, (C$_1$-C$_4$-alkoxy-C$_1$-C$_4$-alkyl)carbonyl, (C$_3$-C$_8$-cycloalkyl) carbonyl; (C$_1$-C$_6$-haloalkyl)carbonyl, (C$_1$-C$_6$-haloalkoxy)carbonyl, (halo-$C_1$-$C_4$-alkoxy-$C_1$-$C_4$-alkyl) carbonyl, ($C_3$-$C_8$-halocycloalkyl)carbonyl with 1 to 9 fluorine, chlorine and/or bromine atoms in each case; or —C(=O)C(=O)$R^2$, —CONR$^3$R$^4$ or —CH$_2$NR$^5$R$^6$, whereby $R^2$, $R^3$, $R^4$, $R^5$ and $R^6$ have the meanings specified above, in the presence of a base and in the presence of a dilution medium.

Lastly, it was found that the new carboxamides of the formula (I) have very good microbicidal properties and can be used for combating undesirable microorganisms for both crop protection and material protection.

The inventive compounds may be present as mixtures of various possible to isomeric forms, particularly of stereoisomers, such as, for example, E- and Z-, threo- and erythro-, as well as optical isomers, but also as a where applicable. The E- and Z-isomers, the threo-, erythro-, and optical isomers and any mixtures of these isomers as well as possible tautomeric forms are claimed.

The inventive carboxamides are defined in general by the formula (I). A Preferred group definitions of the formulas given previously and hereafter are specified below. These definitions apply equally to the end products of the formula (I) as well as to all intermediate products.

$R^1$ stands preferably for hydrogen, $C_1$-$C_6$ alkyl, $C_1$-$C_4$ alkylsulfinyl, $C_1$-$C_4$ alkylsulfonyl, $C_1$-$C_3$-alkoxy-$C_1$-$C_3$-alkyl, $C_3$-$C_6$ cycloalkyl; $C_1$-$C_4$ haloalkyl, $C_1$-$C_4$ haloalkylthio, $C_1$-$C_4$ haloalkylsulfinyl, $C_1$-$C_4$ haloalkylsulfonyl, halo-$C_1$-$C_3$-alkoxy-$C_1$-$C_3$-alkyl, $C_3$-$C_8$ halocycloalkyl with 1 to 9 fluorine, chlorine and/or bromine atoms in each case; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl with 1 to 13 fluorine, chlorine and/or bromine atoms in each case;

($C_1$-$C_6$ alkyl)carbonyl, ($C_1$-$C_4$ alkoxy)carbonyl, ($C_1$-$C_3$-alkoxy-$C_1$-$C_3$-alkyl)carbonyl, ($C_3$-$C_6$ cycloalkyl)carbonyl; ($C_1$-$C_4$ haloalkyl)carbonyl, ($C_1$-$C_4$ haloalkoxy)carbonyl, (halo-$C_1$-$C_3$-alkoxy-$C_1$-$C_3$-alkyl)carbonyl, ($C_3$-$C_6$ halocycloalkyl)carbonyl with 1 to 9 fluorine, chlorine and/ or bromine atoms in each case; or —C(=O)C(=O)$R^2$, —CONR$^3$R$^4$ or —CH$_2$NR$^5$R$^6$.

$R^1$ stands particularly preferably for hydrogen, methyl, ethyl, n- or isopropyl, n-, iso-, sec- or tert-butyl, pentyl or hexyl, methylsulfinyl, ethylsulfinyl, n- or isopropylsulfinyl, n-, iso-, sec- or tert-butylsulfinyl, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulfinyl, trifluoromethylsulfonyl, trifluoromethoxymethyl; formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$—CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CO—CCl$_3$, —CH$_2$—CO—CH$_2$CF$_3$, —CH$_2$—CO—CH$_2$CCl$_3$, —(CH$_2$)$_2$—CO—CH$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, —CH$_2$—CO$_2$CH$_2$CCl$_3$, —CH$_2$—CO$_2$CCl$_2$CCl$_3$, —(CH$_2$)$_2$—CO$_2$CH$_2$CF$_3$, —(CH$_2$)$_2$—CO$_2$CF$_2$CF$_3$, —(CH$_2$)$_2$—CO$_2$CH$_2$CCl$_3$, —(CH$_2$)$_2$—CO$_2$CCl$_2$CCl$_3$; methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoromethylcarbonyl, trifluoromethoxycarbonyl, or —C(=O)C(=O)$R^2$, —CONR$^3$R$^4$ or —CH$_2$NR$^5$R$^6$.

$R^1$ stands most particularly preferably for hydrogen, methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$-, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

$R^2$ stands preferably for hydrogen, $C_1$-$C_6$ alkyl, $C_1$-$C_4$ alkoxy, $C_1$-$C_3$-alkoxy-$C_1$-$C_3$-alkyl, $C_3$-$C_6$ cycloalkyl; $C_1$-$C_4$ haloalkyl, $C_1$-$C_4$ haloalkoxy, halo-$C_1$-$C_3$-alkoxy-$C_1$-$C_3$-alkyl, $C_3$-$C_6$ halocycloalkyl with 1 to 9 fluorine, chlorine and/or bromine atoms in each case.

$R^2$ stands particularly preferably for hydrogen, methyl, ethyl, n- or isopropyl, tert-butyl, methoxy, ethoxy, n- or isopropoxy, tert-butoxy, methoxymethyl, cyclopropyl; trifluoromethyl, trifluoromethoxy.

$R^3$ and $R^4$ stand independently of one another preferably for hydrogen, $C_1$-$C_4$ alkyl, $C_1$-$C_4$-alkoxy-$C_1$-$C_4$-alkyl, $C_3$-$C_6$ cycloalkyl; $C_1$-$C_4$ haloalkyl, halo-$C_1$-$C_3$-alkoxy-$C_1$-$C_3$-alkyl, $C_3$-$C_6$ halocycloalkyl with 1 to 9 fluorine, chlorine and/or bromine atoms in each case.

$R^3$ and $R^4$, moreover, form a saturated, substituted heterocycle together with the nitrogen atom to which they are bound, preferably one with 5 or 6 ring atoms and single to quadruple, the same or various substitution by halogen or $C_1$-$C_4$ alkyl, whereby, the heterocycle can contain 1 or 2 additional, non-adjacent hetero atoms constituted by oxygen, sulfur or NR$^7$.

$R^3$ and $R^4$ stand independently of one another particularly preferably for hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^3$ and $R^4$, moreover, particularly preferably form a substituted unsaturated heterocycle with the nitrogen atom to which they are bound, preferably one singly to quadruply substituted by the same or various substituents comprised of fluorine, chlorine, bromine or methyl, said heterocycle being a morpholine, thimorpholine or piperazine, whereby the piperazine can be substituted by $R^7$ at the second nitrogen atom.

$R^5$ and $R^6$ stand independently of one another preferably for hydrogen, $C_1$-$C_6$ alkyl, $C_3$-$C_6$ cycloalkyl; $C_1$-$C_4$ haloalkyl, $C_3$-$C_6$ halocycloalkyl with 1 to 9 fluorine, chlorine and/or bromine atoms in each case.

$R^5$ and $R^6$, moreover, form a saturated, substituted heterocycle together with the nitrogen atom to which they are bound, preferably one with 5 or 6 ring atoms and single to quadruple, the same or various substitution by halogen or $C_1$-$C_4$ alkyl, whereby the heterocycle can contain 1 or 2 additional, non-adjacent hetero atoms constituted by oxygen, sulfur or NR$^7$.

$R^5$ and $R^6$ stand independently of one another particularly preferably for hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^5$ and $R^6$, moreover, particularly preferably form a substituted unsaturated heterocycle with the nitrogen atom to which they are bound, preferably one singly to quadruply substituted by the same or various substituents comprised of fluorine, chlorine, bromine or methyl, said heterocycle being a morpholine, thiomorpholine or piperazine, whereby the piperazine can be substituted by $R^7$ at the second nitrogen atom.

$R^7$ stands preferably for hydrogen or $C_1$-$C_4$ alkyl.

$R^7$ stands particularly preferably for hydrogen, methyl, ethyl, n- or isopropyl, n-, iso-, sec- or tert-butyl.

M stands preferably for one of the following cyclics

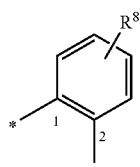

M-1

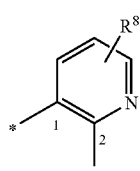

M-2

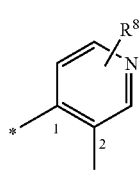

M-3

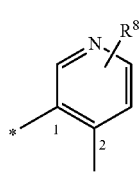

M-4

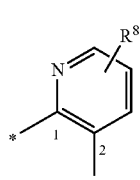

M-5

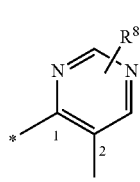

M-6

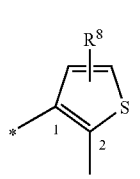

M-7

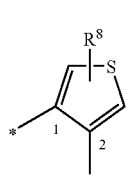

M-8

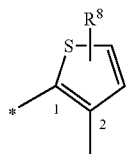

M-9

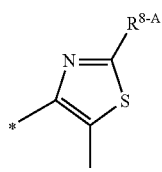

M-10

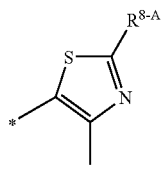

M-11

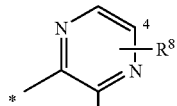

M-12

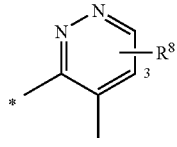

M-13

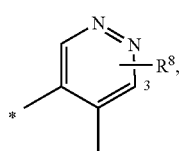

M-14 whereby the bond marked with an asterisk is linked to the amide.

M stands particularly preferably for a cyclic selected from M-1, M-2, M-3, M-6, M-7, M-10 or M-11.

M furthermore stands particularly preferably for a cyclic selected from M-1, M-2, M-3, M-4, M-5, M-6 or M-10, M-11.

M stands most particularly preferably for the cyclic M-1.

M furthermore stands most particularly preferably for the heterocycle M-2.

M furthermore stands most particularly preferably for the heterocycle M-3.

M furthermore stands most particularly preferably for the heterocycle M-6.

M furthermore stands most particularly preferably for the heterocycle M-7.

M furthermore stands most particularly preferably for the heterocycle M-10.

M furthermore stands most particularly preferably for the heterocycle M-11.

$R^8$ stands preferably for hydrogen.

$R^8$ furthermore stands preferably for fluorine in the case that M stands for M1, with the fluorine particularly preferred in the 4-, 5- or 6-position and most particularly preferably in the 4- or 6-position, especially in the 4-position.

$R^8$ furthermore stands preferably for chlorine in the case that M stands for M1, whereby the chlorine is particularly preferred in the 4- or 6-position.

$R^8$ furthermore stands preferably for methyl in the case that M stands for M1, whereby the methyl group is particularly preferred in 3-position and also particularly preferred in 4-position.

$R^8$ furthermore stands preferably for methoxy in the case that M stands for M1, whereby the methoxy group is particularly preferred in the 4-position.

$R^8$ furthermore stands preferably for trifluoromethyl in the case that M stands for M1, whereby the trifluoromethyl group is particularly preferred in the 4- or 6-position.

$R^8$ furthermore stands preferably for fluorine in the case that M stands for M-2, M-3, M-4 or M-5, whereby the fluorine is particularly preferred in the 6-position (M-2, M-3) or in the 3-position (M-4, M-5).

$R^8$ furthermore stands preferably for chlorine in the case that M stands for M-2, M-3, M-4 or M-5, whereby the chlorine is particularly preferred in the 6-position (M-2, M-3) or in the 3-position (M-4, M-5).

$R^8$ furthermore stands preferably for methyl in the case that M stands for M-2, M-3, M-4 or M-5, whereby the methyl group is particularly preferred in the 4-position (M-2) or in the 3-position (M-3, M-4, M-5).

$R^8$ furthermore stands preferably for methyl in the case that M stands for M-6, whereby the methyl group is particularly preferred in the 3-position.

$R^8$ furthermore stands preferably for trifluoromethyl in the case that M stands for M-6, whereby the trifluoromethyl group is particularly preferred in the 3-position.

$R^8$ furthermore stands preferably for chlorine in the case that M stands for M-7, M-8 or M-9, whereby the chlorine is particularly preferred in the 5-position (M-7, M-8) or in the 3-position (M-9).

$R^8$ furthermore stands preferably for methyl in the case that M stands for M-7, M-8 or M-9, whereby the methyl group is particularly preferred in the 5-position (M-7, M-8) or in the 3-position (M-9).

$R^8$ furthermore stands preferably for methyl in the case that M stands for M-12, whereby the methyl group is particularly preferred in the 4-position.

$R^8$ furthermore stands preferably for trifluoromethyl in the case that M stands for M-12, whereby the trifluoromethyl group is particularly preferred in the 4-position.

$R^8$ furthermore stands preferably for methyl in the case that M stands for M-13, whereby the methyl group is particularly preferred in the 3-position.

$R^8$ furthermore stands preferably for trifluoromethyl in the case that M stands for M-13, whereby the trifluoromethyl group is particularly preferred in the 3-position.

$R^8$ furthermore stands preferably for methyl in the case that M stands for M-14, whereby the methyl group is particularly preferred in the 3-position.

$R^8$ furthermore stands preferably for trifluoromethyl in the case that M stands for M-14, whereby the trifluoromethyl group is particularly preferred in the 3-position.

$R^{8-A}$ stands preferably for hydrogen.

$R^{8-A}$ furthermore stands preferably for methyl.

$R^{8-A}$ furthermore stands preferably for trifluoromethyl.

$L^1$ stands preferably for $C_1$-$C_6$ alkylene (alkanediyl).

$L^1$ stands particularly preferably for —$CH_2$—, —CH($CH_3$)— or —$(CH_2)_2$C$(CH_3)_2$—.

$L^1$ furthermore stands particularly preferably for —$(CH_2)_2$—.

Q stands preferably for O.

Q furthermore stands preferably for S.

Q furthermore stands preferably for SO.

Q furthermore stands preferably for $SO_2$.

Q furthermore stands preferably for $NR^9$, particularly preferably for NH.

$L^2$ stands preferably for a direct link.

$L^2$ furthermore stands preferably for $SiR^{10}R^{11}$.

$L^2$ furthermore stands preferably for CO.

R stands preferably for hydrogen, $C_1$-$C_6$ alkyl, $C_1$-$C_6$ alkoxy, $C_1$-$C_3$-alkoxy-$C_1$-$C_3$-alkyl, $C_1$-$C_3$-alkylthio-$C_1$-$C_3$-alkyl or $C_3$-$C_6$ cycloalkyl.

R furthermore stands preferably for $C_1$-$C_4$ haloalkyl.

R stands particularly preferably for hydrogen, methyl, ethyl, n- or isopropyl, n-, sec-, iso- or tert-butyl, methoxy, ethoxy, n- or isopropoxy, n-, sec-, iso- or tert-butoxy, methoxymethyl, ethoxymethyl, methoxyethyl, ethoxyethyl, methylthiomethyl, ethylthiomethyl, methylthioethyl, ethylthioethyl or cyclopropyl.

R furthermore stands particularly preferably for 1-methylbutyl, $C_1$-$C_2$-haloalkyl with 1 to 5 fluorine, chlorine or bromine atoms, cyclopentyl or cyclohexyl.

R stands most particularly preferably for hydrogen, methyl, ethyl, n- or isopropyl, iso- or tert-butyl, methoxy, isopropoxy, iso- or tert-butoxy, methoxymethyl or methylthiomethyl.

R furthermore stands most particularly preferably for sec-butyl, 1-methylbutyl, dichloromethyl, cyclopropyl, cyclopentyl or cyclohexyl.

R stands especially preferably for hydrogen, methyl, ethyl, n- or isopropyl, iso- or tert-butyl, methoxy, isopropoxy, iso- or tert-butoxy.

R furthermore stands especially preferably for sec-butyl or 1-methylbutyl.

$R^9$ stands preferably for hydrogen, $C_1$-$C_6$ alkyl, $C_1$-$C_3$-alkoxy-$C_1$-$C_3$-alkyl, $C_1$-$C_3$-alkylthio-$C_1$-$C_3$-alkyl or $C_3$-$C_6$ cycloalkyl.

$R^9$ stands particularly preferably for hydrogen, methyl, ethyl, n- or isopropyl, n-, sec-, iso- or tert-butyl, methoxymethyl, ethoxymethyl, methoxyethyl, ethoxyethyl, methylthiomethyl, ethylthiomethyl, methylthioethyl, ethylthioethyl or cyclopropyl.

$R^9$ stands most particularly preferably for hydrogen, methyl, ethyl, n- or isopropyl, iso- or tert-butyl, methoxymethyl or methylthiomethyl.

$R^9$ stands especially preferably for hydrogen or methyl.

$R^{10}$ and $R^{11}$ stand independently of one another preferably for $C_1$-$C_6$ alkyl, $C_1$-$C_6$ alkoxy, $C_1$-$C_3$-alkoxy-$C_1$-$C_3$-alkyl or $C_1$-$C_3$-alkylthio-$C_1$-$C_3$-alkyl.

$R^{10}$ and $R^{11}$ stand independently of one another particularly preferably for methyl, ethyl, methoxy, ethoxy, methoxymethyl, ethoxymethyl, methoxyethyl, ethoxyethyl, methylthiomethyl, ethylthiomethyl, methylthioethyl or ethylthioethyl.

$R^{10}$ and $R^{11}$ stand independently of one another most particularly preferably for methyl, methoxy, methoxymethyl or methylthiomethyl.

$R^{10}$ and $R^{11}$ stand especially preferably in each case for methyl.

A stands preferably for one of the groups A1, A2, A3, A4, A5, A6, A9, A10, A11, A12, A17 or A18.

A stands particularly preferably for one of the groups A1, A2, A4, A5, A6, A9, A11, A16, A17, A18.

A most particularly preferably stands for the group A1.

A furthermore most particularly preferably stands for the group A2.

A furthermore most particularly preferably stands for the group A4.

A furthermore most particularly preferably stands for the group A5.

A furthermore most particularly preferably stands for the group A6.

A furthermore most particularly preferably stands for the group A9.

A furthermore most particularly preferably stands for the group A11.

A furthermore most particularly preferably stands for the group A16.

A furthermore most particularly preferably stands for the group A18.

$R^{12}$ stands preferably for hydrogen, cyano, fluorine, chlorine, bromine, iodine, methyl, ethyl, isopropyl, methoxy, ethoxy, methylthio, ethylthio, cyclopropyl, $C_1$-$C_2$ haloalkyl, $C_1$-$C_2$ haloalkoxy in each case with 1 to 5 fluorine, chlorine and/or bromine atoms, trifluoromethylthio, difluoromethylthio, aminocarbonyl, aminocarbonylmethyl or aminocarbonylethyl.

$R^{12}$ stands particularly preferably for hydrogen, fluorine, chlorine, bromine, iodine, methyl, ethyl, isopropyl, monofluoromethyl, monofluoroethyl, difluoromethyl, trifluoromethyl, difluorochloromethyl, trichloromethyl, dichloromethyl, cyclopropyl, methoxy, ethoxy, trifluoromethoxy, trichloromethoxy, methylthio, ethylthio, trifluoromethylthio or difluoromethylthio.

$R^{12}$ stands most particularly preferably for hydrogen, fluorine, chlorine, bromine, iodine, methyl, isopropyl, monofluoromethyl, monofluoroethyl, difluoromethyl, trifluoromethyl, difluorochloromethyl or trichloromethyl.

$R^{12}$ stands especially preferably for methyl, difluoromethyl, trifluoromethyl or 1-fluoroethyl.

$R^{13}$ stands preferably for hydrogen, fluorine, chlorine, bromine, iodine, methyl, ethyl, methoxy, ethoxy, methylthio or ethylthio.

$R^{13}$ stands particularly preferably for hydrogen, fluorine, chlorine, bromine, iodine or methyl.

$R^{13}$ stands most particularly preferably for hydrogen, fluorine, chlorine, or methyl.

$R^{14}$ stands preferably for hydrogen, methyl, ethyl, n-propyl, isopropyl, $C_1$-$C_2$ haloalkyl with 1 to 5 fluorine, chlorine and/or bromine atoms, hydroxymethyl, hydroxyethyl, cyclopropyl, cyclopentyl, cyclohexyl or phenyl.

$R^{14}$ stands particularly preferably for hydrogen, methyl, ethyl, isopropyl, trifluoromethyl, difluoromethyl, hydroxymethyl, hydroxyethyl or phenyl.

$R^{14}$ stands most particularly preferably for hydrogen, methyl, trifluoromethyl or phenyl.

$R^{14}$ stands especially preferably for methyl.

$R^{15}$ and $R^{16}$ stand independently of one another preferably for hydrogen, fluorine, chlorine, bromine, methyl, ethyl or $C_1$-$C_2$ haloalkyl with 1 to 5 fluorine, chlorine and/or bromine atoms.

$R^{15}$ and $R^{16}$ stand independently of one another particularly preferably for hydrogen, fluorine, chlorine, bromine, methyl, ethyl, difluoromethyl, trifluoromethyl, difluorochloromethyl or trichloromethyl.

$R^{15}$ and $R^{16}$ stand independently of one another most particularly preferably for hydrogen, fluorine, chlorine, bromine, methyl, ethyl, difluoromethyl, trifluoromethyl or trichloromethyl.

$R^{15}$ and $R^{16}$ stand especially preferably in each case for hydrogen.

$R^{17}$ stands preferably for fluorine chlorine, bromine, cyano, methyl, ethyl, $C_1$-$C_2$ haloalkyl or $C_1$-$C_2$ haloalkoxy in each case with 1 to 5 fluorine, chlorine and/or bromine atoms.

$R^{17}$ stands particularly preferably for fluorine, chlorine, bromine, cyano, methyl, trifluoromethyl, trifluoromethoxy, difluoromethoxy, difluorochloromethoxy or trichloromethoxy.

$R^{17}$ stands most particularly preferably for fluorine, chlorine, bromine, iodine, methyl, trifluoromethyl or trifluoromethoxy.

$R^{17}$ stands especially preferably for methyl.

$R^{18}$ and $R^{19}$ stand independently of one another preferably for hydrogen, fluorine, chlorine, bromine, methyl, ethyl or $C_1$-$C_2$ haloalkyl with 1 to 5 fluorine, chlorine and/or bromine atoms.

$R^{18}$ and $R^{19}$ stand independently of one another particularly preferably for hydrogen, fluorine, chlorine, bromine, methyl, ethyl, difluoromethyl, trifluoromethyl, difluorochloromethyl or trichloromethyl.

$R^{18}$ and $R^{19}$ stand independently of one another most particularly preferably for hydrogen, fluorine, chlorine, bromine, methyl, ethyl, difluoromethyl, trifluoromethyl or trichloromethyl.

$R^{18}$ and $R^{19}$ stand especially preferably in each case for hydrogen.

$R^{20}$ stands preferably for hydrogen, fluorine, chlorine, bromine, methyl, ethyl or $C_1$-$C_2$ haloalkyl with 1 to 5 fluorine, chlorine and/or bromine atoms.

$R^{20}$ stands particularly preferably for hydrogen, fluorine, chlorine, bromine, iodine, methyl or trifluoromethyl.

$R^{20}$ stands most particularly preferably for methyl.

$R^{21}$ stands-preferably for hydrogen, fluorine, chlorine, bromine, iodine, hydroxy, cyano, $C_1$-$C_4$ alkyl, $C_1$-$C_2$ haloalkyl, $C_1$-$C_2$ haloalkoxy or $C_1$-$C_2$ haloalkylthio in each case with 1 to 5 fluorine, chlorine and/or bromine atoms.

$R^{21}$ stands particularly preferably for hydrogen, fluorine, chlorine, bromine, iodine, hydroxy, cyano, methyl, ethyl, n-propyl, isopropyl, n-butyl, iso-butyl, sec-butyl, tert-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio.

$R^{21}$ stands most particularly preferably for hydrogen, fluorine, chlorine, bromine, iodine, methyl, difluoromethyl, trifluoromethyl or trichloromethyl.

$R^{21}$ stands especially preferably for iodine, methyl, difluoromethyl or trifluoromethyl.

$R^{22}$ stands preferably for fluorine, chlorine, bromine, iodine, hydroxy, cyano, $C_1$-$C_4$ alkyl, methoxy, ethoxy, methylthio, ethylthio, difluoromethylthio, trifluoromethylthio, $C_1$-$C_2$ haloalkyl or $C_1$-$C_2$ haloalkoxy in each case with 1 to 5 fluorine, chlorine and/or bromine atoms.

$R^{22}$ stands particularly preferably for fluorine, chlorine, bromine, iodine, hydroxy, cyano, methyl, ethyl, n-propyl, isopropyl, n-butyl, iso-butyl, sec-butyl, tert-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy.

$R^{22}$ stands most particularly preferably for fluorine, chlorine, bromine, iodine, methyl, trifluoromethyl, difluoromethyl or trichloromethyl.

$R^{23}$ stands preferably for hydrogen, fluorine, chlorine, bromine, iodine, cyano, $C_1$-$C_4$ alkyl, methoxy, ethoxy, methylthio, ethylthio, $C_1$-$C_2$ haloalkyl or $C_1$-$C_2$ haloalkoxy in each case with 1 to 5 fluorine, chlorine and/or bromine atoms, $C_1$-$C_2$ alkylsulfinyl or $C_1$-$C_2$ alkylsulfonyl.

$R^{23}$ stands particularly preferably for hydrogen, fluorine, chlorine, bromine, iodine, cyano, n-propyl, isopropyl, n-butyl, iso-butyl, sec-butyl, tert-butyl, trifluoromethyl, difluorochloromethyl, difluorochloromethyl, trichloromethyl, methoxy, ethoxy, methylthio, ethylthio, trifluoromethoxy, difluoromethoxy, difluorochloromethoxy, trichloromethoxy, methylsulfinyl or methylsulfonyl.

$R^{23}$ stands most particularly preferably for hydrogen, fluorine, chlorine, bromine, iodine, n-propyl, isopropyl, n-butyl, iso-butyl, sec-butyl, tert-butyl, trifluoromethyl, difluoromethyl, trichloromethyl, methylsulfinyl or methylsulfonyl.

$R^{23}$ stands especially preferably for hydrogen.

$R^{24}$ stands preferably for methyl, ethyl or $C_1$-$C_2$ haloalkyl with 1 to 5 fluorine, chlorine and/or bromine atoms.

$R^{24}$ stands particularly preferably for methyl, ethyl, trifluoromethyl, difluoromethyl, difluorochloromethyl or trichloromethyl.

$R^{25}$ stands preferably for methyl or ethyl.

$R^{25}$ stands particularly preferably for methyl.

$Q^1$ stands preferably for S (sulfur), $SO_2$ or $CH_2$.

$Q^1$ stands particularly preferably for S (sulfur) or $CH_2$.

$Q^1$ stands most particularly preferably for S (sulfur).

p stands preferably for 0 or 1.

p stands particularly preferably for 0.

$R^{26}$ stands preferably for methyl, ethyl or $C_1$-$C_2$ haloalkyl with 1 to 5 fluorine, chlorine and/or bromine atoms.

$R^{26}$ stands particularly preferably for methyl, ethyl, trifluoromethyl, difluoromethyl, difluorochloromethyl or trichloromethyl.

$R^{26}$ stands most particularly preferably for methyl, trifluoromethyl, difluoromethyl or trichloromethyl.

$R^{27}$ stands preferably for methyl, ethyl or $C_1$-$C_2$ haloalkyl with 1 to 5 fluorine, chlorine and/or bromine atoms.

$R^{27}$ stands particularly preferably for methyl, ethyl, trifluoromethyl, difluoromethyl, difluorochloromethyl or trichloromethyl.

$R^{27}$ stands most particularly preferably for methyl, trifluoromethyl, difluoromethyl or trichloromethyl.

$R^{28}$ and $R^{29}$ stand independently of one another preferably for hydrogen, fluorine, chlorine, bromine, amino, methyl, ethyl or $C_1$-$C_2$ haloalkyl with 1 to 5 fluorine, chlorine and/or bromine atoms.

$R^{28}$ and $R^{29}$ stand independently of one another particularly preferably for hydrogen, fluorine, chlorine, bromine, methyl, ethyl, trifluoromethyl, difluoromethyl, difluorochloromethyl or trichloromethyl.

$R^{28}$ and $R^{29}$ stand independently of one another most particularly preferably for hydrogen, fluorine, chlorine, bromine, methyl, trifluoroethyl, difluoromethyl or trichloromethyl.

$R^{28}$ and $R^{29}$ stand especially preferably in each case for hydrogen.

$R^{30}$ stands preferably for hydrogen, fluorine, chlorine, bromine, iodine, methyl, ethyl or $C_1$-$C_2$ haloalkyl with 1 to 5 fluorine, chlorine and/or bromine atoms.

$R^{30}$ stands particularly preferably for hydrogen, fluorine, chlorine, bromine, iodine, methyl, ethyl, trifluoromethyl, difluoromethyl, difluorochloromethyl or trichloromethyl.

$R^{30}$ stands most particularly preferably for hydrogen, fluorine, chlorine, bromine, iodine, methyl, trifluoromethyl, difluoromethyl or trichloromethyl.

$R^{30}$ stands especially preferably for methyl.

$R^{31}$ and $R^{32}$ stand independently of one another preferably for hydrogen, fluorine, chlorine, bromine, amino, nitro, methyl, ethyl or $C_1$-$C_2$ haloalkyl with 1 to 5 fluorine, chlorine and/or bromine atoms.

$R^{31}$ and $R^{32}$ stand independently of one another particularly preferably for hydrogen, fluorine, chlorine, bromine, nitro, methyl, ethyl, trifluoromethyl, difluoromethyl, difluorochloromethyl or trichloromethyl.

$R^{31}$ and $R^{32}$ stand independently of one another most particularly preferably for hydrogen, fluorine, chlorine, bromine, methyl, trifluoromethyl, difluoromethyl or trichloromethyl.

$R^{31}$ and $R^{32}$ stand especially preferably in each case for hydrogen.

$R^{33}$ stands preferably for hydrogen, fluorine, chlorine, bromine, methyl, ethyl or $C_1$-$C_2$ haloalkyl with 1 to 5 fluorine, chlorine and/or bromine atoms.

$R^{33}$ stands particularly preferably for hydrogen, fluorine, chlorine, bromine, methyl, ethyl, trifluoromethyl, difluoromethyl, difluorochloromethyl or trichloromethyl.

$R^{33}$ stands most particularly preferably for hydrogen, fluorine, chlorine, bromine, methyl, trifluoromethyl, difluoromethyl or trichloromethyl.

$R^{33}$ stands especially preferably for methyl.

$R^{34}$ stands preferably for hydrogen, fluorine, chlorine, bromine, amino, $C_1$-$C_4$ alkylamino, di($C_1$-$C_4$ alkyl)amino, cyano, methyl, ethyl or $C_1$-$C_2$ haloalkyl with 1 to 5 fluorine, chlorine and/or bromine atoms.

$R^{34}$ stands particularly preferably for hydrogen, fluorine, chlorine, bromine, amino, methylamino, dimethylamino, cyano, methyl, ethyl, trifluoromethyl, difluoromethyl, difluorochloromethyl or trichloromethyl.

$R^{34}$ stands most particularly preferably for hydrogen, fluorine, chlorine, bromine, amino, methylamino, dimethylamino, methyl, trifluoromethyl, difluoromethyl or trichloromethyl.

$R^{34}$ stands especially preferably for amino, methylamino, dimethylamino, methyl or trifluoromethyl.

$R^{35}$ stands preferably for fluorine, chlorine, bromine, methyl, ethyl or $C_1$-$C_2$ haloalkyl with 1 to 5 fluorine, chlorine and/or bromine atoms.

$R^{35}$ stands particularly preferably for fluorine, chlorine, bromine, methyl, ethyl, trifluoromethyl, difluoromethyl, difluorochloromethyl or trichloromethyl.

$R^{35}$ stands most particularly preferably for fluorine, chlorine, bromine, methyl, trifluoromethyl, difluoromethyl or trichloromethyl.

$R^{33}$ stands especially preferably for methyl, trifluoromethyl or difluoromethyl.

$R^{36}$ stands preferably for hydrogen, fluorine, chlorine, bromine, amino, $C_1$-$C_4$ alkylamino, di($C_1$-$C_4$ alkyl)amino, cyano, methyl, ethyl or $C_1$-$C_2$ haloalkyl with 1 to 5 fluorine, chlorine and/or bromine atoms.

$R^{36}$ stands particularly preferably for hydrogen, fluorine, chlorine, bromine, amino, methylamino, dimethylamino, cyano, methyl, ethyl, trifluoromethyl, difluoromethyl, difluorochloromethyl or trichloromethyl.

$R^{36}$ stands most particularly preferably for hydrogen, fluorine, chlorine, bromine, amino, methylamino, dimethylamino, methyl, trifluoromethyl, difluoromethyl or trichloromethyl.

$R^{36}$ stands especially preferably for amino, methylamino, dimethylamino, methyl or trifluoromethyl.

$R^{37}$ stands preferably for fluorine, chlorine, bromine, methyl, ethyl or $C_1$-$C_2$ haloalkyl with 1 to 5 fluorine, chlorine and/or bromine atoms.

$R^{37}$ stands particularly preferably for fluorine, chlorine, bromine, methyl, ethyl, trifluoromethyl, difluoromethyl, difluorochloromethyl or trichloromethyl.

$R^{37}$ stands most particularly preferably for fluorine, chlorine, bromine, methyl, trifluoromethyl, difluoromethyl or trichloromethyl.

$R^{37}$ stands especially preferably for methyl, trifluoromethyl or difluoromethyl.

$R^{38}$ stands preferably for fluorine, chlorine, bromine, methyl, ethyl or $C_1$-$C_2$ haloalkyl with 1 to 5 fluorine, chlorine and/or bromine atoms.

$R^{38}$ stands particularly preferably for fluorine, chlorine, bromine, methyl, ethyl, trifluoromethyl, difluoromethyl, difluorochloromethyl or trichloromethyl.

$R^{38}$ stands most particularly preferably for fluorine, chlorine, bromine, methyl, trifluoromethyl, difluoromethyl or trichloromethyl.

$R^{39}$ stands preferably for hydrogen, methyl or ethyl.

$R^{39}$ stands particularly preferably for methyl.

$R^{40}$ stands preferably for fluorine, chlorine, bromine, methyl or ethyl, $R^{40}$ stands particularly preferably for fluorine, chlorine, or methyl.

$R^{41}$ stands preferably for methyl, ethyl or $C_1$-$C_2$ haloalkyl with 1 to 5 fluorine, chlorine and/or bromine atoms.

$R^{41}$ stands particularly preferably for methyl, ethyl, trifluoromethyl, difluoromethyl, difluorochloromethyl or trichloromethyl.

$R^{41}$ stands most particularly preferably for methyl, trifluoromethyl, difluoromethyl or trichloromethyl.

$R^{41}$ stands especially preferably for methyl or trifluoromethyl.

$R^{42}$ stands preferably for hydrogen, fluorine, chlorine, bromine, methyl, ethyl or $C_1$-$C_2$ haloalkyl with 1 to 5 fluorine, chlorine and/or bromine atoms.

$R^{42}$ stands particularly preferably for hydrogen, fluorine, chlorine, bromine, methyl or trifluoromethyl.

$R^{43}$ stands preferably for fluorine, chlorine, bromine, iodine, hydroxy, $C_1$-$C_4$ alkyl, methoxy, ethoxy, methylthio, ethylthio, difluoromethylthio, trifluoromethylthio, $C_1$-$C_2$ haloalkyl or $C_1$-$C_2$ haloalkoxy in each case with 1 to 5 fluorine, chlorine and/or bromine atoms.

$R^{43}$ stands particularly preferably for fluorine, chlorine, bromine, iodine, methyl, ethyl, n-propyl, isopropyl, n-butyl, iso-butyl, sec-butyl, tert-butyl, trifluoromethyl, difluoromethyl, difluorochloromethyl or trichloromethyl.

$R^{43}$ stands most particularly preferably for fluorine, chlorine, bromine, iodine, methyl, trifluoromethyl, difluoromethyl or trichloromethyl.

$R^{44}$ stands preferably for hydrogen, methyl, ethyl, $C_1$-$C_2$ haloalkyl with 1 to 5 fluorine, chlorine and/or bromine atoms, $C_1$-$C_4$ alkoxy-$C_1$-$C_4$-alkyl, hydroxymethyl, hydroxyethyl, methylsulfonyl or dimethylaminosulfonyl.

$R^{44}$ stands particularly preferably for hydrogen, methyl, ethyl, trifluoromethyl, methoxymethyl, ethoxymethyl, hydroxymethyl or hydroxymethyl.

$R^{44}$ stands most particularly preferably for methyl or methoxymethyl.

$R^{45}$ stands preferably for hydrogen, fluorine, chlorine, bromine, methyl, ethyl or $C_1$-$C_2$ haloalkyl with 1 to 5 fluorine, chlorine and/or bromine atoms.

$R^{45}$ stands particularly preferably for hydrogen, fluorine, chlorine, bromine, methyl, ethyl, trifluoromethyl, difluoromethyl, or trichloromethyl.

$R^{45}$ stands most particularly preferably for hydrogen or methyl.

$R^{46}$ stands preferably for hydrogen, fluorine, chlorine, bromine, iodine, cyano, methyl, ethyl, isopropyl or $C_1$-$C_2$ haloalkyl with 1 to 5 fluorine, chlorine and/or bromine atoms.

$R^{46}$ stands particularly preferably for hydrogen, fluorine, chlorine, bromine, cyano, methyl, ethyl, isopropyl, trifluoromethyl, difluoromethyl, difluorochloromethyl or trichloromethyl.

$R^{46}$ stands most particularly preferably for hydrogen, methyl, difluoromethyl or trifluoromethyl.

$R^{47}$ stands preferably for hydrogen, fluorine, chlorine, bromine, methyl, ethyl or $C_1$-$C_2$ haloalkyl with 1 to 5 fluorine, chlorine and/or bromine atoms.

$R^{47}$ stands particularly preferably for hydrogen, fluorine, chlorine, bromine, iodine, methyl or trifluoromethyl.

$R^{47}$ stands most particularly preferably for hydrogen.

$R^{48}$ stands preferably for methyl, ethyl, n-propyl or isopropyl.

$R^{48}$ stands particularly preferably for methyl or ethyl.

Preferred embodiments are those compounds corresponding to formula (I), in which all groups have the preferred meanings cited above in each case.

Particularly preferred embodiments are those compounds corresponding to formula (I), in which all groups have the particularly preferred meanings cited above in each case.

The following groups of new carboxamides are preferred and each to be considered as a subset of the compounds corresponding to formula (I) cited above:

Group 1: Carboxamides of the formula (I-a)

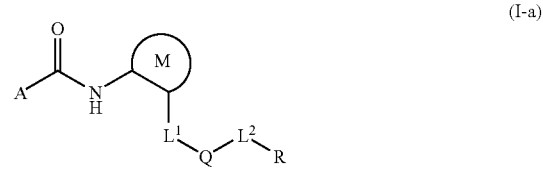

(I-a)

in which M, $L^1$, Q, $L^2$, R and A have the meanings specified above.

Group 2: Carboxamides of the formula (I-b)

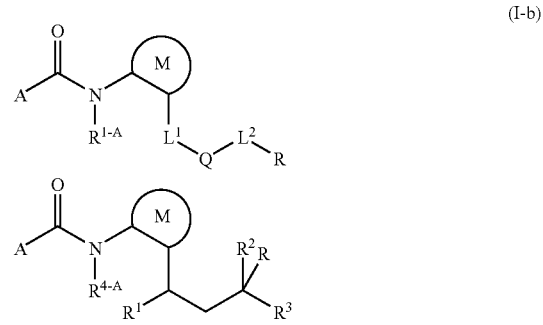

(I-b)

in which $R^{1-A}$, M, $L^1$, Q, $L^2$, R and A have the meanings specified above.

$R^{1-A}$ stands preferably for $C_1$-$C_6$ alkyl, $C_1$-$C_4$ alkylsulfinyl, $C_1$-$C_4$ alkylsulfonyl, $C_1$-$C_3$-alkoxy-$C_1$-$C_3$-alkyl, $C_3$-$C_6$ cycloalkyl; $C_1$-$C_4$ haloalkyl, $C_1$-$C_4$ haloalkylthio, $C_1$-$C_4$ haloalkylsulfinyl, $C_1$-$C_4$ haloalkylsulfonyl, halo-$C_1$-$C_3$-alkoxy-$C_1$-$C_3$-alkyl, $C_3$-$C_8$ halocycloalkyl with 1 to 9 fluorine, chlorine and/or bromine atoms in each case; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl with 1 to 13 fluorine, chlorine and/or bromine atoms in each case; ($C_1$-$C_6$ alkyl)carbonyl, ($C_1$-$C_4$ alkoxy) carbonyl, ($C_1$-$C_3$-alkoxy-$C_1$-$C_3$-alkyl)carbonyl, ($C_3$-$C_6$ cycloalkyl)carbonyl; ($C_1$-$C_4$ haloalkyl)carbonyl, ($C_1$-$C_4$ haloalkoxy)carbonyl, (halo-$C_1$-$C_3$-alkoxy-$C_1$-$C_3$-alkyl)carbonyl, ($C_3$-$C_6$ halocycloalkyl)carbonyl with 1 to 9 fluorine, chlorine and/or bromine atoms in each case; or —C(=O)C(=O)$R^2$, —CONR$^3$R$^4$ or —CH$_2$NR$^5$R$^6$.

$R^{1-4}$ stands particularly preferably for methyl, ethyl, n- or isopropyl, n-, iso-, sec- or tert-butyl, pentyl or hexyl, methylsulfinyl, ethylsulfinyl, n- or isopropylsulfinyl, n-, iso-, sec- or tert-butylsulfinyl, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulfinyl, trifluoromethylsulfonyl, trifluoromethoxymethyl; formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$—CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CO—CCl$_3$, CH$_2$—CO—CH$_2$CF$_3$, —CH$_2$—CO—CH$_2$CCl$_3$, —(CH$_2$)$_2$—CO—CH$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, —CH$_2$—CO$_2$CH$_2$CCl$_3$, —CH$_2$—CO$_2$CCl$_2$CCl$_3$, —(CH$_2$)$_2$—CO$_2$CH$_2$CF$_3$, —(CH$_2$)$_2$—CO$_2$CF$_2$CF$_3$, —(CH$_2$)$_2$—CO$_2$CH$_2$CCl$_3$, —(CH$_2$)$_2$—CO$_2$CCl$_2$CCl$_3$; methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoromethylcarbonyl, trifluoromethoxycarbonyl, or —C(=O)C(=O)R$^2$, —CONR$^3$R$^4$ or —CH$_2$NR$^5$R$^6$.

$R^{1-4}$ stands most particularly preferably for methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

Group 3: Carboxamides of the formula (I-c)

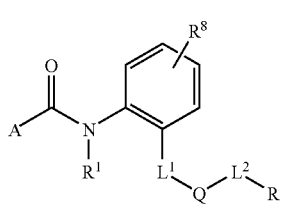

in which R$^1$, R$^8$, L$^1$, Q, L$^2$, R and A have the meanings specified above.

Preferred embodiments are carboxamides of the formula (I-c), in which R$^1$ stands for hydrogen. Preferred embodiments are carboxamides of the formula (I-c), in which R$^8$ stands for hydrogen. Preferred embodiments are carboxamides of the formula (I-c), in which R$^1$ and R$^8$ each stand for hydrogen.

Group 4: Carboxamides of the formula (I-d)

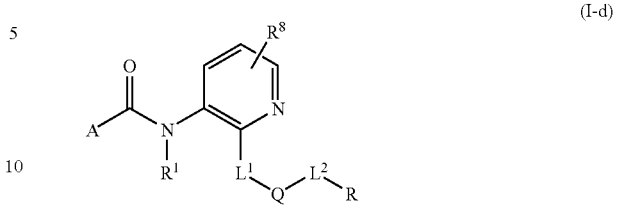

in which R$^1$, R$^8$, L$^1$, Q, L$^2$, R and A have the meanings specified above.

Preferred embodiments are carboxamides of the formula (I-d), in which R$^1$ stands for hydrogen. Preferred embodiments are carboxamides of the formula (I-d), in which R$^8$ stands for hydrogen. Preferred embodiments are carboxamides of the formula (I-d), in which R$^1$ and R$^8$ each stand for hydrogen.

Group 5: Carboxamides of the formula (I-e)

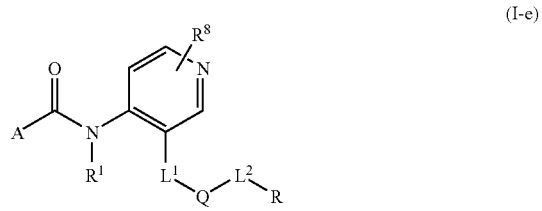

in which R$^1$, R$^8$, L$^1$, Q, L$^2$, R and A have the meanings specified above.

Preferred embodiments are carboxamides of the formula (I-e), in which R$^1$ stands for hydrogen. Preferred embodiments are carboxamides of the formula (I-e), in which R$^8$ stands for hydrogen. Preferred embodiments are carboxamides of the formula (I-e), in which R$^1$ and R$^8$ each stand for hydrogen.

Group 6: Carboxamides of the formula (I-f)

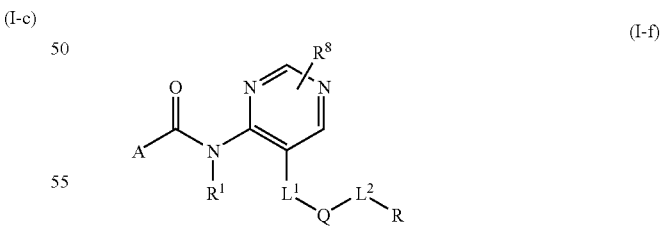

in which R$^1$, R$^8$, L$^1$, Q, L$^2$, R and A have the meanings specified above.

Preferred embodiments are carboxamides of the formula (I-f), in which R$^1$ stands for hydrogen. Preferred embodiments are carboxamides of the formula (I-f), in which R$^8$ stands for hydrogen. Preferred embodiments are carboxamides of the formula (I-f), in which R$^1$ and R$^8$ each stand for hydrogen.

Group 7: Carboxamides of the formula (I-g)

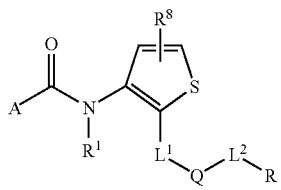

in which $R^1$, $R^8$, $L^1$, Q, $L^2$, R and A have the meanings specified above.

Preferred embodiments are carboxamides of the formula (I-g), in which $R^1$ stands for hydrogen. Preferred embodiments are carboxamides of the formula (I-g), in which $R^8$ stands for hydrogen. Preferred embodiments are carboxamides of the formula (I-g), in which $R^1$ and $R^8$ each stand for hydrogen.

Compounds of the formula (I) (and likewise of the groups 1 to 7), in which $R^1$ stands for hydrogen are emphasized.

Compounds of the formula (I) (and likewise of the groups 1 to 7), in which $R^1$ stands for formyl are emphasized.

Furthermore, compounds of the formula (I) (and likewise of the groups 1 to 7), in which $R^1$ stands for —C(=O)C(=O)$R^2$ are emphasized, whereby $R^2$ has the meanings specified above.

Saturated or unsaturated hydrocarbon groups, such as alkyl or alkenyl, also in combination with hetero atoms, such as, for example, in alkoxy, can each be straight-chained or branched to the extent that is possible. Likewise double-bonded hydrocarbon groups such as alkylene (alkanediyl) can each be straight-chained or branched to the extent that is possible.

Possibly substituted groups can be singly or multiply substituted, whereby with multiple substitutions, the substituents can be the same or varied. Thus the definition "dialkylamino" also includes an asymmetrically substituted amino group, such as, for example, methyl ethyl amino.

Halogen-substituted groups, such as, for example, haloalkyl, are singly or multiply halogenated. With multiple halogenation, the halogen atoms can be the same or different. Halogen in this case stands for fluorine, chlorine, bromine and iodine, particularly for fluorine, chlorine and bromine.

The general or preferential group definitions and/or explanations listed above can be combined arbitrarily between the respective areas and preferential areas. They apply to end products as well as correspondingly to preliminary and intermediate products. Especially the compounds named in the groups 1 to 6 can be combined both with the general as well as the preferred, particularly preferred, etc. definitions, whereby here as well all combinations of the preferred areas are possible in each case.

Description of the Inventive Process for the Synthesis of Hexylcarboxanilides of the Formula (I) as Well as the Intermediate Products Process (a)

If 2-trifluoromethylbenzoyl chloride and {2-[1-(isopropylsulfonyl)ethyl]phenyl}amine are used as starting materials, then the inventive process (a) can be illustrated by the following formula diagram:

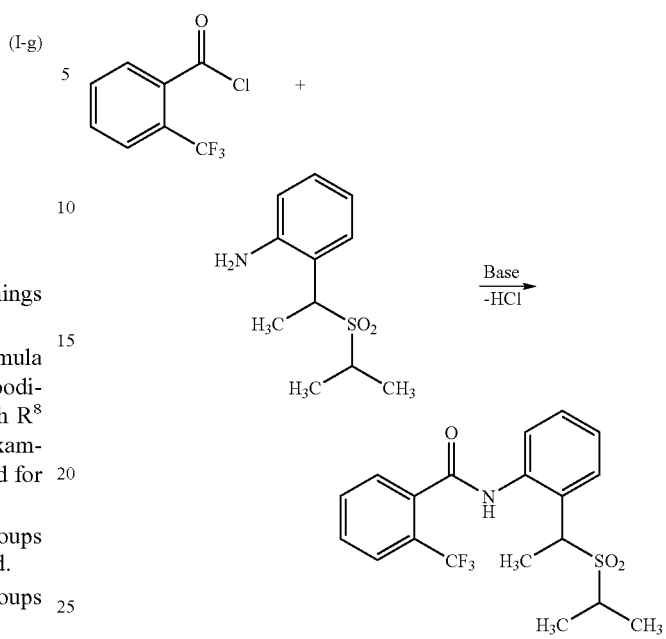

The carboxylic acid derivatives required as starting materials to carry out the inventive process (a) are defined in general by the formula (II). In formula (II), A has the preferred, particularly preferred or most particularly preferred meanings already specified as preferred, particularly preferred or most particularly preferred for A in connection with the description of the inventive compounds according to formula (I). $X^1$ stands preferably for chlorine, bromine or hydroxy.

The carboxylic acid derivatives of the formula (II) are known for the most part and/or maybe synthesized according to known procedures (see WO 93/11117, EP-A 0 545 099, EP-A 0 589 301 and EP-A 0 589 313).

The aniline derivatives further required as starting materials to carry out the inventive process (a) are defined in general by the formula (III). In formula (III), $R^1$, M, Q, $L^2$ and R have the preferred, particularly preferred or most particularly preferred meanings already specified as preferred, particularly preferred or most particularly preferred for these groups in connection with the description of the inventive compounds according to formula (I). $L^3$ stands preferably for hydrogen or $C_1$-$C_5$ alkyl, particularly preferably for hydrogen or methyl.

The aniline derivatives of the formula (III) are new.

Aniline derivatives of the formula (III-a)

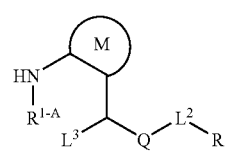

in which $R^{1-A}$, M, Q, $L^2$, R and $L^3$ have the meanings specified above are obtained by reacting (d) aniline derivatives of the formula (III-b)

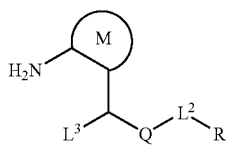
(III-b)

in which M, Q, $L^2$, R and $L^3$ have the meanings specified above, with halides of the formula (VI)

$$R^{1-4}—X^2 \quad (VI)$$

in which $R^{1-4}$ and $X^2$ have the meanings specified above, in the presence of a base and in the presence of a dilution medium.

Aniline derivatives of the formula (III-b) are obtained by reacting
(e) a nitro compound of the formula (VII)

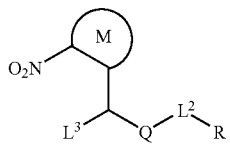
(VII)

in which M, Q, $L^2$, R and $L^3$ have the meanings specified above,
in the presence of a metal and a reducing agent, as well as perhaps in the presence of a diluent and possibly in the presence of a further reaction medium.

The nitro compounds required as starting materials to carry out the inventive process (e) are defined in general by the formula (VII). In formula (VII), M, Q, $L^2$, R and $L^3$ have the preferred, particularly preferred or most particularly preferred meanings already specified as preferred, particularly preferred or most particularly preferred for these groups in connection with the description of the inventive compounds according to formula (I) or (III).

Nitro compounds of the formula (VII) are obtained by reacting
(f) a nitro compound of the formula (VII)

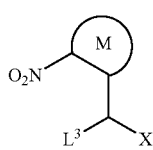
(VII)

in which
M and $L^3$ have the meanings specified above and
X stands for chlorine, bromine or iodine,
with a compound of the formula (IX)

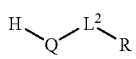
(IX)

In which Q, $L^2$ and R have the meanings specified above, in the presence of a base and possibly in the presence of a dilution medium.

The nitro compounds required as starting materials to carry out the inventive process (f) are defined in general by the formula (VII). In formula (VII), M and $L^3$, have the preferred, particularly preferred or most particularly preferred meanings already specified as preferred, particularly preferred or most particularly preferred for these groups in connection with the description of the inventive compounds according to formula (I) or (III). X stands preferably for chlorine.

The compounds required as starting materials to carry out the inventive process (f) are furthermore defined in general by the formula (IX). In formula (IX) Q, $L^2$ and R have the preferred, particularly preferred or most particularly preferred meanings already specified as preferred, particularly preferred or most particularly preferred for these groups in connection with the description of the inventive compounds according to formula (I) or (III).

Compounds of the formula (IX) are known or can be obtained according to known processes.

Nitro compounds of the formula (VII-a)

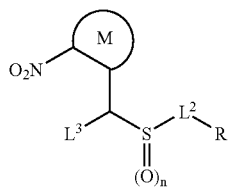
(VII-a)

in which
M, $L^2$, R and $L^3$ have the meanings specified above and
n stands for 1 or 2, are obtained by reacting
(g) a nitro compound of the formula (VII-b)

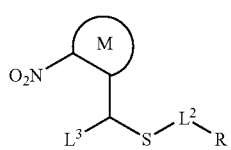
(VII-b)

in which M, $L^2$, R and $L^3$ have the meanings specified above,
in the presence of an oxidizing agent, as well as perhaps in the presence of a diluent and possibly in the presence of a further reaction medium.

Nitro compounds of the formula (VII-c)

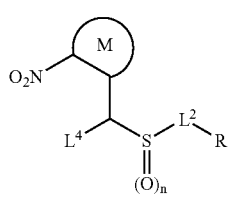
(VII-c)

in which

M, $L^2$, R and n have the meanings specified above and $L^4$ stands for $C_1$-$C_9$ alkyl, preferably for $C_1$-$C_5$ alkyl, particularly preferably for methyl, are obtained by reacting (h) a nitro compound of the formula (VII-d)

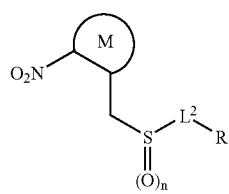
(VII-d)

in which M, $L^2$, R and n have the meanings specified above, with halides of the formula (X)

$L^4$-$X^2$ (X)

in which $L^4$ and $X^2$ have the meanings specified above,
in the presence of a base and in the presence of a dilution medium.

Halides of the formula (X) are known.

The compounds of the formulae (VII-a), (VII-b), (VII-c) and (VII-d) are subgroups of the nitro compounds of the formula (VII) and are included in the general description of these compounds. The preferred, particularly preferred, etc. definitions apply here accordingly. Nitro compounds of the formula (VII) are obtained by halogenating (j) hydroxy derivatives of the formula (XI)

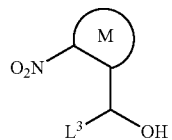
(XI)

in which M and $L^3$ have the meanings specified above,
possibly in the presence of a diluent, possibly in the presence of an acid acceptor and possibly in the presence of a catalyst.

The hydroxy derivatives required as starting materials to carry out the inventive process (j) are defined in general by the formula (XI). In formula (XI), M and $L^3$, have the preferred, particularly preferred or most particularly preferred meanings already specified as preferred, particularly preferred or most particularly preferred for these groups in connection with the description of the inventive compounds according to formula (I) or (III).

Hydroxy derivatives of the formula (XI) are obtained by reacting (k) acylated aromatics of the formula (XII)

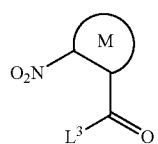
(XII)

in which M and $L^3$ have the meanings specified above,
in the presence of a reducing agent as well as perhaps in the presence of a diluent, possibly in the presence of an acid and possibly in the presence of a catalyst.

Aniline derivatives of the formula (III) can also be obtained in processes analogous to known ones (see EP-A 0 737 682).

Process (b)

If N-[2-(hydroxymethyl)phenyl]-1-methyl-3-(trifluoromethyl)-1H-pyrazole-4-carboxamide and 2-iodopropane are used as starting materials, then the inventive process (b) can be illustrated by the following formula diagram:

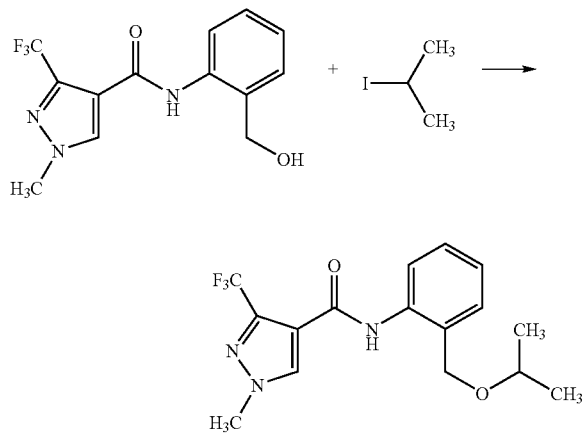

The carboxamides required were as starting materials to carry out the inventive process (b) are defined in general by the formula (IV). In formula (IV), M, $L^1$, Q and A have the preferred, particularly preferred or most particularly preferred meanings already specified as preferred, particularly preferred or most particularly preferred for A in connection with the description of the inventive compounds according to formula (I).

The compounds required as starting materials to carry out the inventive process (b) are furthermore defined in general by the formula (V). In formula (V), $L^2$ and R have the preferred, particularly preferred or most particularly preferred meanings already specified as preferred, particularly preferred or most particularly preferred for A in connection with the description of the inventive compounds according to formula (I). Y stands preferably for chlorine, bromine, iodine, triflate (trifluoromethylsulfonyl), mesylate (methylsulfonyl) or tosylate (4-methylphenylsulfonyl), particularly preferably for bromine, iodine or triflate (trifluoromethylsulfonyl).

Compounds of the formula (V) are known or can be obtained according to known processes. Carboxamides of the formula (IV) are new. They are obtained by reacting (m) carboxylic acid derivatives of the formula (II)

(II)

in which

A has the meanings specified above and $X^1$ stands for halogen or hydroxy, with aniline derivatives of the formula (XIII)

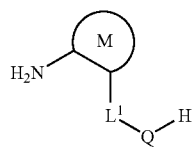

(XIII)

in which M, $L^1$ and Q have the meanings specified above, possibly in the presence of a catalyst, possibly in the presence a condensation agent, possibly in the presence of an acid binder and possibly in the presence of a diluent.

The carboxylic acid derivatives of the formula (II), required as starting materials for the implementation of the inventive process (m), have already been described in connection with the inventive process (a).

The aniline derivatives further required as starting materials to carry out the inventive process (m) are defined in general by the formula (XIII). In formula (XIII), M, $L^1$ and Q have the preferred, particularly preferred or most particularly preferred meanings already specified as preferred, particularly preferred or most particularly preferred for these groups in connection with the description of the inventive compounds according to formula (I).

Aniline derivatives of the formula (XIII) are known or can be obtained according to known processes.

Process (c)

If 3-(difluoromethyl)-N-{2-[(isopropylthio)methyl]phenyl}-1-methyl-1H-pyrazole-4-carboxamide and ethyl-chloo(oxo)acetate are used as starting materials, then the course of the inventive process (c) can be illustrated by the following formula diagram:

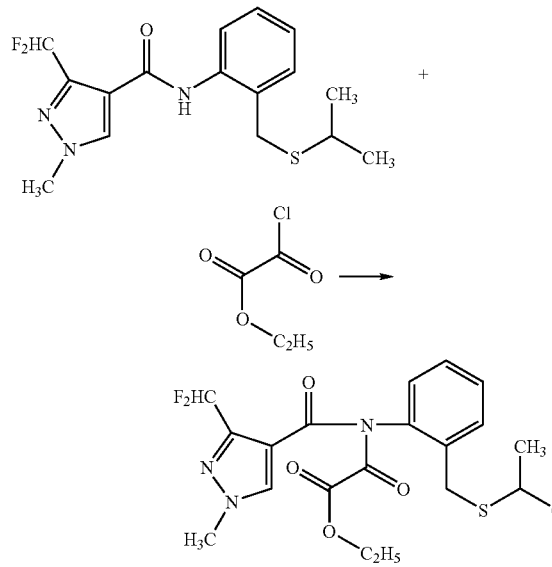

The hexylcarboxanilides required as starting materials to carry out the inventive process (c) are defined in general by the formula (I-a). In formula (I-a) M, $L^1$, Q, $L^2$, R and A have the preferred, particularly preferred or most particularly preferred meanings already specified as preferred, particularly preferred or most particularly preferred for A in connection with the description of the inventive compounds according to formula (I).

The hexylcarboxanilides of the formula (I-a) are likewise inventive compounds and subjects of this application. They can be obtained according to the inventive process (a) (with $R^1$=hydrogen).

The halides required as starting materials to carry out the inventive process (c) are defined in general by the formula (VI). In this formula (VI), $R^{1-4}$ has the preferred, particularly preferred or most particularly preferred meanings already specified as preferred, particularly preferred or most particularly preferred for this group in connection with the description of the inventive compounds according to formula (I-b). $X^2$ stands preferably for chlorine or bromine.

Halides of the formula (VI) are known.

Reaction Conditions

All inert organic solvents can be considered as diluents for carrying out the inventive processes (a) and (m). This preferably includes aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloromethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole or amides, such as N,N-dimethyl formamide, N,N-dimethyl acetamide, N-methylformanilide, N-methyl pyrrolidone or hexamethyl phosphoric acid triamide.

The inventive processes (a) and (m) are carried out in the presence of a suitable acid acceptor as needed. All common inorganic or organic bases can be used as such. These include preferably alkaline earth metal hydrides or alkali metal hydrides, hydroxides, amides, alkoxides, acetates, carbonates or hydrogen carbonates, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, as well as tertiary amines, such as trimethylamine, trimethylamine, tributylamine, N,N-dimethylaniline, N,N-dimethyl benzyl amine, pyridine, N-methyl piperidine, N-methyl morpholine, N,N-dimethylaminopyridine, diazabicyclooctane (DABCO), diazabicyclononene (DBN) or diazabicycloundecene (DBU).

The inventive processes (a) and (m) are carried out in the presence of a suitable condensation agent as needed. Condensation agents to be considered are those typically used for such amidation reactions. Named as examples are reagents that form acid halides, such as phosgene, phosphorus tribromide, phosphorus trichloride, phosphorus pentachloride, phosphorus oxychloride, oxalyl chloride or thionyl chloride; reagents that form anhydrides such as chloroformic acid ethyl ester, chloroformic acid methyl ester, chloroformic acid isopropyl ester, chloroformic acid isobutyl ester or methane sulfonyl chloride; carbodiimides, such as N,N'-dicyclohexylcarbodiimide (DCC) or other common condensation agents, such as phosphorus pentoxide, polyphosphoric acid, N,N'-carbonyldiimidazole, 2-ethoxy-1-ethoxycarbonyl-1,2-dihydroquinoline (EEDQ), triphenylphosphine/tetrachloromethane or bromotripyrrolidinophosphonium hexafluorophosphate.

The inventive processes (a) and (in) are carried out in the presence of a catalyst as needed. Named as examples are 4-dimethylaminopyridine, 1-hydroxybenzotriazole or dimethyl formamide.

In carrying out the inventive processes (a) and (in), the reaction temperatures can be varied over a wide range. Generally one works at temperatures of 0° C. to 150° C., preferably at temperatures of 0° C. to 80° C.

To carry out the inventive process (a) for the synthesis of compounds of the formula (I), generally 0.2 to 5 mols, preferably 0.5 to 2 mols, of an aniline derivative of the formula (III) are used per mol of the carboxylic acid derivative of the formula (II).

To carry out the inventive process (m) for the synthesis of compounds of the formula (IV), generally 0.2 to 5 mols, preferably 0.5 to 2 mols, of an aniline derivative of the formula (XIII) are used per mol of the carboxylic acid derivative of the formula (II).

All inert organic solvents can be considered as diluents for carrying out the inventive processes (b), (c), (d) and (h). This preferably includes aliphatic, alicyclic or aromatic hydrocarbons, such as, for example, petroleum ether, hexane, heptane, cyclohexane, methylcyclohexane, benzene, toluene, xylene or decalin; halogenated hydrocarbons, Such as, for example, chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole or amides, such as N,N-dimethyl formamide, N,N-dimethyl acetamide, N-methylformanilide, N-methyl pyrrolidone or hexamethyl phosphoric acid triamide.

The inventive processes (b), (c), (d) and (h) are carried out in the presence of a base. All common inorganic or organic bases can be used for this purpose. These include preferably alkaline earth metal hydrides or alkali metal hydrides, hydroxides, amides, alkoxides, acetates, carbonates or hydrogen carbonates, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or cesium carbonate, as well as tertiary amities, such as trimethylamine, triethylamine, tributylamine, N,N-dimethylaniline, N,N-dimethyl benzyl amine, pyridine, N-methyl piperidine, N-methyl morpholine, N,N-dimethylaminopyridine, diazabicyclooctane (DABCO), diazabicyclononene (DBN) or diazabicycloundecene (DBU).

In carrying out the inventive processes (b), (c), (d) and (h), the reaction temperatures can be varied over a wide range. Generally one works at temperatures of 0° C. to 150° C., preferably at temperatures of 20° C. to 110° C.

To carry out the inventive process (b) for the synthesis of compounds corresponding to formula (I), generally 0.2 to 5 mols, preferably 0.5 to 2 mols, of a compound of the formula (V) are used per mol of the carboxamide of the formula (IV).

To carry out the inventive process (c) for the synthesis of compounds corresponding to formula (I), generally 0.2 to 5 mols, preferably 0.5 to 2 mols, of a halide of the formula (VI) are used per mol of the hexylcarboxanilide of the formula (I-a).

To carry out the inventive process (d) for the synthesis of compounds of the formula (III-a), generally 0.2 to 5 mols, preferably 0.5 to 2 mols, of a halide of the formula (VI) are used per mol of the aniline derivative of the formula (III-b).

To carry out the inventive process (h) for the synthesis of compounds of the formula (VII-c), generally 0.2 to 5 mols, preferably 0.5 to 2 mols, of a halide of the formula (X) are used per mol of the nitro compound of the formula (VII-d).

All inert organic solvents can be considered as diluents for carrying out the inventive process (e). This preferably includes aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; amides, such as N,N-dimethyl formamide, N,N-dimethyl acetamide, N-methylformanilide, N-methyl pyrrolidone or hexamethyl phosphoric acid triamide; sulfoxides, such as dimethyl sulfoxide; sulfones, such as sulfolan; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, triethylene glycol, their mixtures with water or pure water.

The inventive process (e) is carried out in the presence of a metal. Preference is given here to transition metals, such as, for example, palladium, platinum, rhodium, nickel (Raney nickel), iron, cobalt, ruthenium, iridium, zinc or osmium. The metals can be bound to a substrate as needed, such as, for example, carbon, resins, zeolites, alkali or alkaline earth sulfates.

The inventive process (e) is carried out in the presence of a reducing agent. Materials preferred for this are elemental hydrogen, formate salts, preferably alkali formate salts, such as, for example sodium formate, but also ammonium formate or also metal hydrides or complex metal hydrides, such as, for example, lithium aluminum hydride and sodium borohydride.

The inventive process (e) can be carried out in the presence of acids. Materials preferred for this are organic acids, such as, for example, formic acid, acetic acid, ascorbic acid, but also inorganic acids, such as, for example, hydrochloric acid or sulfuric acid.

The inventive process (e) can be carried out in the presence of bases. Materials preferred for this are organic bases, such as, for example, pyridine, aber also aqueous solutions of alkali or alkaline earth metal hydroxides, such as, for example, sodium hydroxide or barium hydroxide.

In carrying out the inventive process (e), the reaction temperatures can be varied over a wide range. Generally one works at temperatures of −80° C. to 300° C., preferably at temperatures of 0° C. to 200° C.

With the use of elemental hydrogen, the inventive process (e) is carried out in hydrogen pressure between 0.5 and 200 bar, preferably between 1 and 100 bar.

To carry out the inventive process (e) for the synthesis of compounds of the formula (III-b), generally 0.8 to 1000 mols, preferably 1 to 500 mols, of a reducing agent (ammonium formate, hydride, etc.) are used per mol of a nitro compound of the formula (VII).

All inert organic solvents can be considered as diluents for carrying out the inventive process (f). This preferably includes aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2- dimethoxyethane, 1,2-diethoxyethane or anisole or amides, such as N,N-dimethyl formamide, N,N-dimethyl acetamide, N-methylformanilide, N-methyl pyrrolidone or hexamethyl phosphoric acid triamide.

The inventive process (f) is carried out in the presence of a base. All common inorganic or organic bases can be used for this purpose. These include preferably alkaline earth metal hydrides or alkali metal hydrides, hydroxides, amides, alkoxides, acetates, carbonates or hydrogen carbonates, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodiums carbonate, potassium carbonate, potassium hydrogen carbonate, sodium hydrogen carbonate or cesium carbonate, as well as tertiary amines, such as trimethylamine, triethylamine, tributylamine, N,N-dimethylaniline, N,N-dimethyl benzyl amine, pyridine, N-methyl piperidine, N-methyl morpholine, N,N-dimethylaminopyridine, diazabicyclooctane (DABCO), diazabicyclononene (DBN) or diazabicycloundecene (DBU).

In carrying out the inventive process (f), the reaction temperatures can be varied over a wide range. Generally one works at temperatures of 0° C. to 200° C., preferably at temperatures of 20° C. to 140° C.

To carry out the inventive process (f) for the synthesis of compounds of the formula (VII), generally 0.2 to 5 mols, preferably 0.5 to 2 mols, of a compound of the formula (IX) are used per mol of the nitro compound of the formula (VI).

All inert organic solvents can be considered as diluents for carrying out the inventive process (g). This preferably includes aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; amides, such as N,N-dimethyl formamide, N,N-dimethyl acetamide, N-methylformanilide, N-methyl pyrrolidone or hexamethyl phosphoric acid triamide; sulfoxides, such as dimethyl sulfoxide; sulfones, such as sulfolan.

The inventive process (g) is carried out in the presence of an oxidizing agent. All organic and inorganic oxidizing agents can be used here, preferably elemental oxygen, ozone, peroxides, such as, for example, hydrogen peroxide, m-chloroperbenzoic acid, benzoyl peroxide, tert-butyl peroxide; sodium hypochlorite; chromium salts such as, for example, chromium (VI) oxide, chromic acid, sodium dichromate, pyridinium chlorochromate; manganese salts, such as, for example, potassium permanganate, manganese dioxide; selenium dioxide; iodates and periodates; potassium peroxodisulfate.

The inventive process (g) can be carried out in the presence of acids. Materials preferred for this are organic acids, such as, for example, formic acid, acetic acid, ascorbic acid, but also inorganic acids, such as, for example, hydrochloric acid or sulfuric acid.

The inventive process (g) can be carried out in the presence of bases. Materials preferred for this are organic bases, such as, for example, pyridine, aber also aqueous solutions of alkali or alkaline earth metal hydroxides, such as, for example, sodium hydroxide or barium hydroxide.

In carrying out the inventive process (g), the reaction temperatures can be varied over a wide range. Generally one works at temperatures of −80° C. to 300° C., preferably at temperatures of 20° C. to 100° C.

To carry out the inventive process (g) for the synthesis of compounds of the formula (VII-a), generally 0.6 to 10 mols, preferably 0.8 to 5 mols, of an oxidizing agent are used per mol of the nitro compound of the formula (VII-b).

All inert organic solvents can be considered as diluents for carrying out the inventive process (j). This preferably includes aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole or amides, such as N,N-dimethyl formamide, N,N-dimethyl acetamide, N-methylformanilide, N-methyl pyrrolidone or hexamethyl phosphoric acid triamide.

The inventive process (j) is carried out in the presence of a suitable acid acceptor as necessary. All common inorganic or organic bases can be used for this purpose. These include preferably alkaline earth metal hydrides or alkali metal hydrides, hydroxides, amides, alkoxides, acetates, carbonates or hydrogen carbonates, such as, for example, sodium hydride, sodium amide, sodium methylate, sodium ethylate, potassium tert-butylate, sodium hydroxide; potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, as well as tertiary amines, such as trimethylamine, triethylamine, tributylamine, N,N-dimethylaniline, N,N-dimethyl benzyl amine, pyridine, N-methyl piperidine, N-methyl morpholine, N,N-dimethylaminopyridine, diazabicyclooctane (DABCO), diazabicyclononene (DBN) or diazabicycloundecene (DBU).

The inventive process (j) is carried out in the presence of a suitable halogenating agent. Halogenating agents to be considered are those typically used for such halogenation reactions. As examples named are reagents that form halides, such as phosgene, phosphorus tribromide, phosphorus trichloride, phosphorus pentachloride, phosphorus oxychloride, oxalyl chloride or thionyl chloride; reagents that form anhydrides such as chloroformic acid ethyl ester, chloroformic acid methyl ester, chloroformic acid isopropyl ester, chloroformic acid isobutyl ester or methane sulfonyl chloride; or other common condensation agents, such as phosphorus pentoxide, polyphosphoric acid, N,N'-carbonyldiimidazole, 2-ethoxy-1-ethoxycarbonyl-1,2-dihydroquinoline (EEDQ), triphenylphosphine/tetrachloromethane or bromotripyrrolidinophosphonium hexafluorophosphate.

The inventive process (j) is carried out in the presence of a catalyst as necessary. Named as examples are 4-dimethylaminopyridine, 1-hydroxybenzotriazole or dimethyl formamide.

In carrying out the inventive process (j), the reaction temperatures can be varied over a wide range. Generally one works at temperatures of 0° C. to 200° C., preferably at temperatures of 0° C. to 150° C.

To carry out the inventive process (g) for the synthesis of compounds of the formula (VII), generally 0.2 to 10 mols, preferably 0.5 to 5 mols, of a halogenating agent are used per mol of a hydroxy derivative of the formula (XI).

All inert organic solvents can be considered as diluents for carrying out the inventive process (k). This preferably includes aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole or amides, such as N,N-dimethyl formamide, N,N-dimethyl acetamide, N-methylformanilide, N-methyl pyrrolidone or hexamethyl phosphoric acid triamide; alcohols, such as methanol, ethanol, isopropanol.

The inventive process (k) is carried out in the presence of a suitable reducing agent. All common inorganic or organic reducing agents can be used for this purpose. These include preferably alkaline earth metal or alkali metal hydrides, such as, for example, sodium hydride, or complex hydrides, such as, for example, lithium aluminum hydride, sodium borohydride, sodium cyanoborohydride, diisobutyl aluminium hydride, borane, diborane or borane complexes, such as, for example, borane-pyridine, silanes, such as, for example, triethylsilane, metals, such as, for example, sodium, lithium, zinc, iron, or hydrogen.

The inventive process (k) is carried out in the presence of a suitable acid or Lewis acid. All the typical acids/Lewis acids used for such acid-/Lewis acid-mediated reductions can be used. Named as examples are hydrochloric acid, acetic acid, trifluoroacetic acid, boron trifluoride or complexed boron trifluoride, such as, for example, boron trifluoride etherate, aluminum trichloride, cerium trichloride, inorganic or organic titanium compounds, such as, for example, titanium tetrachloride, titanium tetraisopropylate.

The inventive process (k) is carried out in the presence of a catalyst as necessary. Named as examples are metals or metal salts, especially transition metals or their salts, such as, for example, platinum, palladium, nickel (Raney nickel), iridium, rhodium, osmium, iron, ruthenium, cobalt. These metals or metal salts can also be bound or applied to resins or surfaces or substrate materials (such as carbon).

In carrying out the inventive process (k), the reaction temperatures can be varied over a wide range. Generally one works at temperatures of 0° C. to 200° C., preferably at temperatures of 0° C. to 150° C.

With the use of hydrogen as a reducing agent in the inventive process (k), the pressure can be varied over a greater range. In general one works at pressures of 1 bar to 300 bar, preferably at 1 bar to 100 bar.

To carry out the inventive process (k) for the synthesis of compounds of the formula (XI), generally 0.2 to 10 mols, preferably 0.5 to 5 mols, of a reducing agent are used per mol of an acylated aromatic of the formula (XII).

Unless otherwise specified, all inventive processes are generally carried out at normal pressure. However, is also possible to work under increased or reduced pressure—generally between 0.1 bar and 10 bar.

The inventive materials show strong microbicidal activity and can be used to combat undesired microorganisms, such as fungi and bacteria, in crop protection and material protection.

Fungicides can be used in crop protection to combat *Plasmodiophoromycetes, Oomycetes, Chytridiomycetes, Zygomycetes, Ascomycetes, Basidiomycetes* and *Deuteromycetes*.

Bactericides can be used in crop protection to combat *Pseudomonadaceae, Rhizobiaceae, Enterobacteriaceae, Corynebacteriaceae* and *Streptomycetaceae*.

Examples of some pathogens of fungal and bacterial diseases that fall under the superordinate terms listed above include, but are not limited to:

*Xanthomonas* species, such as, for example, *Xanthomonas canipestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Perondspora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea* (conidia form: *Drechslera*, syn: *Helminthosporium*);

*Cochliobolus* species, such as, for example, *Cochliobolus sativus* (conidia form: *Drechslera*, syn: *Helminthosporium*);

*Uromyces* species, such as, for example, *Uromyces appendiculatus;*

*Puccinia* species, such as, for example, *Puccinia recondita;*

*Sclerotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Alternaria* species, such as, for example, *Alternaria brassicae;*

*Pseudocercosporella* species, such as, for example, *Pseudocercosporella herpotrichoides,*

*Rhizoctonia* species, such as, for example, *Rhizoctonia solani.*

The inventive active substances also show a considerable strengthening effect in plants. Thus they are suited for mobilization of the plants' own defenses against infestation by undesirable microorganisms.

In the present context, plant-strengthening (resistance-inducing) materials are to be considered those substances that are able to stimulate the immune system of plants such that the plants treated show extensive resistance against undesired microorganisms when subsequently inoculated with these microorganisms.

In the present context, undesired microorganisms are to be understood as phytopathogenic fungi, bacteria and viruses. The inventive materials can also be used to protect plants against infestation by the pathogens cited for a certain period after treatment. The period during which this protection is provided generally lasts from one to 10 days, preferably one to seven days after treatment of the plants with the active substances.

The active substances show good compatibility with plants at the concentrations needed to combat plant diseases, enabling treatment of above-ground plant parts, plant seed stock and soil.

In this regard, the inventive active substances can be used with particularly good success to combat diseases of grain, such as, for example, those caused by *Puccinia* species, and of diseases in the vinoculture, fruit and vegetable farming, such as, for example, those caused by *Botrytis, Venturia* or *Alternaria* species.

The inventive active substances are also suited for increasing harvest yields. Furthermore, they have low toxicity and show good compatibility with plants.

If necessary, at particular concentrations and application rates, the inventive active substances can also be used as herbicides, influencers of plant growth, as well as to fight animal pests. They can also be used as intermediates and starting products for synthesizing other active substances.

All plants and plant parts can be treated in accordance with the invention. As plants in this context, all plants and plant populations are meant, such as desirable wild plants and undesired wild plants (weeds) or cultured plants (including natural occurring cultured plants). Cultured plants can be plants that can be obtained through conventional breeding and optimization methods or through methods of biotechnology and gene technology or a combination of these methods, including transgenic plants and including those plant types which may be eligible or not be eligible for plant variety protection under law. Plant parts should be understood as all above-ground and subterranean parts and organs of plants, such as sprout, leaf, flower and root, whereby, for example, leaves, needles, stalks, stems, flowers, fruiting bodies, fruits and seeds as well as roots, tubers and rhizomes are listed. Plant parts also include harvest product as well as vegetative and generative propagation material, such as cuttings, tubers, rhizomes, scions and seeds.

The treatment of plants and plant parts with the active substances in accordance with the invention is done directly or by acting on their environment, habitat or storage space by conventional treatment methods, such as by immersion, spraying, vapor exposure, fogging, scattering, spreading and by propagation material, particularly seeds, furthermore by single or multi-layered coverage.

In material protection, the inventive materials can be used to protect technical materials against infestation and destruction by undesirable microorganisms.

Technical materials in this context are to be understood as non-living materials for use in technology. For example, technical materials that are to be protected from microbial change or destruction by active substances according to the invention can be adhesives, glues, paper and cardboard, textiles, leather, wood, paints and plastic articles, cooling lubricants and other materials that can be infested or destroyed by microorganisms. Parts of production systems that can be adversely affected by an increase of microorganisms, Such as cooling water circuits, also fall within the scope of materials to be protected. Technical materials within the scope of the present invention include preferably adhesives, glues, papers and cardboards, leather, wood, paints, cooling lubricants and heat transfer fluids, particularly preferably wood.

Microorganisms that can effect degradation or a change in technical materials include, for example, include bacteria, fungi, yeasts, algae and slime organisms. The inventive active substances act preferentially against fungi, especially molds, wood-discoloring and wood-destroying fungi (*Basidiomycetes*) as well as against slime organisms and algae.

The following genuses of microorganisms are named as examples:

*Alternaria*, such as *Alternaria tenuis*,

*Aspergillus*, such as *Aspergillus niger*,

*Chaetomium*, such as *Chaetomium globosum*,

*Coniophora*, such as *Coniophora puetana*,

*Lentinus*, such as *Lentinus tigrinus*,

*Penicillium*, such as *Penicillium glaucum*,

*Polyporus*, such as *Polyporus versicolor*,

*Aureobasidium*, Such as *Aureobasidium pullulans*,

*Sclerophoma*, such as *Sclerophoma pityophila*,

*Trichoderma*, such as *Trichoderma viride*,

*Escherichia*, such as *Escherichia coli*,

*Pseudomonas*, such as *Pseudomonas aeruginosa*,

*Staphylococcus*, such as *Staphylococcus aureus*.

The active substances can be compounded, depending on their particular physical and/or chemical properties, in typical formulations, such as solutions, emulsions, suspensions, powders, foams, pastes, granulates, aerosols, microencapsulations in polymeric materials and in coatings for seeds, as well as ultra-low volume cold and warm fog formulations.

These formulations are produced according to known methods, such as by mixing the active substances with extenders, i.e. liquid solvents, pressurized, liquified gases and/or solid carrier materials, if necessary with the use of surface-active materials, i.e. emulsifiers and/or dispersing agents and/or foam-producing materials. In the case that water is used as an extender, organic solvents can also be used as solubility aids for example. The following liquid solvents are the main ones to be considered: aromatics, such as xylene, toluene or alkyl naphthalene, chlorinated aromatics or chlorinated aliphatic hydrocarbons, such as chlorobenzenes, chloroethylenes or methylene chloride, aliphatic hydrocarbons, such as cyclohexane or paraffins, such as petroleum fractions, alcohols, such as butanol or glycol as well as their ethers and esters, ketones, such as acetone, methyl ethyl ketone, methyl isobutyl ketone or cyclohexanone, strongly polar solvents, such as dimethyl formamide and dimethyl sulfoxide, as well as water. Liquified gas extenders or carriers are liquids that are gases at normal temperature and normal pressure, for example aerosol propellants, such as halogenated hydrocarbons, as well as butane, propane, nitrogen and carbon dioxide. Solid carrier materials to be considered are, for example, natural mineral powders, such as kaolines, clays, talc, chalk, quartz, attapulgite, montmorillonite or diatomaceous earth and synthetic mineral powders, such as highly disperse silica, aluminum oxide and silicates. Solid carriers to be considered for granulates are, for example, crushed and fractionated natural minerals such as calcite, pumice, marble, sepiolite, dolomite as well as synthetic granulates from inorganic and organic powders as well as granulates from organic material such as sawdust, Coconut shells, corn cobs and tobacco stalks. Emulsifiers and/or foam-producing materials to be considered are, for example, non-ionizable and anionic emulsifiers, such as polyoxyethylene-fatty acid esters, polyoxyethylene-fatty alcohol ethers, such as alkyl aryl polyglycol ethers, alkyl sulfonates, alkyl sulfates, aryl sulfonates as well as protein hydrolysates. Dispersing agents to be considered are, for example, lignin, sulfite waste liquors and methyl cellulose.

Formulations can also include bonding agents like carboxymethyl cellulose, natural and synthetic polymers in powdered, granular or latex-like form, such as gum arabic, polyvinyl alcohol, polyvinyl acetate, as well as natural phospholipids, such as cephalins and lecithins, and synthetic phospholipids. Other additives can be mineral and vegetable oils.

Dyes, such as inorganic pigments, for example iron oxide, titanium oxide, Prussian blue and organic dyes, such as alizarin, azo and metal phthalocyanine dyes and trace elements, such as salts of iron, manganese, boron, copper, cobalt, molybdenum and zinc can be used.

The formulations usually contain between 0.1 and 95 weight percent of the active substance, preferably between 0.5 and 90%.

The inventive active substances can be used as such or in their formulations, also mixed with known fungicides, bactericides, akacaricides, nematicides or insecticides, in order, for example, to increase the spectrum of effectiveness or prevent the development of resistances. In many cases, synergistic effects are achieved, i.e. the effectiveness of the mixture is greater than the effectiveness of the individual components.

Examples of complementary formulation components include the following.

Fungicides 2-phenylphenol; 8-hydroxyquinoline sulfate; acibenzolar-S-methyl; aldimorph; amidoflumet; ampropylfos; ampropylfos-potassium; andoprim; anilazine; azaconazole; azoxystrobin; benalaxyl; benalaxyl-M; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butyl amine; calcium polysulfide; capsimycin; captafol; captan; carbendazim; carboxin; carpropamide; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; idpyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenihexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine albesilate; iodocarb; ipconazole; iprobenfos; iprodione; iprovalicarb; irumamycin; isoprothiolane; isovaledione; kasugamycin; kresoximmethyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrinie; quinconazole; quinoxyfen; quintozene; simeconazole; spiroxamime; sulfur; tebuconazole; tecloftalam; tecnazene; tetcyclacis; tetraconazole; thiabenidazole; thicyofen; thifluzamide; thiophanate-methyl; thiram; tioxymnid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validaimycin A; vinclozolin; zineb; ziram; zoxamide; (2S)-N-[2-[4-[[3-(4-chlorophenyl)-2-propinyl]oxy]-3-methoxyphenyl]ethyl]-3-methyl-2-[(methylsulfonyl)amino]-butanamide; 1-(1-naphthalenyl)-1H-pyrrole-2,5-dione; 2,3,5,6-tetrachloro-4-(methylsulfonyl)-pyridine; 2-amino-4-methyl-N-phenyl-5-thiazolecarboxamide; 2-chloro-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)-cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)-cyclopropanecarboxamide; N-butyl-8-(1,1-dimethylethyl)-1-oxaspiro[4.5]decan-3-amine; sodium tetrathiocarbonate; as well as copper salts and preparations, such as Bordeaux mixture, copper hydroxide, copper naphthenate, copper oxychloride, copper sulfate, cufraneb, copper oxide, mancopper and oxine copper.

Bactericides

Bronopol, dichlorophen; nitrapyrin, nickel dimethyldithiocarbamate, kasugamycin, octhilinone, furancarboxylic acid, oxytetracycline, probenazole, streptomycin, tecloftalam, copper sulfate and other copper preparations.

Insecticides/Akacaricides/Nematicides

1. Acetylcholine Esterase (AChE) Inhibitors 1.1 Carbamates (such as alanycarb, aldicarb, aldoxycarb, allyxycarb, aminocarb, azamethiphos, bendiocarb, benfuracaib, bufencarb, butacarb, butocarboxim, butoxycarbonyl, carbaryl, carbofuran, carbosulfan, chloethocarb, coumaphos, cyanofenphos, cyanophos, dimetilan, ethiofencarb, fenobucarb, fenothiocarb, formetanate, furathiocarb, Isoprocarb, metals-sodium, methiocarb, methomyl, metolcarb, oxamyl, pirimicarb, promecarb, propoxur, thiodicarb, thiofanox, triazamate, trimethacarb, XMC and xylylcarb)

1.2 Organophosphates (such as acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl, -ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylviniphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl o-salicylate, isoxathion, malathion, mecarbam, methacrifos, methamidophos, methidathion, mevinphos, monocrotophos, naled, omethoate, oxydemeton-methyl, parathion (-methyl, -ethyl), phenthoate, phorate, phosalone, phosmet, phosphamidon, phosphocarb, phoxim, pirimiphos (-methyl, -ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)

2. Sodium Channel Modulators/Voltage-Dependent Sodium Channel Blockers
　　2.1 Pyrethroids (such as acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralomethrin, transfluthrin, ZXI 8901, pyrethrins (pyrethrum)
　　2.2 Oxadiazines (such as indoxacarb)

3. Acetylcholine Receptor Agonists/Antagonists
　　3.1 Chloronicotinyls/Neonicotinoides (Such as Acetamiprid, Clothianidin, Dinotefuran, Imidacloprid, Nitenpyram, Nithiazine, Thiacloprid, Thiamethoxam)
　　3.2 Nicotine, Bensultap, Cartap 4. Acetylcholine Receptor Modulators
　　4.1 Spinosyns (Such as Spinosad)

5. GABA-Controlled Chloride Channel Antagonists
　　5.1 Cyclodiene Organochlorine (such as Camphechlor, Chlordane, Endosulfan, Gamma-HCH, HCH, Heptachlor, Lindane, Methoxychlor)
　　5.2 Fiprols (such as Acetoprole, Ethiprole, Fipronil, Vaniliprole)

6. Chloride Channel Activators
　　6.1 Mectins (such as Abamectin, Avermectin, Emamectin, Emamectin-Benzoate, Ivermectin, Milbemectin, Milbemycin)

7. Juvenile Hormone Mimetics
　　(such as Diofenolan, Epofenonane, Fenoxycarb, Hydroprene, Kinoprene, Methoprene, Pyriproxifen, Triprene)

8. Ecdyson Agonists/Disruptors
　　8.1 Diacylhydrazine (such as Chromafenozide, Halofenozide, Methoxyfenozide, Tebufenozide)

9. Inhibitors of Chitin Biosynthesis
　　9.1 Benzoyl ureas (such as bistrifluron, chlofluazuron, diflubenzuron, fluazuron, flucycloxuron, flufenoxuron, hexaflumoron, lufenuron, novaluron, noviflumuron, penfluron, teflubenzuron, trifulmuron)
　　9.2 Buprofezin
　　9.3 Cyromazine 10. Inhibitors of Oxidative Phosphorylation, ATP Disruptors
　　10.1 Diafenthiuron
　　10.2 Organotins (such as azocyclotin, cyhexatin, fenbutatin oxides)

11. Uncoupler of Oxidative Phosphorylation by Interruption of the Proton Gradients
　　11.1 Pyrroles (such as Chlorfenapyr)
　　11.2 Dinitrophenols (such as binapacryl, dinobuton, dinocap, DNOC)

12. Site I Electron Transport Inhibitors
　　12.1 METIs (such as fenazaquin, fenpyroximate, pyrimidifen, pyridaben, tebufenpyrad, tolfenpyrad)
　　12.2 Hydramethylnone
　　12.3 Dicofol 13. Site II Electron Transport Inhibitors
　　13.1 Rotenone 14. Site III Electron Transport Inhibitors
　　14.1 Acequinocyl, Fluacrypyrim 15. Microbial Disruptors of the Insect Intestinal Membrane

*Bacillus thuringiensis* Strains

16. Fat Synthesis Inhibitors
　　16.1 Tetronic acids (such as Spirodiclofen, Spiromesifen)
　　16.2 Tetramic acids [such as 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS Reg.-No. 382608-10-8) and carbonic acid, cis-3-(2,5-dimethylphenyl)-8-methoxy-2-oxo-1-azaspiro[4.5]dec-3-en-4-yl ethyl ester (CAS Reg. No. 203313-25-1)]

17. Carboxamides
　　(such as flonicamid)

18. Octopaminergic Agonists
　　(such as amitrax)

19. Inhibitors of Magnesium-Stimulated ATPase
　　(such as propargite)

20. Phthalamides
　　(such as $N^2$-[1,1-dimethyl-2-(methylsulfonyl)ethyl]-3-iodo-$N^1$-[2-methyl-4-[1,2,2,2-tetrafluoro-1-(trifluoromethyl)ethyl]phenyl]-1,2-benzenedicarboxamide (CAS Reg. No. 272451-65-7), Flubendiamide)

21. Nereistoxin Analogs
　　(such as thiocyclam hydrogen oxalate, thiosultap-sodium)

22. Bioorganisms, Hormones or Pheromones
　　(such as azadirachtin, *Bacillus* spec., *Beauveria* spec., codlemone, *Metarrhizium* spec., *Paecilomyces* spec., thuringiensin, *Verticillium* spec.)

23. Active Substances with Unknown or Non-Specific Mechanisms of Action
　　23.1 Gas treatment media (such as Aluminium Phosphide, methyl bromide, Sulfuryl fluoride)
　　23.2 Selective Antifeedants (such as Cryolite, flonicamid, Pymetrozine)
　　23.3 Mite growth inhibitors (such as Clofentezine, Etoxazole, Hexythiazox)

23.4 Amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methyl-phenyl-propylcarbamate (tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo-isomers (CAS Reg. No. 185984-60-5) (see WO 96/37494, WO 98/25923), as well as preparations containing insecticidally effective plant extracts, nematodes, fungi or viruses.

Mixing is possible with other known active substances, such as herbicides or with fertilizers and growth regulators, safeners or semiochemicals.

In addition, the inventive compounds of the formula (I) also show very good antimycotic activity. They have a very broad spectrum of antimycotic effectiveness, especially against dermatophytes and sprouting fungi, mold and diphasic fungi (for example against *Candida* species, such as *Candida albicans, Candida glabrata*) as well as *Epidermophyton floccosum, Aspergillus* species, such as *Aspergillus niger* and *Aspergillus fumigatus, Trichophyton* species, such as *Trichophyton mentagrophytes, Microsporon* species, such as *Microsporon canis* and *audouinii*. The listing of these fungi in no way represents a limitation of the ascertainable mycotic spectrum, but rather is only explanatory in character.

The active substances can be used as available, in formulations or application forms prepared therefrom, such as ready-to-use solutions, suspensions, spray powder, pastes, soluble powders, scattering agents and granulates. Application takes place in the usual manner, such as by pouring, spraying, showering, scattering, dusting, foam application, spreading, etc. Furthermore, it is possible to apply the active substances according to the ultra-low volume process or to inject the active substance itself into the ground. Seeds of the plants can also be treated.

For the use of the inventive active substances as fungicides, the application rates can be varied over a wide range, depending on the type of application. For treatment of plant parts, the application rates of active substance generally lie between 0.1 and 10,000 g/ha, preferably between 10 and 1,000 g/ha. For treatment of seeds, the application rates of active substance generally lie between 0.001 and 50 g per kilogram of seed, preferably between 0.01 and 10 g per kilogram of seed. For soil treatment, the application rates of active substance generally lie between 0.1 and 10,000 g/ha, preferably between 1 and 5,000 g/ha.

As mentioned above, all plants and their parts can be treated in accordance with the invention. In a preferred embodiment, naturally occurring plant types and varieties and their parts can be treated, as well as those obtained by conventional biological cultivation methods, such as crossbreeding or protoplast fusion. In a further preferred embodiment, transgenic plants and plant types obtained by genetic technology methods, possibly in combination with conventional methods, (genetically modified organisms) and their parts are treated. The term "parts" or "parts of plants" or "plant parts" was explained above.

It is particularly preferred that plants typically available commercially in each case or plant types in use be treated in accordance with the invention. The term "plant types" is to be understood as plants with new characteristics ("traits") that have been produced by conventional cultivation, as well as those from mutagenesis or recombinant DNA techniques. These can be types, breeds, biotypes and genotypes.

Depending on the plant varieties or types, their location and growing conditions (soils, climates, vegetation cycle, nutrition), treatment in accordance with the invention can also show synergistic effects. Thus, for example, reduced application rates and/or increases in the spectrum of effectiveness and/or an intensification of the activity of the usable materials and agents according to the invention, improved plant growth, increased tolerance of high or low temperatures, increased tolerance of dryness or the salt content of water or soil, increased flowering rates, easier harvesting, accelerated ripening, higher harvest yields, higher quality and/or higher nutritional value of the harvested products, improved storage characteristics and/or processability of the harvested products are possible, which go beyond the effects that are actually anticipated.

The category of transgenic plants or plant types (those obtained via genetic technology) to be treated preferentially according to the invention includes all plants that receive genetic material by modification using gene technology, said material giving these plants particularly advantageous, valuable characteristics ("traits"). Examples of such traits are improved plant growth, increased tolerance of high or low temperatures, increased tolerance of dryness or the salt content of water or soil, increased flowering rates, easier harvesting, accelerated ripening, higher harvest yields, higher quality and/or higher nutritional value of the harvested products, improved storage characteristics and/or processability of the harvested products. Other especially emphasized examples for Such traits are an increase in the defenses of the plants against animal and microbial pests, such as against insects, mites, phytopathogenic fungi, bacteria and/or viruses as well as increased tolerance by the plants of particular herbicidal active substances. Examples of transgenic plants to mention are the important cultured plants, such as grains (wheat, rice), corn, soy, potatoes, cotton, tobacco and rape as well as fruit-bearing plants (with the fruits apples, pears, citrus and grapes), whereby corn, soy, potatoes, cotton, tobacco and rape are especially emphasized. Especially emphasized traits are increased resistance of plants to insects, arachnids, nematodes and snails as a result of toxins produced by the plants, especially those produced in the plants (referred to below as "Bt plants") by genetic material from *Bacillus thuringiensis* (such as by the genes CryIA(a), CryIA(b), CryIA(c), CryIIA, CryIIIA, CryIIIB2, Cry9c Cry2Ab, Cry3Bb and CryIF as well as their combinations). Especially emphasized traits also include increased resistance of plants to fungi, bacteria and viruses through systemic acquired resistance (SAR), systemin, phytoalexins and elicitors as well as resistance genes and corresponding expressed proteins and toxins. Additional especially emphasized traits are increased tolerance of the plants toward particular herbicidal active substances, such as imidazolinones, sulfonyl ureas, glyphosates or phosphinotricin (such as "PAT" genes). The genes providing the particular desired traits can also occur in combinations with one another in the transgenic plants. Examples of "Bt plants" are varieties of corn, cotton, soy and potato marketed under the trade names YIELD GARD® (for example corn, cotton, soy), KnockOut® (for example corn), StarLink® (for example corn), Bollgard® (cotton), Nucoton® (cotton) and NewLeaf® (potato). Examples of herbicide-tolerant plants are varieties of corn, cotton and soy marketed under the trade names Roundup Ready® (tolerance of glyphosates, for example corn, cotton, soy), Liberty Link® (tolerance of phosphinotricin, for example rape), IMI® (tolerance of imidazolinones) and STS® (tolerance of sulfonyl ureas, for example corn). Herbicide-resistant plants (conventionally cultured for herbicide-tolerance) plants are also the varieties marketed under the designation Clearfield® (for example corn). Of course these statements also apply to plant varieties developed or brought to market in the future with these genetic traits or ones developed in the future.

The plants listed can benefit especially from treatment with compounds of general formula (I) or active ingredient mixtures in accordance with the invention. The preferential areas cited above for the active substances or mixtures also apply to the treatment of these plants. Treatment of plants with the compounds or mixtures particularly listed in the present text is especially emphasized.

The synthesis and use of the active substances according to the invention can be seen in the following examples.

SYNTHESIS EXAMPLES

Synthesis of Compound No. 40

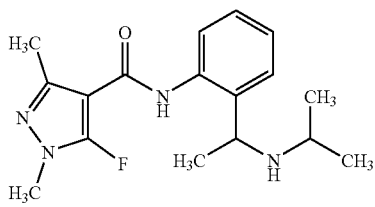

A solution of 0.27 g (1.5 mmol) 5-fluoro-1,3-dimethyl-1H-pyrazole-4-carbonyl chloride in 10 ml dichloromethane is added dropwise to a solution of 0.27 g (1.5 mmol) 2-[1-(isopropylamino)ethyl]aniline (III-4) and 0.42 ml (3.0 mmol) triethylamine in 5 ml dichloromethane. The reaction mixture is stirred for 2 hours at 50° C. and thereafter for 16 hours at room temperature. The reaction mixture is worked up by adding it to water, then the organic phase is dried over magnesium sulfate and concentrated under vacuum. Column chromatography (4:1 hexane/acetone) yielded 0.27 g (56% of the theoretical yield) 5-fluoro-N-{2-[1-(isopropylamino)ethyl]phenyl}-1,3-dimethyl-1H-pyrazole-4-carboxamide [log P (pH 2.3)=0.58].

Synthesis of Compound No. 60

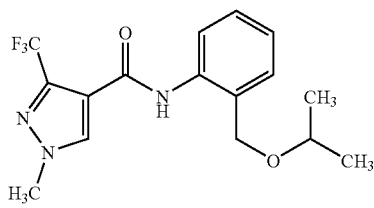

156.0 mg (3.9 mmol) of 60% sodium hydride in oil are added to a solution of 897.8 mg (3.0 mmol) N-[2-(hydroxymethyl)phenyl]-1-methyl-3-(trifluoromethyl)-1H-pyrazole-4-carboxamide (IV-1) in 2 ml dimethyl formamide at room temperature. After 30 minutes, 0.6 ml (6.0 mmol) 2-iodopropane are added. The reaction mixture is stirred for 6 hours at 100° C. and thereafter for 16 hours at room temperature. Afterward, the mixture is diluted with 1 ml methanol, added to water and extracted with ethyl acetate; the organic phase is dried over magnesium sulfate, the drying agent filtered off and the material concentrated under vacuum. Column chromatography (3:1 cyclohexane/ethyl acetate) yielded 100.0 mg (9.7% of the theoretical yield) of N-[2-(isopropoxymethyl)phenyl]-1-methyl-3-(trifluoromethyl)-1H-pyrazol-4-carboxamide [logP (pH 2.3)=2.85].

The compounds listed below in Table 1 were obtained in an analogous manner to examples 1 and 2, as well as according to the general description of the inventive synthesis processes (a) to (m):

TABLE 1

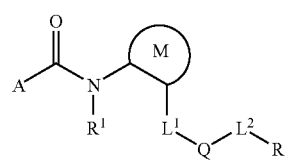

(I)

| No. | $R^1$ | M | —$L^1QL^2R$ | A | logP (pH 2.3) MP (° C.) |
|---|---|---|---|---|---|
| 1 | H | *phenyl# | —$CH_2$—O—$CH_3$ | (3-methyl-4,5-dihydrofuran-2-yl) | 2.18 |
| 2 | H | *phenyl# | —$CH(CH_3)$—$SO_2$—$CH(CH_3)_2$ | (3-methyl-5,6-dihydro-1,4-oxathiin-2-yl) | 2.07 |

TABLE 1-continued (I)

| No. | R¹ | M | —L¹QL²R | A | logP (pH 2.3) MP (° C.) |
|---|---|---|---|---|---|
| 3 | H | phenyl (*,#) | —CH(CH₃)—SO₂—CH(CH₃)₂ | 2-bromophenyl | 2.30 |
| 4 | H | phenyl (*,#) | —CH(CH₃)—SO₂—CH(CH₃)₂ | 2,3-dimethylthiophene | 2.38 |
| 5 | H | phenyl (*,#) | —CH(CH₃)—SO₂—CH(CH₃)₂ | 2-chloro-3-methylpyridine | 1.68 |
| 6 | H | phenyl (*,#) | —CH(CH₃)—SO₂—CH(CH₃)₂ | 2-(trifluoromethyl)phenyl | 2.53 |
| 7 | H | phenyl (*,#) | —CH(CH₃)—SO₂—CH(CH₃)₂ | 2-iodophenyl | 2.43 |
| 8 | H | phenyl (*,#) | —CH(CH₃)—SO₂—CH(CH₃)₂ | 2,3-dimethylfuran | 2.21 |
| 9 | H | phenyl (*,#) | —CH(CH₃)—SO₂—CH(CH₃)₂ | 2,5-dimethyl-4-(trifluoromethyl)thiazole | 2.35 |
| 10 | H | phenyl (*,#) | —CH(CH₃)—SO₂—CH(CH₃)₂ | 3-methyl-2-(trifluoromethyl)-5,6-dihydro-1,4-oxathiine | 2.39 |

TABLE 1-continued (I)

| No. | R¹ | M | —L¹QL²R | A | logP (pH 2.3) MP (° C.) |
|---|---|---|---|---|---|
| 11 | H | phenyl (*, #) | —CH(CH₃)—SO₂—CH(CH₃)₂ | 3,4-dimethyl-5-fluoro-1-methylpyrazole | 1.66 |
| 12 | H | phenyl (*, #) | —CH(CH₃)—SO₂—CH(CH₃)₂ | 2-chlorophenyl | 2.23 |
| 13 | H | phenyl (*, #) | —CH(CH₃)—SO₂—CH(CH₃)₂ | 4-(difluoromethyl)-2,5-dimethylthiazole | 2.16 |
| 14 | H | phenyl (*, #) | —CH(CH₃)—SO₂—CH(CH₃)₂ | 3,4-dimethyl-1-methylpyrazole | 1.46 |
| 15 | H | phenyl (*, #) | —CH(CH₃)—SO₂—CH(CH₃)₂ | 3-(trifluoromethyl)-4-methyl-1-methylpyrazole | 2.09 |
| 16 | H | phenyl (*, #) | —CH(CH₃)—SO₂—CH(CH₃)₂ | 3-(difluoromethyl)-4-methyl-1-methylpyrazole | 1.86 |
| 17 | H | phenyl (*, #) | —CH(CH₃)—S—CH(CH₃)₂ | 3,4-dimethyl-1-methylpyrazole | 2.53 |

TABLE 1-continued (I)

| No. | R¹ | M | —L¹QL²R | A | logP (pH 2.3) MP (° C.) |
|---|---|---|---|---|---|
| 18 | H | phenyl (*, #) | —CH(CH₃)—S—CH(CH₃)₂ | 3-(trifluoromethyl)-4-methyl-1-methyl-1H-pyrazole | 3.27 |
| 19 | H | phenyl (*, #) | —CH(CH₃)—S—CH(CH₃)₂ | 3,4-dimethyl-5-fluoro-1-methyl-1H-pyrazole | 2.98 |
| 20 | H | phenyl (*, #) | —CH(CH₃)—S—CH(CH₃)₂ | 2,3-dimethylthiophene | 4.03 |
| 21 | H | phenyl (*, #) | —CH(CH₃)—S—CH(CH₃)₂ | 2-chloro-3-methylphenyl | 3.74 |
| 22 | H | phenyl (*, #) | —CH(CH₃)—S—CH(CH₃)₂ | 2-chloro-3-methylpyridine | 2.95 |
| 23 | H | phenyl (*, #) | —CH(CH₃)—S—CH(CH₃)₂ | 2-(trifluoromethyl)-3-methylphenyl | 3.90 |
| 24 | H | phenyl (*, #) | —CH(CH₃)—S—CH(CH₃)₂ | 2,3-dimethylfuran | 3.71 |

TABLE 1-continued (I)

| No. | R¹ | M | —L¹QL²R | A | logP (pH 2.3) MP (° C.) |
|---|---|---|---|---|---|
| 25 | H | *phenyl# | —CH(CH₃)—S—CH(CH₃)₂ | 2-methyl-4-(trifluoromethyl)-5-thiazolyl (F₃C, CH₃ on thiazole with S, N, CH₃) | 3.73 |
| 26 | H | *phenyl# | —CH(CH₃)—S—CH(CH₃)₂ | 2-bromo-phenyl (methyl, Br) | 3.79 |
| 27 | H | *phenyl# | —CH(CH₃)—S—CH(CH₃)₂ | 2-iodo-phenyl (methyl, I) | 3.91 |
| 28 | H | *phenyl# | —CH(CH₃)—S—CH(CH₃)₂ | pyrazolyl (F₂HC, CH₃, N, N—CH₃) | 3.01 |
| 29 | H | *phenyl# | —CH(CH₃)—S—CH(CH₃)₂ | thiazolyl (F₂HC, CH₃, N, S, CH₃) | 3.55 |
| 30 | H | *phenyl# | —CH(CH₃)—S—CH(CH₃)₂ | dihydrooxathiin (S, CH₃, O, CF₃) | 3.76 |
| 31 | H | *phenyl# | —CH(CH₃)—O—CH₃ | pyrazolyl (H₃C, CH₃, N, N—CH₃, F) | 2.17 |

TABLE 1-continued (I)

| No. | R¹ | M | —L¹QL²R | A | logP (pH 2.3) MP (° C.) |
|-----|----|----|---------|---|-------------------------|
| 32 | H | phenyl (*, #) | —CH(CH₃)—O—CH₃ | 3-CF₃-4-methyl-1-methylpyrazol-5-yl | 2.46 |
| 33 | H | 4-Cl-phenyl (*, #) | —CH(CH₃)—O—CH₃ | 2-CF₃-phenyl | 3.56 |
| 34 | H | phenyl (*, #) | —CH(CH₃)—O—CH₃ | 2-CF₃-phenyl | 2.99 |
| 35 | H | phenyl (*, #) | —CH₂—S—CH(CH₃)₂ | 4-CF₂H-5-methyl-2-methylthiazol-yl | 3.27 |
| 36 | H | phenyl (*, #) | —CH₂—S—CH(CH₃)₂ | 3-CF₃-4-methyl-1-methylpyrazol-5-yl | 3.05 |
| 37 | H | phenyl (*, #) | —CH₂—S—CH(CH₃)₂ | 3-methyl-2-CF₃-5,6-dihydro-1,4-oxathiin-yl | 3.48 |
| 38 | H | phenyl (*, #) | —CH₂—S—CH(CH₃)₂ | 3-CF₂H-4-methyl-1-methylpyrazol-5-yl | 2.76 |
| 39 | H | phenyl (*, #) | —CH₂—S—CH(CH₃)₂ | 2-I-phenyl | 3.68 |

TABLE 1-continued

| No. | R¹ | M | —L¹QL²R | A | logP (pH 2.3) MP (° C.) |
|---|---|---|---|---|---|
| 40 | H | *ortho-phenylene (* and #)* | —CH(CH₃)—NH—CH(CH₃)₂ | 5-fluoro-1,4-dimethyl-3-methyl-pyrazole | 0.58 |
| 41 | H | *ortho-phenylene* | —CH(CH₃)—NH—CH(CH₃)₂ | 1,4-dimethyl-3-(trifluoromethyl)pyrazole | 1.06 |
| 42 | H | *ortho-phenylene* | —CH(CH₃)—S—CH(CH₃)(CH₂)₂CH₃ | 1,4-dimethyl-3-(trifluoromethyl)pyrazole | 4.02 |
| 43 | H | *ortho-phenylene* | —CH(CH₃)—S—CH(CH₃)(CH₂)₂CH₃ | 5-fluoro-1,4-dimethyl-3-methyl-pyrazole | 3.82 |
| 44 | H | *ortho-phenylene* | —CH(CH₃)—S—CH(CH₃)(CH₂)₂CH₃ | 2,5-dimethyl-4-(trifluoromethyl)thiazole | 4.52 |
| 45 | H | *ortho-phenylene* | —CH(CH₃)—S—CH(CH₃)CH₂CH₃ | 1,4-dimethyl-3-(trifluoromethyl)pyrazole | 4.14 |
| 46 | H | *ortho-phenylene* | —CH(CH₃)—S—CH(CH₃)CH₂CH₃ | 5-fluoro-1,4-dimethyl-3-methyl-pyrazole | 3.38 |

TABLE 1-continued (I)

| No. | R¹ | M | —L¹QL²R | A | logP (pH 2.3) MP (° C.) |
|---|---|---|---|---|---|
| 47 | H | phenyl (*, #) | —CH(CH₃)—S—CH(CH₃)(CH₂)₂CH₃ | 2-iodophenyl | 4.75 |
| 48 | H | phenyl (*, #) | —CH(CH₃)—S—CH(CH₃)CH₂CH₃ | 4-CF₃-5-methyl-2-methylthiazole | 4.12 |
| 49 | H | phenyl (*, #) | —CH(CH₃)—S—CH(CH₃)CH₂CH₃ | 2-iodophenyl | 4.33 |
| 50 | H | phenyl (*, #) | —CH₂—O—C(O)—CHCl₂ | 2-CF₃-phenyl | 3.15 |
| 51 | H | phenyl (*, #) | —CH₂—O—C(O)—CH(CH₃)₂ | 3,4-dimethyl-5-fluoro-1-methylpyrazole | 2.39 |
| 52 | H | phenyl (*, #) | —CH₂—O—C(O)—CHCl₂ | 3,4-dimethyl-5-fluoro-1-methylpyrazole | 2.36 |
| 53 | H | phenyl (*, #) | —CH₂—O—C(O)—CH(CH₃)₂ | 2-CF₃-phenyl | 3.24 |
| 54 | H | phenyl (*, #) | —CH₂—O—CH(CH₃)₂ | 2-CF₃-phenyl | 2.51 |

TABLE 1-continued (I)

| No. | R¹ | M | —L¹QL²R | A | logP (pH 2.3) MP (° C.) |
|---|---|---|---|---|---|
| 55 | H | *—phenyl—# (ortho) | —CH₂—O—C(O)—CH(CH₃)₂ | 3-CF₃-4-methyl-1-methyl-pyrazol-5-yl | 2.74 |
| 56 | H | *—phenyl—# (ortho) | —CH₂—O—C(O)—CHCl₂ | 3-CF₃-4-methyl-1-methyl-pyrazol-5-yl | 2.69 |
| 57 | H | *—phenyl—# (ortho) | —CH₂—O—C(O)—CH(CH₃)₂ | 2-chloro-3-methyl-pyridin-yl | 2.38 |
| 58 | H | *—phenyl—# (ortho) | —CH₂—O—C(O)—CHCl₂ | 2-chloro-3-methyl-pyridin-yl | 2.38 |
| 59 | C(O)i-Pr | *—phenyl—# (ortho) | —CH₂—O—C(O)—CH(CH₃)₂ | 2-chloro-3-methyl-pyridin-yl | 3.49 |
| 60 | H | *—phenyl—# (ortho) | —CH₂—O—CH(CH₃)₂ | 3-CF₃-4-methyl-1-methyl-pyrazol-5-yl | 2.85 |
| 61 | H | *—phenyl—# (ortho) | —(CH₂)₂C(CH₃)₂—O—C(O)—CH₃ | 2-CF₃-phenyl | 3.30 |
| 62 | H | *—phenyl—# (ortho) | —(CH₂)₂OH | 3-CF₃-4-methyl-1-methyl-pyrazol-5-yl | 1.62 |

TABLE 1-continued (I)

| No. | R¹ | M | —L¹QL²R | A | logP (pH 2.3) MP (° C.) |
|-----|----|----|---------|---|------------------------|
| 63 | H | *phenyl* | —(CH₂)₂OH | 3-methyl-5-fluoro-4-methyl-1-methylpyrazole | 1.21 |
| 64 | H | *phenyl* | —(CH₂)₂—O—C(O)—CH(CH₃)₂ | 3-CF₃-4-methyl-1-methylpyrazole | 2.79 |
| 65 | H | *phenyl* | —(CH₂)₂—O—Si(CH₃)₂—C(CH₃)₃ | 3-CF₃-4-methyl-1-methylpyrazole | 4.59 |
| 66 | H | *phenyl* | —(CH₂)₂—O—C(O)—CHCl₂ | 3-CF₃-4-methyl-1-methylpyrazole | 2.76 |
| 67 | H | *phenyl* | —(CH₂)₂—O—C(O)—CH(CH₃)₂ | 3-methyl-5-fluoro-4-methyl-1-methylpyrazole | 2.40 |
| 68 | H | *phenyl* | —(CH₂)₂—O—C(O)—CHCl₂ | 3-methyl-5-fluoro-4-methyl-1-methylpyrazole | 2.43 |
| 69 | H | *phenyl* | —(CH₂)₂—O—Si(CH₃)₂—C(CH₃)₃ | 3-methyl-5-fluoro-4-methyl-1-methylpyrazole | 4.49 |

TABLE 1-continued (I)

| No. | R¹ | M | —L¹QL²R | A | logP (pH 2.3) MP (° C.) |
|---|---|---|---|---|---|
| 70 | H | phenyl (*, #) | —CH(CH₃)—S—CH(CH₃)(CH₂)₂CH₃ | 2-CF₃-phenyl | 4.71 |
| 71 | H | phenyl (*, #) | —CH(CH₃)—S—CH(CH₃)(CH₂)₂CH₃ | 2,3-dimethylthiophene | 4.93 |
| 72 | H | phenyl (*, #) | —CH(CH₃)—S—CH(CH₃)(CH₂)₂CH₃ | 2-Cl-phenyl | 4.60 |
| 73 | H | phenyl (*, #) | —CH(CH₃)—S—CH(CH₃)CH₂CH₃ | 2-Cl-phenyl | 4.17 |
| 74 | H | phenyl (*, #) | —CH(CH₃)—S—CH(CH₃)CH₂CH₃ | 2,3-dimethylfuran | 4.17 |
| 75 | H | phenyl (*, #) | —CH(CH₃)—S—CH(CH₃)CH₂CH₃ | 2-CF₃-phenyl | 4.31 |
| 76 | H | phenyl (*, #) | —CH(CH₃)—S—CH(CH₃)CH₂CH₃ | 2,3-dimethylthiophene | 4.47 |
| 77 | H | phenyl (*, #) | —CH(CH₃)—S—CH(CH₃)(CH₂)₂CH₃ | 2,3-dimethylfuran | 4.61 |

TABLE 1-continued (I)

A—C(=O)—N(R¹)—[M(L¹—Q—L²—R)]

| No. | R¹ | M | —L¹QL²R | A | logP (pH 2.3) MP (° C.) |
|---|---|---|---|---|---|
| 78 | H | *phenyl#* | —CH(CH₃)—S—CH(CH₃)CH₂CH₃ | 4-(F₂HC)-5-methyl-2-methylthiazol-yl | 3.95 |
| 79 | H | *phenyl#* | —CH(CH₃)—S—CH(CH₃)(CH₂)₂CH₃ | 4-(F₂HC)-5-methyl-2-methylthiazol-yl | 4.36 |
| 80 | H | *phenyl#* | —CH(CH₃)—S—CH(CH₃)CH₂CH₃ | 3-(F₂HC)-4-methyl-1-methylpyrazol-yl | 3.38 |
| 81 | H | *phenyl#* | —CH(CH₃)—S—CH(CH₃)(CH₂)₂CH₃ | 2-bromo-methylphenyl | 4.63 |
| 82 | H | *phenyl#* | —CH(CH₃)—S—CH(CH₃)(CH₂)₂CH₃ | 3,4-dimethyl-1-methylpyrazol-yl | 3.27 |
| 83 | H | *phenyl#* | —CH(CH₃)—S—CH(CH₃)CH₂CH₃ | 2-bromo-methylphenyl | 4.21 |
| 84 | H | *phenyl#* | —CH(CH₃)—S—CH(CH₃)CH₂CH₃ | 3,4-dimethyl-1-methylpyrazol-yl | 2.90 |

TABLE 1-continued (I)

| No. | R¹ | M | —L¹QL²R | A | logP (pH 2.3) MP (° C.) |
|---|---|---|---|---|---|
| 85 | H | phenyl (*,#) | —CH(CH₃)—S—CH(CH₃)(CH₂)₂CH₃ | F₂HC-, CH₃-pyrazole, N-CH₃ | 3.76 |
| 86 | H | phenyl (*,#) | —CH(CH₃)—S—CH(CH₃)CH₂CH₃ | 2,3-dimethyl-5,6-dihydro-1,4-oxathiine | 4.07 |
| 87 | H | phenyl (*,#) | —CH(CH₃)—S—CH(CH₃)(CH₂)₂CH₃ | 2,3-dimethyl-5,6-dihydro-1,4-oxathiine | 4.53 |
| 88 | H | phenyl (*,#) | —CH(CH₃)—S—CH(CH₃)CH₂CH₃ | F₃C-, CH₃-pyrrole, N-CH₃ | 3.92 |
| 89 | H | phenyl (*,#) | —CH(CH₃)—S—CH(CH₃)CH₂CH₃ | 2,3-dimethyl-5,6-dihydro-1,4-oxathiine | 4.10 |
| 90 | H | phenyl (*,#) | —CH(CH₃)—S—cyclopentyl | 2,3-dimethylthiophene | 3.16 |
| 91 | H | phenyl (*,#) | —CH(CH₃)—S—cyclopentyl | 2-methyl-3-methylfuran | 4.31 |
| 92 | H | phenyl (*,#) | —CH(CH₃)—S—cyclopentyl | 2-methyl-6-chlorophenyl | 4.29 |

TABLE 1-continued (I)

| No. | R¹ | M | —L¹QL²R | A | logP (pH 2.3) MP (° C.) |
|---|---|---|---|---|---|
| 93 | H | o-phenyl (*,#) | —CH(CH₃)—S—cyclopentyl | 2-bromophenyl | 4.34 |
| 94 | H | o-phenyl (*,#) | —CH(CH₃)—S—cyclopentyl | 4-CF₃-2-methyl-thiazol-5-yl (2-CH₃) | 4.24 |
| 95 | H | o-phenyl (*,#) | —CH(CH₃)—S—cyclopentyl | 3,4-dimethyl-1-methyl-pyrazol-5-yl | 3.04 |
| 96 | H | o-phenyl (*,#) | —CH(CH₃)—S—cyclopentyl | 3-CF₃-4-methyl-1-methyl-pyrazol-5-yl | 3.76 |
| 97 | H | o-phenyl (*,#) | —CH(CH₃)—S—cyclopentyl | 2-CF₃-phenyl | 4.41 |
| 98 | H | o-phenyl (*,#) | —CH(CH₃)—S—CH(CH₃)₂ | 2,3-dimethyl-5,6-dihydro-1,4-oxathiine | 3.65 |
| 99 | H | o-phenyl (*,#) | —CH(CH₃)—S—cyclopentyl | 2-methylphenyl | 4.44 |
| 100 | H | o-phenyl (*,#) | —CH(CH₃)—S—cyclopentyl | 3,4-dimethyl-5-fluoro-1-methyl-pyrazolyl | 4.03 |

TABLE 1-continued (I)

| No. | R¹ | M | —L¹QL²R | A | logP (pH 2.3) MP (° C.) |
|---|---|---|---|---|---|
| 101 | H | *ortho-phenyl# | —CH(CH₃)—S—cyclopentyl | 3-(CHF₂)-4-methyl-1-methylpyrazol-5-yl | 3.48 |
| 102 | H | *ortho-phenyl# | —CH(CH₃)—S—cyclopentyl | 4-(CHF₂)-5-methyl-2-methylthiazol-3-yl | 4.07 |
| 103 | H | *ortho-phenyl# | —CH(CH₃)—S—CH(CH₃)₂ | 2-methylphenyl | 3.88 |
| 104 | H | *ortho-phenyl# | —CH(CH₃)—S—CH(CH₃)₂ | 3,4-dimethyl-5-chloro-1-methylpyrazolyl | 3.20 |
| 105 | H | *ortho-phenyl# | —CH(CH₃)—S—CH(CH₃)₂ | 3-(CF₃)-4-methyl-1-methylpyrrolyl | 3.57 |
| 106 | H | *ortho-phenyl# | —CH(CH₃)—S—CH(CH₃)₂ | 3,4-dimethyl-5-fluoro-1-methylpyrazolyl | 3.63 |
| 107 | H | *ortho-phenyl# | —CH(CH₃)—S—cyclopentyl | 2,3-dimethyl-5,6-dihydro-1,4-oxathiinyl | 4.24 |

TABLE 1-continued (I)

| No. | R¹ | M | —L¹QL²R | A | logP (pH 2.3) MP (° C.) |
|---|---|---|---|---|---|
| 108 | H | phenyl (*,#) | —CH(CH₃)—S—cyclopentyl | 3-methyl-2-(CF₃)-5,6-dihydro-1,4-oxathiine | 4.21 |
| 109 | H | phenyl (*,#) | —CH(CH₃)—S—CH(CH₃)(CH₂)₂CH₃ | 3-(F₃C)-4-methyl-1-methyl-pyrrole | 4.29 |
| 110 | H | phenyl (*,#) | —CH(CH₃)—S—CH(CH₃)(CH₂)₂CH₃ | 3-methyl-2-(CF₃)-5,6-dihydro-1,4-oxathiine | 4.49 |
| 111 | H | phenyl (*,#) | —CH(CH₃)—S—CH(CH₃)(CH₂)₂CH₃ | 3-(F₃C)-4-methyl-5-F-1-methyl-pyrazole | 4.38 |
| 112 | H | phenyl (*,#) | —CH(CH₃)—S—CH(CH₃)(CH₂)₂CH₃ | 2-methylphenyl | 4.76 |
| 113 | H | phenyl (*,#) | —CH(CH₃)—S—CH(CH₃)(CH₂)₂CH₃ | 3-(H₃C)-4-methyl-5-Cl-1-methyl-pyrazole | 4.07 |
| 114 | H | phenyl (*,#) | —CH(CH₃)—S—CH(CH₃)(CH₂)₂CH₃ | 3-methyl-2-Cl-pyridine | 3.79 |

TABLE 1-continued

| No. | R¹ | M | —L¹QL²R | A | logP (pH 2.3) MP (° C.) |
|---|---|---|---|---|---|
| 115 | H | *o-phenyl# | —CH(CH₃)—S—cyclopentyl | 3-CF₃, 4-CH₃, 1-CH₃-pyrrole | 4.02 |
| 116 | H | *o-phenyl# | —CH(CH₃)—S—cyclopentyl | 2-Cl, 3-CH₃-pyridine | 3.46 |
| 117 | H | *o-phenyl# | —CH(CH₃)—S—cyclopentyl | 2-I, 3-CH₃-phenyl | 4.45 |
| 118 | H | *o-phenyl# | —CH(CH₃)—S—cyclopentyl | 3-CF₃, 4-CH₃, 5-F, 1-CH₃-pyrazole | 4.12 |
| 119 | H | *o-phenyl# | —CH(CH₃)—S—cyclopentyl | 3-CH₃, 4-CH₃, 5-Cl, 1-CH₃-pyrazole | 3.76 |
| 120 | H | *o-phenyl# | —CH(CH₃)—S—CH(CH₃)CH₂CH₃ | 2-Cl, 3-CH₃-pyridine | 3.35 |
| 121 | H | *o-phenyl# | —CH(CH₃)—S—CH(CH₃)CH₂CH₃ | 3-CF₃, 4-CH₃, 5-F, 1-CH₃-pyrazole | 3.99 |

TABLE 1-continued (I)

| No. | R¹ | M | —L¹QL²R | A | logP (pH 2.3) MP (° C.) |
|---|---|---|---|---|---|
| 122 | H | *phenyl* | —CH(CH₃)—S—CH(CH₃)CH₂CH₃ | 2-methylphenyl | 4.31 |
| 123 | H | *phenyl* | —CH(CH₃)—S—CH(CH₃)CH₂CH₃ | 5-chloro-1,3,4-trimethyl-1H-pyrazol-yl | 3.60 |
| 124 | H | *phenyl* | —CH(CH₃)—O—CH(CH₃)₂ | 5-fluoro-1,3,4-trimethyl-1H-pyrazol-yl | 2.90 |
| 125 | H | *phenyl* | —CH(CH₃)—O—CH(CH₃)₂ | 2,3-dimethylthiophen-yl | 4.50 |
| 126 | H | *phenyl* | —CH(CH₃)—O—CH(CH₃)₂ | 2,3-dimethylfuran-yl | 3.80 |
| 127 | H | *phenyl* | —CH(CH₃)—O—CH(CH₃)₂ | 4-methyl-3-(trifluoromethyl)-1-methyl-1H-pyrazol-yl | 3.14 |
| 128 | H | *phenyl* | —CH(CH₃)—O—CH(CH₃)₂ | 2,3-dimethyl-5,6-dihydro-1,4-oxathiin-yl | 3.47 |

TABLE 1-continued (I)

| No. | R¹ | M | —L¹QL²R | A | logP (pH 2.3) MP (° C.) |
|---|---|---|---|---|---|
| 129 | H | phenyl (*,#) | —CH(CH₃)—O—CH(CH₃)₂ | 3-iodo-4-methyl-1-methyl-pyrazole | 2.75 |
| 130 | H | phenyl (*,#) | —CH(CH₃)—O—CH(CH₃)₂ | 2-iodo-methylphenyl | 3.83 |
| 131 | H | phenyl (*,#) | —CH(CH₃)—O—CH(CH₃)₂ | 4-(F₂HC)-5-methyl-2-methyl-thiazole | 3.58 |
| 132 | H | phenyl (*,#) | —CH(CH₃)—O—CH(CH₃)₂ | 2-chloro-3-methylpyridine | 2.72 |
| 133 | H | phenyl (*,#) | —CH(CH₃)—O—CH(CH₃)₂ | 4-(F₃C)-5-methyl-2-methyl-thiazole | 3.65 |
| 134 | H | phenyl (*,#) | —CH(CH₃)—O—CH(CH₃)₂ | 2-CF₃-methylphenyl | 3.81 |
| 135 | H | phenyl (*,#) | —CH(CH₃)—O—CH(CH₃)₂ | 3-(F₂HC)-4-methyl-1-methyl-pyrazole | 2.89 |

TABLE 1-continued (I)

| No. | R¹ | M | —L¹QL²R | A | logP (pH 2.3) MP (° C.) |
|---|---|---|---|---|---|
| 136 | H | phenyl (*, #) | —CH(CH₃)—O—CH(CH₃)₂ | 1-methyl-4-methyl-5-CHF₂-pyrazole | 3.67 |
| 137 | H | phenyl (*, #) | —CH(CH₃)—O—CH(CH₃)₂ | 3-methyl-2-CF₃-5,6-dihydro-1,4-oxathiine | 3.64 |
| 138 | H | phenyl (*, #) | —CH(CH₃)—O—CH(CH₃)₂ | 1-methyl-3-CF₃-4-methyl-pyrrole | 5.60 |
| 139 | H | phenyl (*, #) | —CH₂—N(CH₃)₂ | 1-methyl-3-methyl-4-methyl-pyrazole | 98° C. |
| 140 | H | phenyl (*, #) | —CH₂—N(CH₃)₂ | 2-methyl-6-CF₃-phenyl | |
| 141 | H | phenyl (*, #) | —CH₂—S—CH₂CH₃ | 1-methyl-3-CF₃-4-methyl-pyrazole | |
| 142 | H | phenyl (*, #) | —CH₂—S—CH₂CH₃ | 1-methyl-3-CHF₂-4-methyl-pyrazole | 103° C. |

TABLE 1-continued (I)

| No. | R¹ | M | —L¹QL²R | A | logP (pH 2.3) MP (° C.) |
|-----|----|----|---------|---|------------------------|
| 143 | H | phenyl (*, #) | —CH₂—S—CH₂CH₃ | 3-methyl-4-methyl-5-chloro-1-methylpyrazole | 96° C. |
| 144 | H | phenyl (*, #) | —CH₂—S—CH₂CH₃ | 4-CF₃-5-methyl-2-methylthiazole | |
| 145 | H | phenyl (*, #) | —CH₂—SO—CH₂CH₃ | 3-methyl-4-methyl-5-chloro-1-methylpyrazole | |
| 146 | H | phenyl (*, #) | —CH₂—S—CH₂CH₃ | 3-methyl-4-methyl-1-methylpyrazole | 105° C. |
| 147 | H | phenyl (*, #) | —CH₂—SO—CH₂CH₃ | 4-CF₃-5-methyl-2-methylthiazole | |
| 148 | H | phenyl (*, #) | —CH₂—SO—CH₂CH₃ | 3-CF₃-4-methyl-1-methylpyrazole | |
| 149 | H | phenyl (*, #) | —CH₂—SO—CH₂CH₃ | 3-CHF₂-4-methyl-1-methylpyrazole | |

TABLE 1-continued (I)

| No. | R¹ | M | —L¹QL²R | A | logP (pH 2.3) MP (° C.) |
|---|---|---|---|---|---|
| 150 | H | phenyl (*, #) | —CH₂—SO₂—CH₂CH₃ | 3-methyl-4-methyl-5-chloro-1-methyl-pyrazole | 148° C. |
| 151 | H | phenyl (*, #) | —CH₂—SO₂—CH₂CH₃ | 3-trifluoromethyl-4-methyl-1-methyl-pyrazole | 135° C. |
| 152 | H | phenyl (*, #) | —CH₂—SO₂—CH₂CH₃ | 4-trifluoromethyl-5-methyl-2-methyl-thiazole | 142° C. |
| 153 | H | 4-OCH₃-phenyl (*, #) | —CH₂—S—CH₂CH₃ | 3-methyl-4-methyl-1-methyl-pyrazole | 142° C. |
| 154 | H | 4-CH₃-phenyl (*, #) | —CH₂—S—CH₂CH₃ | 3-methyl-4-methyl-1-methyl-pyrazole | 116° C. |
| 155 | H | 4-OCH₃-phenyl (*, #) | —CH₂—S—CH₂CH₃ | 3-methyl-4-methyl-5-chloro-1-methyl-pyrazole | 125° C. |
| 156 | H | 4-CH₃-phenyl (*, #) | —CH₂—S—CH₂CH₃ | 4-chloro-5-methyl-2-chloro-thiazole | 72° C. |

TABLE 1-continued (I)

| No. | R¹ | M | —L¹QL²R | A | logP (pH 2.3) MP (° C.) |
|---|---|---|---|---|---|
| 157 | H | phenyl (*,#ortho) | —CH₂—SO₂—CH₂CH₃ | 3,4-dimethyl-1-methyl-pyrazol-5-yl | |
| 158 | H | phenyl with OCH₃ | —CH₂—S—CH₂CH₃ | 3-CF₃-4-methyl-1-methyl-pyrazol-5-yl | 135° C. |
| 159 | H | phenyl (*,#ortho) | —CH₂—SO₂—CH₂CH₃ | 3-CHF₂-4-methyl-1-methyl-pyrazol-5-yl | 143° C. |
| 160 | H | phenyl (*,#ortho) | —CH₂—SO₂—CH₂CH₃ | 3,4-dimethyl-1-methyl-pyrazol-5-yl | |
| 161 | H | phenyl with CH₃ | —CH₂—S—CH₂CH₃ | 3,4-dimethyl-5-chloro-1-methyl-pyrazol-yl | 127° C. |
| 162 | H | phenyl with CH₃ | —CH₂—S—CH₂CH₃ | 3-CF₃-4-methyl-1-methyl-pyrazol-5-yl | |
| 163 | H | phenyl with CH₃ | —CH₂—S—CH₂CH₃ | 4-CF₃-2-methyl-thiazol-5-yl | |

TABLE 1-continued (I)

A—C(=O)—N(R¹)—[M ring with L¹—Q—L²—R substituent]

| No. | R¹ | M | —L¹QL²R | A | logP (pH 2.3) MP (° C.) |
|---|---|---|---|---|---|
| 164 | H | 4-OCH₃-phenyl (*, # positions) | —CH₂—S—CH₂CH₃ | 2,4-dichloro-5-methyl-thiazol-yl | 116° C. |
| 165 | H | 4-OCH₃-phenyl (*, # positions) | —CH₂—S—CH₂CH₃ | 4-CF₃-2-methyl-5-methyl-thiazol-yl | 98° C. |
| 166 | H | 4-CH₃-phenyl (*, # positions) | —CH₂—S—CH₂CH₃ | 3-CF₃-4-methyl-5-chloro-1-methyl-pyrazol-yl | 132° C. |
| 167 | H | 4-CH₃-phenyl (*, # positions) | —CH₂—S—CH₂CH₃ | 3-CHF₂-4-methyl-1-methyl-pyrazol-yl | 86° C. |
| 168 | H | 4-OCH₃-phenyl (*, # positions) | —CH₂—S—CH₂CH₃ | 3-CHF₂-4-methyl-1-methyl-pyrazol-yl | 110° C. |
| 169 | H | phenyl (*, # positions) | —CH₂—S—CH₂CH₃ | 2-CF₃-6-methyl-phenyl | 79° C. |
| 170 | H | phenyl (*, # positions) | —CH₂—S—CH₂CH₃ | 2-chloro-3-methyl-pyridin-yl | 75° C. |

TABLE 1-continued (I)

| No. | R¹ | M | —L¹QL²R | A | logP (pH 2.3) MP (° C.) |
|-----|----|----|---------|---|------------------------|
| 171 | H | 4-CH₃-phenyl (*,#) | —CH₂—S—CH₂CH₃ | 2-CF₃-phenyl | 105° C. |
| 172 | H | 4-CH₃-phenyl (*,#) | —CH₂—S—CH₂CH₃ | 2-Cl-3-methyl-pyridinyl | 112° C. |
| 173 | H | 4-OCH₃-phenyl (*,#) | —CH₂—S—CH₂CH₃ | 2-Cl-3-methyl-pyridinyl | 138° C. |
| 174 | H | 4-OCH₃-phenyl (*,#) | —CH₂—S—CH₂CH₃ | 2-CF₃-phenyl | 120° C. |
| 175 | H | phenyl (*,#) | —CH₂—S—CH₂CH₃ | 2,3-dimethyl-5,6-dihydro-1,4-oxathiine | 71° C. |
| 176 | H | 4-CH₃-phenyl (*,#) | —CH₂—S—CH₂CH₃ | 2,3-dimethyl-5,6-dihydro-1,4-oxathiine | |
| 177 | H | 4-OCH₃-phenyl (*,#) | —CH₂—S—CH₂CH₃ | 2,3-dimethyl-5,6-dihydro-1,4-oxathiine | 68° C. |
| 178 | H | phenyl (*,#) | —CH₂—OH | 3-CF₃-1-methyl-pyrazol-4-yl | 1.61 |

TABLE 1-continued (I)

| No. | R¹ | M | —L¹QL²R | A | logP (pH 2.3) MP (° C.) |
|-----|----|----|---------|---|------------------------|
| 179 | H | phenyl (*, #) | —CH₂—S—CH₂CH(CH₃)₂ | 3-methyl-2-chloropyridin-yl | 92° C. |
| 180 | H | phenyl (*, #) | —CH₂—S—CH₂CH(CH₃)₂ | 3-(F₂HC)-4-methyl-1-methyl-pyrazol-yl | |
| 181 | H | phenyl (*, #) | —CH₂—S—CH₂CH(CH₃)₂ | 3-H₃C-4-methyl-1-methyl-pyrazol-yl | 86° C. |
| 182 | H | phenyl (*, #) | —CH₂—S—CH₂CH(CH₃)₂ | 3-F₃C-4-methyl-1-methyl-pyrazol-yl | 82° C. |
| 183 | H | phenyl (*, #) | —CH₂—S—CH₂CH(CH₃)₂ | 2,3-dimethyl-5,6-dihydro-1,4-oxathiin-yl | 45° C. |
| 184 | H | phenyl (*, #) | —CH₂—S—CH₂CH(CH₃)₂ | 3-H₃C-4-methyl-5-chloro-1-methyl-pyrazol-yl | |
| 185 | H | phenyl (*, #) | —CH₂—S—CH₂CH(CH₃)₂ | 4-F₃C-5-methyl-2-methyl-thiazol-yl | |

TABLE 1-continued (I)

| No. | R¹ | M | —L¹QL²R | A | logP (pH 2.3) MP (° C.) |
|---|---|---|---|---|---|
| 186 | H | phenyl (*,#) | —CH₂—S—CH₂CH(CH₃)₂ | 2-CF₃-phenyl | 94° C. |
| 187 | H | phenyl (*,#) | —CH₂—S—CH₂CH(CH₃)₂ | 3-methyl-2-CF₃-5,6-dihydro-1,4-oxathiine | 77° C. |
| 188 | H | 4-methyl-2-# phenyl (*) | —CH₂—S—CH₂CH₃ | 3,4-dimethyl-5-fluoro-1-methyl-pyrazole | 96° C. |
| 189 | H | phenyl (*,#) | —CH₂—S—CH₂CH(CH₃)₂ | 3,4-dimethyl-5-fluoro-1-methyl-pyrazole | |
| 190 | H | 4-OCH₃-2-# phenyl (*) | —CH₂—S—CH₂CH₃ | 3,4-dimethyl-5-fluoro-1-methyl-pyrazole | 147° C. |
| 191 | H | phenyl (*,#) | —CH₂—S—CH₃ | 2-methylphenyl | |
| 192 | H | phenyl (*,#) | —CH(CH₃)—S—CH₂CH₃ | 3-CF₃-4-methyl-1-methyl-pyrazole | |

TABLE 1-continued (I)

| No. | R¹ | M | —L¹QL²R | A | logP (pH 2.3) MP (° C.) |
|---|---|---|---|---|---|
| 193 | H | phenyl (*, #) | —CH(CH₃)—S—CH₂CH₃ | 1-methyl-3-methyl-4-methyl-5-fluoro-pyrazole | |
| 194 | H | phenyl (*, #) | —CH(CH₃)—S—CH₂CH₃ | 1-methyl-3-methyl-4-methyl-5-chloro-pyrazole | |
| 195 | H | phenyl (*, #) | —CH(CH₃)—S—CH₂CH₃ | 2-methyl-4-trifluoromethyl-5-methyl-thiazole | |
| 196 | H | 4-fluorophenyl (*, #) | —CH(CH₃)—S—CH₂CH₃ | 1-methyl-3-trifluoromethyl-4-methyl-pyrazole | |
| 197 | H | 4-fluorophenyl (*, #) | —CH(CH₃)—S—CH₂CH₃ | 1-methyl-3-methyl-4-methyl-5-fluoro-pyrazole | |
| 198 | H | 4-fluorophenyl (*, #) | —CH(CH₃)—S—CH₂CH₃ | 1-methyl-3-methyl-4-methyl-5-chloro-pyrazole | |

[a] The bond marked with the asterisk ("*") is linked with the amide.

Synthesis of Starting Materials of the Formula (III)

Example (III-1)

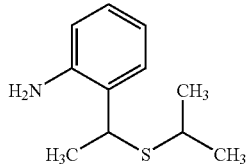

44 g (0.188 mol) 1-[1-(isopropylthio)ethyl]-2-nitrobenzene (VII-1) are dissolved in 250 ml ethanol, mixed with 3 g Raney nickel and hydrogenated in the autoclave for 6 hours at room temperature with 3 bar of hydrogen. After 6 hours another 3 g Raney nickel are added and hydrogenation is continued for another 16 hours at room temperature with 3 bar hydrogen. The catalyst is then removed by filtration and the solvent removed under vacuum. The crude product is purified by column chromatography (silica gel, 3:1 hexane/methyl t-butyl ether). 32 g (97.3% purity by HPLC, 84.4% theoretical yield) of 2-[1-(isopropylthio)ethyl]aniline are obtained as a yellow oil [logP (pH 2.3)=2.45].

Example (III-2)

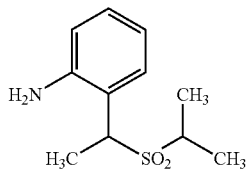

16.2 g (60.5 mmol) 1-[1-(isopropylsulfonyl)ethyl]-2-nitrobenzene (VII-4) in 160 ml methanol are placed in a 500 ml three-necked flask equipped with a stirrer and thermometer, mixed with 160 ml concentrated hydrochloric acid with stirring, and 31.5 g powdered tin (265.2 mmol) are added in portions at 20-40° C. Stirring of the mixture wird is continued at 40° C. for about an hour. The reaction is cooled, filtered and mixed with 1575 ml of an ice-cooled 10% sodium hydroxide solution. Then it is extracted twice with dichloromethane, dried over sodium sulfate, and the solvent is removed under vacuum. The yield is 13.3 g (95.8% purity by HPLC, 92.6% theoretical yield) of 2-[1-(isopropylsulfonyl)ethyl]aniline [logP (pH 2.3)=1.28].

Example (III-3)

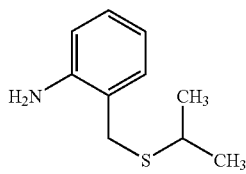

11.8 g (55.6 mmol) 1-[1-(isopropylthio)methyl]-2-nitrobenzene (VII-2) in 150 ml methanol are placed in a 500 ml three-necked flask equipped with a stirrer and thermometer, mixed with 150 ml concentrated hydrochloric acid with stirring, and 17.6 g powdered tin (148.5 mmol) are added in portions at 20-40° C. Stirring of the mixture wird is continued at 40° C. for about an hour. The reaction is cooled, filtered and mixed with 1300 ml of an ice-cooled 10% sodium hydroxide solution. Then it is extracted twice with dichloromethane, dried over sodium sulfate, and the solvent is evaporated under vacuum. The crude product is purified on silica gel with 3:1 hexane/methyl t-butyl ether. 4.6 g (94.6% purity by HPLC, 43.2% theoretical yield) of 2-[1-(isopropylthio)methyl] aniline are obtained as a yellow oil [logP (pH 2.3)=1.94].

Example (III-4)

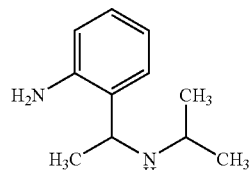

A solution of 5 g (24 mmol) N-[1-(2-nitrophenyl)ethyl] propane-2-amine (VII-5) in 30 ml methanol is mixed with 0.5 g Raney nickel and hydrogenated for 5 hours at 50° C. with 50 bar hydrogen in an autoclave. After cooling, the catalyst is removed by filtration and the solvent removed under vacuum. The yield is 2.8 g (98.1% purity by HPLC, 64.2% theoretical yield) of 2-[1-(isopropylamino)ethyl]aniline [logP (pH 2.3)= 0.05].

Synthesis of Starting Materials of the Formula (IV)

Example (IV-1)

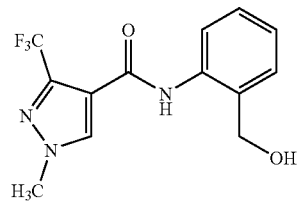

A solution of 34.5 g (0.16 mols) 1-methyl-3-trifluoromethyl-1H-pyrazole-4-carbonyl chloride in 50 ml tetrahydrofuran is added dropwise at room temperature to a solution of 20.0 g (0.16 mols) 2-aminophenylmethanol and 36 ml (0.26 mols) triethylamine in 250 ml tetrahydrofuran. After the exotherm has subsided, the reaction is refluxed for 6 hours, then stirred at room temperature for another 48 hours. The reaction mixture is added to about 250 ml water, extracted with ethyl acetate, washed with 2 N hydrochloric acid gewaschen, dried over magnesium sulfate and concentrated tinder vacuum. Column chromatography (gradient cyclohexane/ethyl acetate) yielded 33.8 g (69% theoretical yield) of N-[2-(hydroxymethyl)phenyl]-1-methyl-3-(trifluoromethyl)-1H-pyrazole-4-carboxamide [logP (pH 2.3)=1.55].

Synthesis of Starting Materials of the Formula (VII)

Example (VII-1)

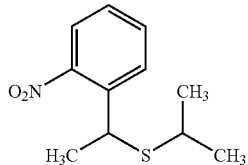

In a 1 liter three-necked flask equipped with a stirrer, dropping funnel and thermometer, 63 g 1-(1-chlorethyl)-2-nitrobenzene (VIII-1) (purity 99.4%, 0.337 mols) in 20 ml acetonitrile are added dropwise at 30-40° C. to 34.8 g (0.354 mol) sodium 2-propanethiolate in 450 ml acetonitrile. The suspension is stirred at 40° C. for another 16 hours, then cooled, and the solvent is removed under vacuum. The residue remaining is dissolved in dichloromethane, washed, dried over sodium sulfate, and the solvent is removed under vacuum. The crude product is purified by column chromatography (silica gel, 29:1 hexane/acetone). 48 g (98.8% purity by HPLC, 62.4% theoretical yield) of 1-[1-(isopropylthio)ethyl]-2-nitrobenzene are obtained as a yellow oil [logP (pH 2.3)=3.89].

Example (VII-2)

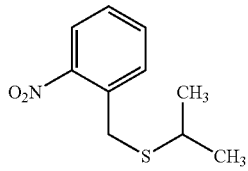

In a 250 ml three-necked flask equipped with a stirrer, dropping funnel and thermometer, 17.2 g (0.1 mol) 2-nitrobenzylchloride in 20 ml acetonitrile are added dropwise to 10.3 g (0.105 mol) sodium 2-propanethiolate in 75 ml acetonitrile, with cooling to maintain the temperature at 30-40° C. The suspension is stirred for another 16 hours at 40-50° C. To complete the reaction, another 6 g sodium 2-propanethiolate (0.061 mol) are added and stirring is continued another 24 hours at 40-50° C. The reaction is cooled and the solvent removed under vacuum. The residue is dissolved in methyl tert-butyl ether, washed and dried over sodium sulfate. The sodium sulfate is removed by filtration, and the solution is concentrated under vacuum. The crude product is purified by column chromatography (silica gel, 50:1 cyclohexane/ethyl acetate). 11.8 g (92% purity by HPLC, 51.2% theoretical yield) of 1-[1-(isopropylthio)methyl]-2-nitrobenzene are obtained as a brown oil [logP (pH 2.3)=3.28].

Example (VI-3)

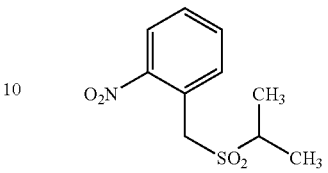

32.8 g 1-[1-(isopropylthio)methyl]-2-nitrobenzene (VII-2) (0.155 mol) in 465 ml dichloromethane are placed in a 1 liter three-necked flask equipped with a stirrer, dropping funnel and thermometer, and 14.3 g formic acid (0.31 mol) and 1.6 g ammonium molybdate are added sequentially with stirring. 45.3 g (0.466 mol) of a 35% aqueous hydrogen peroxide solution are added dropwise at room temperature with fast stirring. The mixture is stirred for another 16 hours. Then the organic phase is removed, washed once with dilute sodium hydrogen sulfite solution and once with water, then the organic solution is dried over sodium sulfate. The solvent is distilled off under vacuum and the residue is stirred with diethyl ether, the precipitated product filtered and dried. 30.5 g 1-[(isopropylsulfonyl)methyl]-2-nitrobenzene (99% purity by HPLC, 80% theoretical yield) are obtained as a yellow solid [logP (pH 2.3)=1.63].

Example (VII-4)

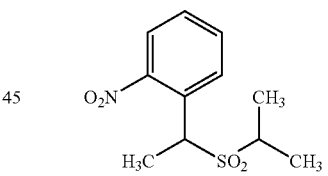

18.9 g 1-[1-(isopropylsulfonyl)methyl]-2-nitrobenzene (VII-3) (77.7 mmol) in 390 nil acetonitrile are placed in a 1 liter three-necked flask equipped with a stirrer, dropping funnel and thermometer, and 90.1 g (652 mmol) potassium carbonate, 0.26 g 18-crown-6 and 12.1 g (85.5 mmol) iodomethane are added sequentially. The reaction is stirred for 4 hours under reflux, then another 2.5 g iodomethane (17.6 mmol) are added, and stirring is continued for another 4 hours under reflux. The reaction is cooled and concentrated under vacuum. The residue is dissolved in ethyl acetate, washed with water and dried over sodium sulfate. After the solvent is removed, the crude product is purified by column chromatography (silica gel, 7:3 hexane/acetone). The yield is 16.2 g of 1-[1-(isopropylsulfonyl)ethyl]nitrobenzene (96.1% purity by HPLC, 77.9% theoretical yield). [logP (pH 2) 1.99].

Example (VII-5)

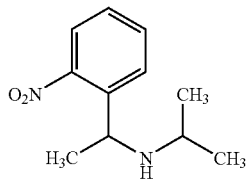

13.8 g 1-(1-chlorethyl)-2-nitrobenzene (VIII-1) (98.3% purity, 73.1 mmol) and 43.2 g isopropylamine (731 mmol) are stirred for 24 hours at 60° C. and inherent pressure in an autoclave. After the reaction mixture is cooled, the excess isopropylamine is removed under vacuum, and the crude product is purified with 4:1 cyclohexane/ethyl acetate on silica gel. The yield is 5 g of N-[1-(2-nitrophenyl)ethyl]propane-2-amine (94.4% purity, 31% theoretical yield) as an oil [logP (pH 2.3)=0.55].

Synthesis of Starting Materials of the Formula (VII)

Example (VIII-1)

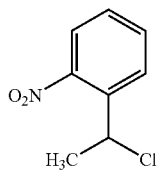

311 g 1-(2-nitrophenyl)ethanol (XI-1) (95.8% purity, 1.78 mol) are dissolved in 3000 ml dimethyl formamide in a 6 liter three-necked flask equipped with a stirrer, dropping funnel and thermometer. 921.4 g (7.13 mol) diisopropylethylamine are added in a single portion, stirred for 5 minutes, then 612.5 g (5.35 mol) methanesulfonyl chloride are added dropwise between 20 to 35° C. with good cooling. After the reaction has subsided, it is stirred for another 90 hours at room temperature, and the solvent is removed under vacuum. Then the residue dissolved in ethyl acetate, washed 3 times with water, dried over sodium sulfate and the solvent is removed under vacuum. The crude product is purified by column chromatography (silica gel, 9:1 hexane/acetone). 219 g of 1-(1-chloroethyl)-2-nitrobenzene (100% purity by HPLC, 66.2% theoretical yield) are obtained as a brown oil [logP (pH 2.3)= 2.87].

Synthesis of Starting Materials of the Formula (XI)

Example (XI-1)

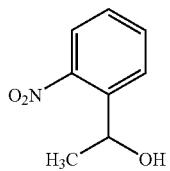

320 g (1.938 mol) 2-nitroacetophenone in 3200 ml methanol are placed in a 6 liter three-necked flask equipped with stirrer, dropping funnel, thermometer and bubble counter, then a solution of 73.3 g (1.938 mol) sodium borohydride in 288 ml water is added dropwise at 30-40° C. with mild cooling. After the reaction has subsided, it is stirred at room temperature for another 16 hours. The reaction is worked up by neutralizing with dilute hydrochloric acid and removing the solvent on a rotary evaporator. The residue is dissolved in dichloromethane, washed with water and dried over sodium sulfate, then the solvent is removed under vacuum. The yield is 311 g of 1-(2-nitrophenyl)ethanol (95.1% purity by HPLC, 91.3% theoretical yield) [logP (pH 2.3)=1.49] as a light-colored oil.

The specified logP values are determined by HPLC on a reverse phase column (C18) in accordance with EEC Directive 79/831 Annex V.A8. Temperature: 43° C.

Eluents for the measurement in the acid range (pH 2.3): 0.1% aqueous phosphoric acid, acetonitrile; linearer gradient of 10% acetonitrile to 90% acetonitrile.

Calibration is performed with unbranched alkyl-2-ones (with 3 to 16 carbon atoms) with known logP values (determination of the logP values based on retention times by linear interpolation between two sequential alkyl ketones).

The lambda max. values were determined for the chromatographic signal peaks from the UV spectra in the 200 nm to 400 nm region.

APPLICATION EXAMPLES

Example A

| Podosphaera test (apple)/protective | |
|---|---|
| Solvents: | 24.5 parts by weight acetone |
| | 24.5 parts by weight dimethyl acetamide |
| Emulsifier: | 1 part by weight alkyl aryl polyglycol ether |

To produce an appropriate active ingredient preparation, one part by weight of the active substance is mixed with the specified quantities of solvent and emulsifying agent, and the concentrate is diluted with water to the desired concentration.

Young plants are sprayed with the active ingredient preparation at the specified application rate to test the effectiveness of protection. After the sprayed coating has dried, the plants are inoculated with an aqueous spore suspension of the apple mildew pathogen *Podosphaera leucotricha*. Then the plants are placed in the greenhouse at about 23° C. with relative humidity of about 70%.

The evaluation is performed ten days after the inoculation. A degree of effectiveness rating of 0% corresponds to the control, with 100% indicating no infestation observed.

TABLE A

Podosphaera test (apple)/protective

| Active substance according to the invention | Application rate of active substance in g/ha | Degree of effectiveness in % |
|---|---|---|
| [pyrazole carboxamide, 3-methyl-1-methyl-5-fluoro, N-(2-(1-(isopropylthio)ethyl)phenyl)] | 100 | 91 |
| [3-difluoromethyl-1-methyl pyrazole carboxamide, N-(2-(1-(isopropylthio)ethyl)phenyl)] | 100 | 84 |
| [3-difluoromethyl-1-methyl pyrazole carboxamide, N-(2-(1-(sec-butylthio)ethyl)phenyl)] | 100 | 94 |

Example B

Venturia test (apple)/protective

| Solvents: | 24.5 parts by weight acetone |
| | 24.5 parts by weight dimethyl acetamide |
| Emulsifier: | 1 part by weight alkyl aryl polyglycol ether |

To produce an appropriate active ingredient preparation, one part by weight of the active substance is mixed with the specified quantities of solvent and emulsifying agent, and the concentrate is diluted with water to the desired concentration.

Young plants are sprayed with the active ingredient preparation at the specified application rate to test the effectiveness of protection. After the sprayed coating has dried, the plants are inoculated with an aqueous conidia suspension of the apple scab pathogen *Venturia inaequalis* and are then kept in an incubator at 20° C. and 100% relatively humidity for one day.

Then the plants are placed in the greenhouse at about 21° C. with relative humidity of about 90%.

The evaluation is performed ten days after the inoculation. A degree of effectiveness rating of 0% corresponds to the control, with 100% indicating no infestation observed.

TABLE B

Venturia test (apple)/protective

| Active substance according to the invention | Application rate of active substance in g/ha | Degree of effectiveness in % |
|---|---|---|
| [3-methyl-1-methyl-5-fluoro pyrazole carboxamide, N-(2-(1-(isopropylthio)ethyl)phenyl)] | 100 | 95 |
| [3-trifluoromethyl thiazole carboxamide, N-(2-(1-(sec-butylthio)propyl)phenyl)] | 100 | 89 |
| [3-difluoromethyl-1-methyl pyrazole carboxamide, N-(2-(1-(sec-butylthio)ethyl)phenyl)] | 100 | 99 |

Example C

Botrytis test (bean)/protective

| Solvents: | 24.5 parts by weight acetone |
| | 24.5 parts by weight dimethyl acetamide |
| Emulsifier: | 1 part by weight alkyl aryl polyglycol ether |

To produce an appropriate active ingredient preparation, one part by weight of the active substance is mixed with the specified quantities of solvent and emulsifying agent, and the concentrate is diluted with water to the desired concentration.

Young plants are sprayed with the active ingredient preparation at the specified application rate to test the effectiveness of protection. After the sprayed coating has dried, two small pieces of agar with cultured *Botrytis cinerea* are placed on each leaf. The inoculated plants are placed in a darkened chamber at about 20° C. and 100% relatively humidity.

Two days after the inoculation, the size of the infestation spots on the leaves is evaluated. A degree of effectiveness rating of 0% corresponds to the control, with 100% indicating no infestation observed.

TABLE C

Botrytis test (bean)/protective

| Active substance according to the invention | Application rate of active substance in g/ha | Degree of effectiveness in % |
|---|---|---|
| [Structure: F3C-pyrazole(N-CH3)-C(O)NH-phenyl-CH(CH3)-S-CH(CH3)2] | 500 | 84 |
| [Structure: F2HC-pyrazole(N-CH3)-C(O)NH-phenyl-CH(CH3)-S-CH(CH3)2] | 500 | 100 |
| [Structure: F3C-thiazole(CH3)-C(O)NH-phenyl-CH(CH3)-S-CH(CH3)-CH2CH3] | 500 | 99 |
| [Structure: F3C-pyrazole(N-CH3)-C(O)NH-phenyl-CH(CH3)-S-CH(CH3)-CH2CH3] | 500 | 100 |
| [Structure: F2HC-pyrazole(N-CH3)-C(O)NH-phenyl-CH(CH3)-S-CH(CH3)-CH2CH3] | 500 | 97 |
| [Structure: F3C-pyrrole(N-CH3)-C(O)NH-phenyl-CH(CH3)-S-CH(CH3)2] | 500 | 97 |

Example D

Puccinia test (wheat)/protective

| | |
|---|---|
| Solvent: | 50 parts by weight N,N-dimethyl acetamide |
| Emulsifier: | 1 part by weight alkyl aryl polyglycol ether |

To produce an appropriate active ingredient preparation, one part by weight of the active substance is mixed with the specified quantities of solvent and emulsifying agent, and the concentrate is diluted with water to the desired concentration.

Young plants are sprayed with the active ingredient preparation at the specified application rate to test the effectiveness of protection. After the sprayed coating has dried, the plants are sprayed with a conidia suspension of *Puccinia recondita*. The plants are kept in an incubator at 20° C. and 100% relatively humidity for 48 hours.

Then the plants are placed in a greenhouse at a temperature of about 20° C. and a relatively humidity of 80%, in order to promote the development of rust spots.

The evaluation is performed ten days after the inoculation. A degree of effectiveness rating of 0% corresponds to the control, with 100% indicating no infestation observed.

TABLE D

Puccinia test (wheat)/protective

| Active substance according to the invention | Application rate of active substance in g/ha | Degree of effectiveness in % |
|---|---|---|
| [Structure: F3C-pyrazole(N-CH3)-C(O)NH-phenyl-CH(CH3)-S-CH(CH3)2] | 500 | 100 |
| [Structure: F2HC-thiazole(CH3)-C(O)NH-phenyl-CH2-S-CH(CH3)2] | 500 | 93 |
| [Structure: F3C-thiazole(CH3)-C(O)NH-phenyl-CH(CH3)-S-CH(CH3)-CH2CH3] | 500 | 100 |

TABLE D-continued
Puccinia test (wheat)/protective
| Active substance according to the invention | Application rate of active substance in g/ha | Degree of effectiveness in % |
|---|---|---|
| 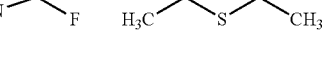 | 500 | 100 |
| 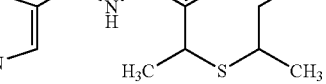 | 500 | 100 |
| 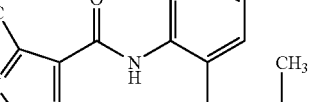 | 500 | 100 |
| 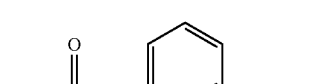 | 500 | 100 |
| 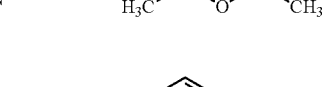 | 500 | 100 |
| 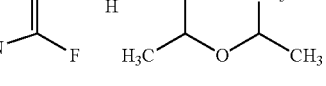 | 500 | 100 |
| 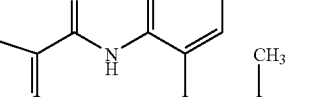 | 500 | 100 |
TABLE D-continued
Puccinia test (wheat)/protective
| Active substance according to the invention | Application rate of active substance in g/ha | Degree of effectiveness in % |
|---|---|---|
| 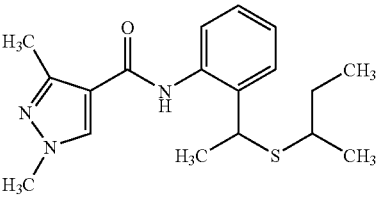 | 500 | 100 |
| 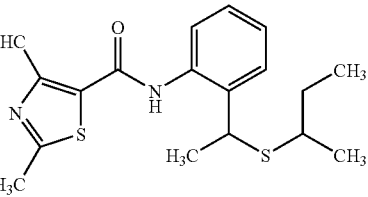 | 500 | 100 |
| 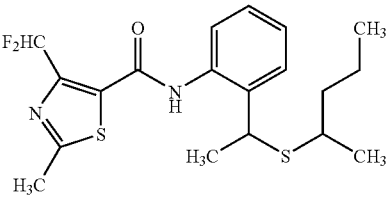 | 500 | 100 |
| 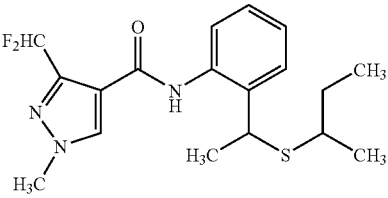 | 500 | 100 |
| 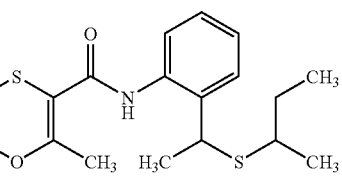 | 500 | 100 |
| 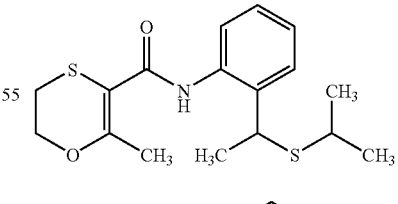 | 500 | 100 |

TABLE D-continued

Puccinia test (wheat)/protective

| Active substance according to the invention | Application rate of active substance in g/ha | Degree of effectiveness in % |
|---|---|---|
| pyrazole-carboxamide with F, CF3, N-CH3 | 500 | 96 |
| pyrazole-carboxamide with Cl, CH3, N-CH3, S-iPr | 500 | 100 |
| pyrazole-carboxamide with Cl, CH3, N-CH3, S-sec-Bu | 500 | 100 |
| pyrazole-carboxamide with Cl, CH3, N-CH3, S-cyclopentyl | 500 | 100 |

Example E

Alternaria test (tomato)/protective

| Solvent: | 49 parts by weight N,N-dimethyl formamide |
|---|---|
| Emulsifier: | 1 part by weight alkyl aryl polyglycol ether |

To produce an appropriate active ingredient preparation, one part by weight of the active substance is mixed with the specified quantities of solvent and emulsifying agent, and the concentrate is diluted with water to the desired concentration.

Young tomato plants are sprayed with the active ingredient preparation at the specified application rate to test the effectiveness of protection. One day after treatment, the plants are inoculated with a spore suspension of *Alternaria solani* and are kept for 24 hours at 100% relatively humidity and 20° C. Subsequently, the plants are kept at 96% relatively humidity and a temperature of 20° C.

The evaluation is performed seven days after the inoculation. A degree of effectiveness rating of 0% corresponds to the control, with 100% indicating no infestation observed.

TABLE E

Alternaria test (tomato)/protective

| Active substance according to the invention | Application rate of active substance in g/ha | Degree of effectiveness in % |
|---|---|---|
| pyrazole-carboxamide with CF3, N-CH3, O-iPr | 750 | 95 |
| pyrazole-carboxamide with CH3, F, N-CH3, S-iPr | 750 | 90 |
| 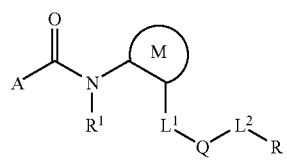 pyrazole-carboxamide with CH3, F, N-CH3, S-sec-Bu | 750 | 95 |

The invention claimed is:

1. A carboxamide of formula (I)

$$\underset{R^1}{\overset{O}{\underset{\|}{A-C-N}}}\overset{M}{\underset{L^1-Q-L^2-R}{\bigcirc}}$$ (I)

in which $R^1$ stands for hydrogen, $C_1$-$C_8$ alkyl, $C_1$-$C_6$ alkylsulfinyl, $C_1$-$C_6$ alkylsulfonyl, $C_1$-$C_4$-alkoxy-$C_1$-$C_4$-alkyl, $C_3$-$C_8$ cycloalkyl; $C_1$-$C_6$ haloalkyl, $C_1$-$C_4$ haloalkylthio, haloalkylsulfinyl, $C_1$-$C_4$ haloalkylsulfonyl, halo-$C_1$-$C_4$-alkoxy-$C_1$-$C_4$-alkyl, $C_3$-$C_8$ halocycloalkyl with 1 to 9 fluorine, chlorine, bromine atoms, or combinations thereof in each case; or formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl with 1 to 13 fluorine, chlorine, and/or bromine atoms, or combinations thereof in each case; or ($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl with 1 to 9 fluorine, chlorine, bromine atoms, or combinations thereof in each case; or —C(=O)C(=O)R$^2$, —CONR$^3$R$^4$ or —CH$_2$NR$^5$R$^6$, R$^2$ stands for hydrogen, C$_1$-C$_8$ alkyl, C$_1$-C$_8$ alkoxy, C$_1$-C$_4$-alkoxy-C$_1$-C$_4$-alkyl, C$_3$-C$_8$ cycloalkyl; C$_1$-C$_6$ haloalkyl, C$_1$-C$_6$ haloalkoxy, halo-C$_1$-C$_4$-alkoxy$_1$-C$_4$-alkyl, C$_3$-C$_8$ halocycloalkyl with 1 to 9 fluorine, chlorin, bromine atoms, or combinations thereof in each case, R$^3$ and R$^4$ stand independently of one another in each case for hydrogen, C$_1$-C$_8$ alkyl, C$_1$-C$_4$-alkoxy$_1$-C$_4$-alkyl, C$_3$-C$_8$ cycloalkyl; C$_1$-C$_8$ haloalkyl, halo-C$_1$-C$_4$-alkoxy-C$_1$-C$_4$-alkyl, C$_3$-C$_8$ halocycloalkyl with 1 to 9 fluorine, chlorine, bromine atoms, or combinations thereof in each case, or R$^3$ and R$^4$ form a substituted, saturated heterocycle with 5 to 8 ring atoms together with the nitrogen atom to which they are bound, with single or multiple, the same or various substitution by halogen or C$_1$-C$_4$ alkyl, whereby the heterocycle can contain 1 or 2 additional, non-adjacent hetero atoms constituted by oxygen, sulfur or NR$^7$, R$^5$ and R$^6$ stand independently of one another for hydrogen, C$_1$-C$_8$-alkyl, C$_3$-C$_8$ cycloalkyl; C$_1$-C$_8$ haloalkyl, C$_3$-C$_8$ halocycloalkyl with 1 to 9 fluorine, chlorine, bromine atoms, or combinations thereof in each case, or R$^5$ and R$^6$ form a substituted, saturated heterocycle with 5 to 8 ring atoms together with the nitrogen atom to which they are bound, with single or multiple, the same or various substitution by halogen or C$_1$-C$_4$ alkyl, whereby the heterocycle can contain 1 or 2 additional, non-adjacent hetero atoms constituted by oxygen, sulfur or NR$^7$, R$^7$ stands for hydrogen or C$_1$-C$_6$ alkyl, M is a phenyl ring with a single substitution by R$^8$, R$^8$ stands for hydrogen, fluorine, chlorine, methyl, isopropyl, methylthio or trifluoromethyl, or R$^8$ stands for methoxy, L$^1$ stands for C$_1$-C$_{10}$ alkylene (alkanediyl), Q stands for O, S, SO, SO$_2$ or NR$^9$, L$^2$ stands for a direct link, SiR$^{10}$R$^{11}$ or CO, R stands for hydrogen, C$_1$-C$_8$ alkyl, C$_1$-C$_8$ alkoxy, C$_1$-C$_4$-alkoxy-C$_1$-C$_4$-alkyl, C$_1$-C$_4$-alkylthio-C$_1$-C$_4$-alkyl, C$_2$-C$_8$ alkenyl, C$_2$-C$_8$ alkynyl, C$_1$-C$_6$ haloalkyl, C$_2$-C$_6$ haloalkenyl, C$_2$-C$_6$ haloalkynyl or C$_3$-C$_6$ cycloalkyl, R$^9$ stands for hydrogen, C$_1$-C$_8$ alkyl, C$_1$-C$_4$-alkoxy-C$_1$-C$_4$-alkyl, C$_1$-C$_4$-alkylthio-C$_1$-C$_4$-alkyl, C$_2$-C$_8$ alkenyl, C$_2$-C$_8$ alkynyl, C$_1$-C$_6$ haloalkyl, C$_2$-C$_6$ haloalkenyl, C$_2$-C$_6$ haloalkynyl or C$_3$-C$_6$ cycloalkyl, R$^{10}$ and R$^{11}$ stand independently of one another for hydrogen, C$_1$-C$_8$ alkyl, C$_1$-C$_8$ alkoxy, C$_1$-C$_4$-alkoxy-C$_1$-C$_4$-alkyl, C$_1$-C$_4$-alkylthio-C$_1$-C$_4$-alkyl or C$_1$-C$_6$ haloalkyl, A is a group of formula (A1)

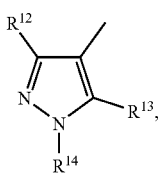

(A1)

in which

R$^{12}$ stands for hydrogen, cyano, halogen, nitro, C$_1$-C$_4$ alkyl, C$_1$-C$_4$ alkoxy, C$_1$-C$_4$ alkylthio, C$_3$-C$_6$ cycloalkyl, C$_1$-C$_4$ haloalkyl, C$_1$-C$_4$ haloalkoxy or C$_1$-C$_4$ haloalkylthio, in each case with 1 to 5 halogen atoms, aminocarbonyl or aminocarbonyl-C$_1$-C$_4$-alkyl, R$^{13}$ stands for hydrogen, halogen, cyano, C$_1$-C$_4$ alkyl, C$_1$-C$_4$ alkoxy or C$_1$-C$_4$ alkylthio, R$^{14}$ stands for hydrogen, C$_1$-C$_4$ alkyl, hydroxy-C$_1$-C$_4$ alkyl, C$_2$-C$_6$ alkenyl, C$_3$-C$_6$ cycloalkyl, C$_1$-C$_4$-alkylthio-C$_1$-C$_4$-alkyl, C$_1$-C$_4$-alkoxy-C$_1$-C$_4$-alkyl, C$_1$-C$_4$ haloalkyl, C$_1$-C$_4$-haloalkylthio-C$_1$-C$_4$-alkyl, C$_1$-C$_4$-haloalkoxy-C$_1$-C$_4$-alkyl in each case with 1 to 5 halogen atoms, or phenyl.

2. A carboxamide of the formula (I) according to claim 1,

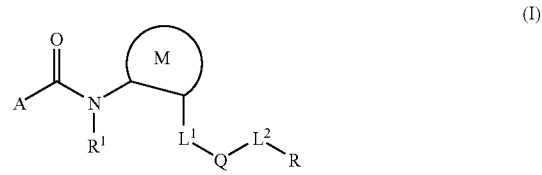

(I)

in which when L$^2$ is a direct link, R is hydrogen, C$_1$-C$_8$ alkyl, C$_1$-C$_4$-alkylthio-C$_1$-C$_4$-alkyl, C$_2$-C$_8$ alkenyl, C$_2$-C$_8$ alkynyl, C$_1$-C$_6$ haloalkyl, C$_2$-C$_6$ haloalkenyl, C$_2$-C$_6$ haloalkynyl or C$_3$-C$_6$ cycloalkyl.

3. A carboxamide of formula (I) according to claim 1 or 2, in which

R$^1$ stands for hydrogen, C$_1$-C$_6$ alkyl, C$_1$-C$_4$ alkylsulfinyl, alkylsulfonyl, C$_1$-C$_3$-alkoxy-C$_1$-C$_3$-alkyl, C$_3$-C$_6$ cycloalkyl; C$_1$-C$_4$ haloalkyl, C$_1$-C$_4$ haloalkylthio, haloalkylsulfinyl, C$_1$-C$_4$ haloalkylsulfonyl, halo-C$_1$-C$_3$-alkoxy-C$_1$-C$_3$-alkyl, C$_3$-C$_8$ halocycloalkyl with 1 to 9 fluorine, chlorine, bromine atoms, or combinations thereof in each case; or formyl, formyl-C$_1$-C$_3$-alkyl, (C$_1$-C$_3$-alkyl)carbonyl-C$_1$-C$_3$-alkyl, (C$_1$-C$_3$-alkoxy)carbonyl-C$_1$-C$_3$-alkyl; halo-(C$_1$-C$_3$-alkyl)carbonyl-C$_1$-C$_3$-alkyl, halo-(C$_1$-C$_3$-alkoxy)carbonyl-C$_1$-C$_3$-alkyl with 1 to 13 fluorine, chlorine, bromine atoms, or combinations thereof in each case; or (C$_1$-C$_6$ alkyl)carbonyl, (C$_1$-C$_4$ alkoxy)carbonyl, (C$_1$-C$_3$-alkoxy-C$_1$-C$_3$-alkyl)carbonyl, (C$_3$-C$_6$ cycloalkyl)carbonyl; (C$_1$-C$_4$ haloalkyl)carbonyl, (C$_1$-C$_4$ haloalkoxy)carbonyl, (halo-C$_1$-C$_3$-alkoxy-C$_1$-C$_3$-alkyl)carbonyl, (C$_3$-C$_6$ halocycloalkyl)carbonyl with 1 to 9 fluorine, chlorine, bromine atoms, or combinations thereof in each case; or —C(=O)C(=O)R$^2$, —CONR$^3$R$^4$ or —CH$_2$NR$^5$R$^6$, R$^2$ stands for hydrogen, C$_1$-C$_6$ alkyl, C$_1$-C$_4$ alkoxy, C$_1$-C$_3$-alkoxy-C$_1$-C$_3$-alkyl, C$_3$-C$_6$ cycloalkyl; C$_1$-C$_4$ haloalkyl, C$_1$-C$_4$ haloalkoxy, halo-C$_1$-C$_3$-alkoxy-C$_1$-C$_3$-alkyl, C$_3$-C$_6$ halocycloalkyl with 1 to 9 fluorine, chlorine, bromine atoms, or combinations thereof in each case, R$^3$ and R$^4$ stand independently of one another in each case for hydrogen, C$_1$-C$_6$ alkyl, C$_1$-C$_3$-alkoxy-C$_1$-C$_3$-alkyl, C$_3$-C$_6$ cycloalkyl; haloalkyl, halo-C$_1$-C$_3$-alkoxy-C$_1$-C$_3$-alkyl, C$_3$-C$_6$ halocycloalkyl with 1 to 9 fluorine, chlorine, bromine atoms, or combinations thereof in each case, or R$^3$ and R$^4$ form a substituted, saturated heterocycle with 5 to 8 ring atoms together with the nitrogen atom to which they are bound, with single or multiple, the same or various substitution by halogen or C$_1$-C$_4$ alkyl, whereby the heterocycle can contain 1 or 2 additional, non-adjacent hetero atoms constituted by oxygen, sulfur or NR$^7$, R$^5$ and R$^6$ stand independently of one another for hydrogen, C$_1$-C$_6$ alkyl, C$_3$-C$_6$ cycloalkyl; C$_1$-C$_4$ haloalkyl, C$_3$-C$_6$ halocycloalkyl with 1 to 9 fluorine, chlorine, bromine atoms, or combinations thereof in each case, or $R^5$ and $R^6$ form a substituted, saturated heterocycle with 5 to 8 ring atoms together with the nitrogen atom to which they are bound, with single or multiple, the same or various substitution by halogen or $C_1$-$C_4$ alkyl, whereby the heterocycle can contain 1 or 2 additional, non-adjacent hetero atoms constituted by oxygen, sulfur or $NR^7$, $R^7$ stands for hydrogen or $C_1$-$C_4$ alkyl, M stands for

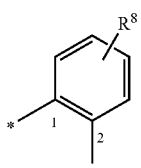

(M-1)

whereby the bond marked with an asterisk is linked to the amide, $R^8$ stands for hydrogen, fluorine, chlorine, methyl, isopropyl, methylthio or trifluoromethyl, or $R^8$ stands for methoxy, $L^1$ stands for $C_1$-$C_{10}$ alkylene (alkanediyl), Q stands for O, S, SO, $SO_2$ or $NR^9$, $L^2$ stands for a direct link, $SiR^{10}R^{11}$ or CO, R stands for hydrogen, $C_1$-$C_6$ alkyl, $C_1$-$C_6$ alkoxy, $C_1$-$C_3$-alkoxy-$C_1$-$C_3$-alkyl, $C_1$-$C_3$-alkylthio-$C_1$-$C_3$-alkyl or $C_1$-$C_4$ haloalkyl or $C_3$-$C_6$ cycloalkyl, $R^9$ stands for hydrogen, $C_1$-$C_6$ alkyl, $C_1$-$C_3$-alkoxy-$C_1$-$C_3$-alkyl, $C_1$-$C_3$-alkylthio-$C_1$-$C_3$-alkyl or $C_3$-$C_6$ cycloalkyl, $R^{10}$ and $R^{11}$ stand independently of one another preferably for $C_1$-$C_6$ alkyl, $C_1$-$C_6$ alkoxy, $C_1$-$C_3$-alkoxy-$C_1$-$C_3$-alkyl or $C_1$-$C_3$-alkylthio-$C_1$-$C_3$-alkyl, A stands for the group of the formula (A1)

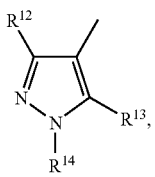

(A1)

in which $R^{12}$ stands for hydrogen, cyano, fluorine, chlorine, bromine, iodine, methyl, ethyl, isopropyl, methoxy, ethoxy, methylthio, ethylthio, cyclopropyl, $C_1$-$C_2$ haloalkyl, $C_1$-$C_2$ haloalkoxy in each case with 1 to 5 fluorine, chlorine, bromine atoms, or combinations thereof, trifluoromethylthio, difluoromethylthio, aminocarbonyl, aminocarbonylmethyl or aminocarbonylethyl, $R^{13}$ stands for hydrogen, fluorine, chlorine, bromine, iodine, methyl, ethyl, methoxy, ethoxy, methylthio or ethylthio, $R^{14}$ stands for hydrogen, methyl, ethyl, n-propyl, isopropyl, $C_1$-$C_2$ haloalkyl with 1 to 5 fluorine, chlorine, bromine atoms, or combinations thereof, hydroxymethyl, hydroxyethyl, cyclopropyl, cyclopentyl, cyclohexyl or phenyl.

4. A process for synthesizing a carboxamide of the formula (I) according to claim 1, comprising (a) reacting a carboxylic acid derivative of formula (II)

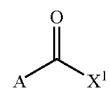

(II)

in which

A is as defined in claim 1 and $X^1$ stands for halogen or hydroxy, with an aniline derivative of formula (III)

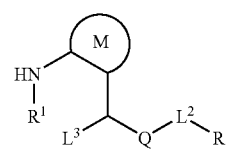

(III)

in which $R^1$, M, Q, $L^2$ and R are as defined in claim 1 and $L^3$ stands for hydrogen or $C_1$-$C_9$ alkyl, optionally in the presence of a catalyst, optionally in the presence a condensation agent, optionally in the presence of an acid binder and optionally in the presence of a diluent, or (b) reacting a carboxamide of formula (IV)

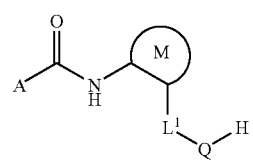

(IV)

in which M, $L^1$, Q and A are as defined in claim 1 with a compound of formula (V),

(V)

in which $L^2$ and R are as defined in claim 1 and

Y stands for halogen, triflate (trifluoromethylsulfonyl), mesylate (methylsulfonyl) or tosylate (4-methylphenylsulfonyl), in the presence of a base and in the presence of a dilution medium, or (c) reacting a carboxamide of formula (I-a)

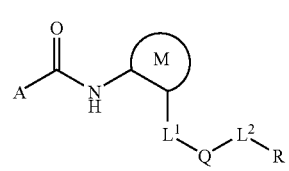

(I-a)

in which M, $L^1$, Q, $L^2$, R and A are ad defined in claim 1, with a halide of formula (VI)

$$R^{1-A}\text{—}X^2 \tag{VI}$$

in which $X^2$ stands for chlorine, bromine or iodine, $R^{1-A}$ stands for $C_1$-$C_8$ alkyl, $C_1$-$C_6$ alkylsulfinyl, $C_1$-$C_6$ alkylsulfonyl, $C_1$-$C_4$-alkoxy-$C_1$-$C_4$-alkyl, $C_3$-$C_8$ cycloalkyl; $C_1$-$C_6$ haloalkyl, $C_1$-$C_4$ haloalkylthio, haloalkylsulfinyl, $C_1$-$C_4$ haloalkylsulfonyl, halo-$C_1$-$C_4$-alkoxy-$C_1$-$C_4$-alkyl, $C_3$-$C_8$ halocycloalkyl with 1 to 9 fluorine, chlorin; bromine atoms, or combinations thereof in each case; formyl, formyl-$C_1$-$C_3$-alkyl, ($C_1$-$C_3$-alkyl)carbonyl-$C_1$-$C_3$-alkyl, ($C_1$-$C_3$-alkoxy) carbonyl-$C_1$-$C_3$-alkyl; halo-($C_1$-$C_3$ alkyl)carbonyl-$C_1$-$C_3$-alkyl, halo-($C_1$-$C_3$ alkoxy)carbonyl-$C_1$-$C_3$-alkyl with 1 to 13 fluorine, chlorine, and/or bromine atoms, or combinations thereof in each case;

($C_1$-$C_8$ alkyl)carbonyl, ($C_1$-$C_8$ alkoxy)carbonyl, ($C_1$-$C_4$-alkoxy-$C_1$-$C_4$-alkyl)carbonyl, ($C_3$-$C_8$ cycloalkyl)carbonyl; ($C_1$-$C_6$ haloalkyl)carbonyl, ($C_1$-$C_6$ haloalkoxy)carbonyl, (halo-$C_1$-$C_4$-alkoxy-$C_1$-$C_4$-alkyl)carbonyl, ($C_3$-$C_8$ halocycloalkyl)carbonyl with 1 to 9 fluorine, chlorine, bromine atoms, or combinations thereof in each case; or —C(=O)C(=O)$R^2$, —CONR$^3$R$^4$ or —CH$_2$NR$^5$R$^6$, whereby $R^2$, $R^3$, $R^4$, $R^5$ and $R^6$ are as defined in claim 1, in the presence of a base and in the presence of a dilution medium.

5. A composition comprising at least one carboxamide of the formula (I) according to claim 1 and one or more extenders, surface active materials, or combinations thereof.

6. A process for combating undesired microorganisms, comprising applying a carboxamide of the formula (I) according to claim 1 to microorganisms, their environment, or a combination thereof.

7. A process for preparing a composition to combat undesired microorganisms, comprising mixing a carboxamide of the formula (I) according to claim 1 with one or more extenders, surface active materials, or combinations thereof.

* * * * *